(12) United States Patent
Jeanguenat et al.

(10) Patent No.: US 9,756,858 B2
(45) Date of Patent: Sep. 12, 2017

(54) INSECTICIDES

(75) Inventors: Andre Jeanguenat, Stein (CH); Andrew Edmunds, Stein (CH); Roger Graham Hall, Stein (CH); Thomas Pitterna, Stein (CH); Sebastian Rendler, Stein (CH)

(73) Assignee: Syngenta Participations AG, Basel (CH)

( * ) Notice: Subject to any disclaimer, the term of this patent is extended or adjusted under 35 U.S.C. 154(b) by 181 days.

(21) Appl. No.: 14/117,864

(22) PCT Filed: Jun. 7, 2012

(86) PCT No.: PCT/EP2012/060797
§ 371 (c)(1),
(2), (4) Date: Nov. 15, 2013

(87) PCT Pub. No.: WO2012/168361
PCT Pub. Date: Dec. 13, 2012

(65) Prior Publication Data
US 2014/0088154 A1 Mar. 27, 2014

(30) Foreign Application Priority Data
Jun. 10, 2011 (EP) .................................. 11169423

(51) Int. Cl.
| C07D 417/04 | (2006.01) |
| A01N 43/78 | (2006.01) |
| A01N 43/80 | (2006.01) |
| A01N 43/82 | (2006.01) |
| A01N 43/90 | (2006.01) |
| C07D 417/14 | (2006.01) |

(52) U.S. Cl.
CPC ............ *A01N 43/78* (2013.01); *A01N 43/80* (2013.01); *A01N 43/82* (2013.01); *A01N 43/90* (2013.01); *C07D 417/04* (2013.01); *C07D 417/14* (2013.01)

(58) Field of Classification Search
CPC ................................................. C07D 417/04
USPC ........................................ 546/270.4; 514/342
See application file for complete search history.

(56) References Cited

U.S. PATENT DOCUMENTS

| 4,260,765 A | 4/1981 | Harrison et al. |
| 2014/0296064 A1* | 10/2014 | Kaiser .................... A01N 43/78 |
| | | 504/100 |

FOREIGN PATENT DOCUMENTS

| EP | 2198710 A1 | 6/2010 |
| WO | 2009/149858 A1 | 12/2009 |
| WO | 2010/006713 A2 | 1/2010 |
| WO | 2010/129497 A1 | 11/2010 |

OTHER PUBLICATIONS

International Search Report from international patent application No. PCT/EP2012/060797.

* cited by examiner

*Primary Examiner* — Patricia L Morris
(74) *Attorney, Agent, or Firm* — James Cueva

(57) ABSTRACT

Compounds of formula I

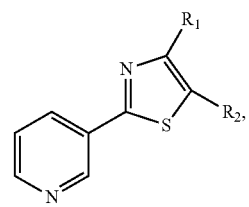

(I)

wherein the substituents are as defined in claim 1, and the agrochemically acceptable salts and all stereoisomers and tautomeric forms of the compounds of formula I can be used as agrochemical active ingredients and can be prepared in a manner known per se.

2 Claims, No Drawings

INSECTICIDES

This application is a 371 of International Application No. PCT/EP2012/060797 filed Jun. 7, 2012 which claims priority to European Patent No. 11169423.8 filed Jun. 10, 2011, to which the contents of all are incorporated herein by reference.

The present invention relates to insecticidally active 2-(3-pyridyl)-thiazole derivatives, to processes for their preparation, to compositions comprising those compounds, and to their use for controlling insects or representatives of the order Acarina.

2-(3-Pyridyl)-thiazole derivatives with insecticidal action are known and described, for example, in U.S. Pat. No. 4,080,457, WO 2009/149858, WO 2010/129497, WO 2010/006713 and WO 2011/138285.

There have now been found novel 2-(3-pyridyl)-thiazole derivatives with pesticidal properties. The present invention accordingly relates to compounds of formula I

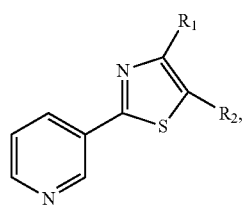

wherein
$R_1$ is chloro; and
$R_2$ is a five- to ten-membered monocyclic or fused bicyclic ring system which can be aromatic, partially saturated or fully saturated and can contain 1 to 4 hetero atoms selected from the group consisting of nitrogen, oxygen and sulfur, it not being possible for each ring system to contain more than 2 oxygen atoms and more than 2 sulfur atoms, said five- to ten-membered ring system can be mono- to polysubstituted by substituents independently selected from the group consisting of halogen, $C_1$-$C_6$alkyl, $C_1$-$C_6$alkoxy, $C_1$-$C_6$alkylthio, $C_1$-$C_6$alkylamino, $C_1$-$C_6$di-alkylamino, $C_1$-$C_6$alkoxycarbonylamino, pyrimidinyl, thiazolyl, pyridinyl, pyrazinyl, pyridazinyl, pyrazinyloxy, imidazolyl and oxazolyl, wherein said pyrimidinyl, thiazolyl, pyridinyl, pyrazinyl, pyridazinyl, pyrazinyloxy, imidazolyl and oxazolyl in turn can be mono- to polysubstituted by substituents independently selected from the group consisting of halogen, $C_1$-$C_6$alkyl, di-$C_1$-$C_4$alkyl-phosphinoylmethyl-aminocarbonyl, $C_1$-$C_6$alkoxycarbonylamino, $C_1$-$C_6$alkoxy, $C_1$-$C_6$alkylthio, $C_1$-$C_6$alkylamino, $C_1$-$C_6$di-alkylamino, pyridinyl, pyrimidinyl, pyrazinyloxy and oxazolyl, which pyridinyl, pyrimidinyl, pyrazinyloxy and oxazolyl in turn can be substituted by substituents independently selected from the group consisting of halogen, $C_1$-$C_6$alkyl and $C_1$-$C_6$alkoxy; or
$R_2$ is a group —C(O)N($R_3$)$R_4$; wherein
$R_3$ is hydrogen, $C_1$-$C_6$alkyl, which can be mono- to polysubstituted by substituents selected from the group consisting of $C_3$-$C_6$cycloalkyl, $C_1$-$C_6$alkylthio, $C_1$-$C_6$haloalkyl, $C_1$-$C_6$alkylsulfinyl, halogen, cyano, hydroxy, $C_1$-$C_6$alkoxy, $C_2$-$C_6$alkenyl, $C_2$-$C_6$alkynyl, $C_1$-$C_6$alkoxy-$C_3$-$C_6$alkynyl, oxolanyl, dioxolanyl, thienyl, thietanyl, thiethanyloxide, thiethanyldioxide, di-$C_1$-$C_4$alkyl-phosphinoylmethyl, 1-H-benzoimidazol-2-yl, benzo[1,3]dioxolyl, morpholinyl, piperidinyl, pyrimidinyl, pyrrolidinyl, benzylthio, 2,3-dihydro-benzo[1,4]dioxinyl, 1H-indolyl, furyl, —C=N—O—$C_1$-$C_6$alkyl, $C_1$-$C_6$alkylcarbonylamino, phenoxy and phenyl, said phenyl in turn can be mono- to polysubstituted by substituents selected from the group consisting of hydroxy, halogen, $C_1$-$C_6$alkoxy, $C_1$-$C_6$haloalkoxy, pyrazolyl, piperidinyl, phenoxy and $C_1$-$C_4$alkylsulfonyl;
or $R_3$ is $C_1$-$C_6$alkyl, which is substituted by pyridyl, which pyridyl in turn can be mono- to polysubstituted by substituents selected from the group consisting of halogen and $C_1$-$C_4$haloalkyl;
or $R_3$ is $C_1$-$C_6$alkyl, which is substituted by phenoxy, which phenoxy in turn can be mono- to polysubstituted by substituents selected from the group consisting of halogen and $C_1$-$C_4$alkyl;
or $R_3$ is $C_1$-$C_6$alkyl, which is substituted by phenylcarbonyl, which phenylcarbonyl in turn can be mono- to polysubstituted by substituents selected from the group consisting of halogen and $C_1$-$C_4$haloalkoxy;
or $R_3$ is $C_1$-$C_6$alkyl, which is substituted by imidazolinyl, which imidazolyl in turn can be mono- to polysubstituted by $C_1$-$C_4$alkyl;
or $R_3$ is $C_1$-$C_6$alkyl, which is substituted by isoxazolyl, which isoxazolyl in turn can be mono- to polysubstituted by halo-substituted phenyl;
or $R_3$ is pyridyl, which in turn can be mono- to polysubstituted by substituents selected from the group consisting of $C_1$-$C_4$alkyl, $C_1$-$C_4$alkoxycarbonyl, phenyl and phenoxy;
or is pyrimidinyl which in turn can be mono- to polysubstituted by substituents selected from the group consisting of hydroxy, $C_1$-$C_4$alkoxy and $C_1$-$C_4$alkyl;
or is piperazinyl, which in turn can be monosubstituted by benzyl;
or is piperidinyl, which in turn can be mono- to polysubstituted by $C_1$-$C_4$alkyl;
or is pyrazolyl, which in turn can be mono- to polysubstituted by substituents selected from the group consisting of $C_1$-$C_4$alkyl, cyano and phenyl;
or is thiethanyl, which can be substituted by $C_1$-$C_4$alkyl;
or is dihydro-thiophene-2-one-3-yl;
or is $C_3$-$C_6$cycloalkyl, which in turn can be mono- to polysubstituted by substituents selected from the group consisting of $C_3$-$C_6$cycloalkyl, $C_2$-$C_6$alkynyl and =N—O—$C_1$-$C_4$haloalkyl;
or is azetidinyl, which in turn can be mono- to polysubstituted by substituents selected from the group consisting of $C_1$-$C_4$haloalkyl and benzyl;
or is pyrrolidinyl which can be substituted by benzyl;
or is $C_1$-$C_6$alkoxycarbonylamino;
or is $C_3$-$C_6$cycloalkenyl which in turn can be mono- to polysubstituted by $C_1$-$C_6$alkoxycarbonyl;
or is phenyl, which in turn can be mono- to polysubstituted by substituents selected from the group consisting of halogen, $C_1$-$C_4$alkyl, $C_1$-$C_4$haloalkyl, $C_1$-$C_4$alkylthio, di($C_1$-$C_4$alkyl)aminosulfonyl, $C_1$-$C_4$alkoxy, phenyl, piperidyl, pyrrolyl, morpholinyl, indolyl, phenylcarbonyl and $C_1$-$C_4$alkoxycarbonyl;
or is quinolinyl, benzothiazolyl or indazolyl;
or is benzothiophenyl, which in turn can be monosubstituted by $C_1$-$C_6$alkoxycarbonyl;
or is thiazolyl, which in turn can be mono- to polysubstituted by substituents selected from the group consisting of $C_1$-$C_4$alkyl, pyridyl, phenyl, pyrimidinyl and $C_1$-$C_4$alkylcarbonyl;
wherein said phenyl can be mono- to polysubstituted by $C_1$-$C_4$alkyl and wherein said pyrimidinyl can be mono- to polysubstituted by $C_1$-$C_4$alkoxy;

or is benzothiazolyl which in turn can be mono- to polysubstituted by $C_1$-$C_4$alkyl;

or is chromen-2-one which in turn can be mono- to polysubstituted by $C_1$-$C_4$alkyl;

or is isoxazolyl, which in turn can be mono- to polysubstituted by substituents selected from the group consisting of $C_1$-$C_4$alkyl and phenyl;

or is thiadiazolyl, which in turn can be monosubstituted by substituents selected from the group consisting of $C_1$-$C_4$alkyl and halo-substituted phenyl;

or is furyl which in turn can be mono- to polysubstituted by substituents selected from the group consisting of cyano and phenyl;

or is pyrazolopyridinyl which in turn can be mono- to polysubstituted by $C_1$-$C_4$alkyl; or is thienyl which in turn can be mono- to polysubstituted by $C_1$-$C_4$alkoxycarbonyl;

or is thietanyloxide, thiethanyldioxide, bicyclo[2.2.1]heptyl or tetrahydrothienyl;

or is isoxazolidin-3-one, which can be monosubstituted by substituents selected from $C_1$-$C_4$alkyl and $C_1$-$C_4$haloalkyl;

or $R_3$ and $R_4$ form together with the nitrogen atom to which they are bonded a 3-6 membered saturated ring which can be mono- to polysubstituted by substituents selected from the group consisting of $C_1$-$C_4$alkyl, $C_1$-$C_4$alkoxy and halogen; and further mono- to polysubstituted by substituents selected from the group consisting of phenylcarbonyl, phenoxy-$C_1$-$C_4$alkyl and phenoxy, which both in turn can be mono- to polysubstituted by halogen; and said ring can be additionally substituted by an ethylene chain; and $R_4$ is hydrogen, $C_1$-$C_6$alkyl, $C_1$-$C_6$haloalkyl or $C_3$-$C_6$cycloalkyl; with the exception of 2-[6-(4-chloro-2-pyridin-3-yl-thiazol-5-yl)-pyridin-2-yl]-pyrimidine and 5-chloro-2-[6-(4-chloro-2-pyridin-3-yl-thiazol-5-yl)-pyridin-2-yl]-pyrimidine; and agrochemically acceptable salts/isomers/enantiomers/tautomers/N-oxides of those compounds.

Compounds of formula I which have at least one basic centre can form, for example, acid addition salts, for example with strong inorganic acids such as mineral acids, for example perchloric acid, sulphuric acid, nitric acid, nitrose acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethyl-propylamine, or a mono-, di- or trihydroxy-lower-alkylamine, for example mono-, di- or triethanolamine.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, nonyl, decyl and their branched isomers. Alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Alkoxy groups preferably have a preferred chain length of from 1 to 6 carbon atoms. Alkoxy is, for example, methoxy, ethoxy, propoxy, i-propoxy, n-butoxy, isobutoxy, sec-butoxy and tert-butoxy and also the isomeric pentyloxy and hexyloxy radicals; preferably methoxy and ethoxy.

Alkoxycarbonyl is, for example, methoxycarbonyl, ethoxycarbonyl, propoxycarbonyl, isopropoxycarbonyl, n-butoxycarbonyl, isobutoxycarbonyl, sec-butoxycarbonyl or tert-butoxycarbonyl; preferably methoxycarbonyl or ethoxycarbonyl. Haloalkoxy groups preferably have a chain length of from 1 to 6 carbon atoms. Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy.

Alkylthio groups preferably have a chain length of from 1 to 6 carbon atoms. Alkylthio is, for example, methylthio, ethylthio, propylthio, isopropylthio, n-butylthio, isobutylthio, sec-butylthio or tert-butylthio, preferably methylthio and ethylthio. Alkylsulphinyl is, for example, methylsulphinyl, ethylsulphinyl, propylsulphinyl, isopropylsulphinyl, n-butylsulphinyl, isobutylsulphinyl, sec-butylsulphinyl, tert-butylsulphinyl; preferably methylsulphinyl and ethylsulphinyl.

Alkylsulphonyl is, for example, methylsulphonyl, ethylsulphonyl, propylsulphonyl, isopropylsulphonyl, n-butylsulphonyl, isobutylsulphonyl, sec-butylsulphonyl or tert-butylsulphonyl; preferably methylsulphonyl or ethylsulphonyl.

Alkylamino is, for example, methylamino, ethylamino, n-propylamino, isopropylamino or the isomeric butylamines. Dialkylamino is, for example, dimethylamino, methylethylamino, diethylamino, n-propylmethylamino, dibutylamino and diisopropylamino. Preference is given to alkylamino groups having a chain length of from 1 to 4 carbon atoms.

Alkoxyalkyl groups preferably have a chain length of 1 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

The cycloalkyl groups preferably have from 3 to 6 ring carbon atoms, for example cyclopropyl, cyclobutyl, cyclopentyl and cyclohexyl. Phenyl, also as part of a substituent such as phenoxy, benzyl, benzyloxy, benzoyl, phenylthio, phenylalkyl, phenoxyalkyl, may be substituted. In this case, the substituents can be in ortho, meta and/or para position. The preferred substituent positions are the ortho and para positions to the ring attachment point.

In the context of the present invention "mono- to polysubstituted" in the definition of the substituents, means typically, depending on the chemical structure of the substituents, monosubstituted to seven-times substituted, preferably monosubstituted to five-times substituted, more preferably mono-, double- or triple-substituted.

In the context of the present invention "halo-substituted phenyl" in the definition of the substituents, means for example a phenyl group which is mono- to polysubstituted by substituents selected from the group consisting of fluoro, chloro, bromo and iodo. Preferably "halo-substituted phenyl" is phenyl which is mono- di or tri-substituted by chloro, in particular mono-substituted by chloro.

According to the present invention, a five- to ten-membered monocyclic or fused bicyclic ring system which may be aromatic, partially saturated or fully saturated is, depending of the number of ring members, for example, selected from the group consisting of

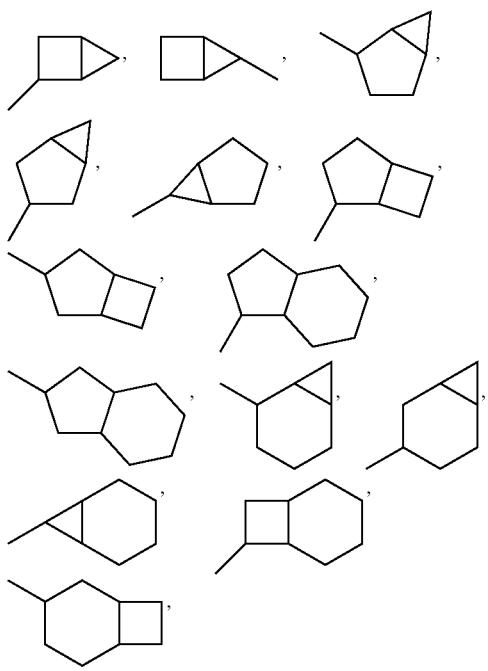

cyclopentyl, cyclohexyl, where said cycloalkyl groups for their part may be preferably unsubstituted or substituted by $C_1$-$C_6$alkyl or halogen, or is phenyl, benzyl, naphthyl or the following heterocyclic groups: pyrrolyl; pyridyl; pyrazolyl; pyrimidyl; pyrazinyl; imidazolyl; thiadiazolyl; quinazolinyl; furyl; oxadiazolyl; indolizinyl; pyranyl; isobenzofuranyl; thienyl; naphthyridinyl; (1-methyl-1H-pyrazol-3-yl)-; (1-ethyl-1H-pyrazol-3-yl)-; (1-propyl-1H-pyrazol-3-yl)-; (1H-pyrazol-3-yl)-; (1,5-dimethyl-1H-pyrazol-3-yl)-; (4-chloro-1-methyl-1H-pyrazol-3-yl)-; (1H-pyrazol-1-yl)-; (3-methyl-1H-pyrazol-1-yl)-; (3,5-dimethyl-1H-pyrazol-1-yl)-; (3-isoxazolyl)-; (5-methyl-3-isoxazolyl)-; (3-methyl-5-isoxazolyl)-; (5-isoxazolyl)-; (1H-pyrrol-2-yl)-; (1-methyl-1H-pyrrol-2-yl)-; (1H-pyrrol-1-yl)-; (1-methyl-1H-pyrrol-3-yl)-; (2-furanyl)-; (5-methyl-2-furanyl)-; (3-furanyl)-; (5-methyl-2-thienyl)-; (2-thienyl)-; (3-thienyl)-; (1-methyl-1H-imidazol-2-yl)-; (1H-imidazol-2-yl)-; (1-methyl-1H-imidazol-4-yl)-; (1-methyl-1H-imidazol-5-yl)-; (4-methyl-2-oxazolyl)-; (5-methyl-2-oxazolyl)-; (2-oxazolyl)-; (2-methyl-5-oxazolyl)-; (2-methyl-4-oxazolyl)-; (4-methyl-2-thiazolyl)-; (5-methyl-2-thiazolyl)-; (2-thiazolyl)-; (2-methyl-5-thiazolyl)-; (2-methyl-4-thiazolyl)-; (3-methyl-4-isothiazolyl)-; (3-methyl-5-isothiazolyl)-; (5-methyl-3-isothiazolyl)-; (1-methyl-1H-1,2,3-triazol-4-yl)-; (2-methyl-2H-1,2,3-triazol-4-yl)-; (4-methyl-2H-1,2,3-triazol-2-yl)-; (1-methyl-1H-1,2,4-triazol-3-yl)-; (1,5-dimethyl-1H-1,2,4-triazol-3-yl)-; (3-methyl-1H-1,2,4-triazol-1-yl)-; (5-methyl-1H-1,2,4-triazol-1-yl)-; (4,5-dimethyl-4H-1,2,4-triazol-3-yl)-; (4-methyl-4H-1,2,4-triazol-3-yl)-; (4H-1,2,4-triazol-4-yl)-; (5-methyl-1,2,3-oxadiazol-4-yl)-; (1,2,3-oxadiazol-4-yl)-; (3-methyl-1,2,4-oxadiazol-5-yl)-; (5-methyl-1,2,4-oxadiazol-3-yl)-; (4-methyl-3-furazanyl)-; (3-furazanyl)-; (5-methyl-1,2,4-oxadiazol-2-yl)-; (5-methyl-1,2,3-thiadiazol-4-yl)-; (1,2,3-thiadiazol-4-yl)-; (3-methyl-1,2,4-thiadiazol-5-yl)-; (5-methyl-1,2,4-thiadiazol-3-yl)-; (4-methyl-1,2,5-thiadiazol-3-yl)-; (5-methyl-1,3,4-thiadiazol-2-yl)-; (1-methyl-1H-tetrazol-5-yl)-; (1H-tetrazol-5-yl)-; (5-methyl-1H-tetrazol-1-yl)-; (2-methyl-2H-tetrazol-5-yl)-; (2-ethyl-2H-tetrazol-5-yl)-; (5-methyl-2H-tetrazol-2-yl)-; (2H-tetrazol-2-yl)-; (2-pyridyl)-; (6-methyl-2-pyridyl)-; (4-pyridyl)-; (3-pyridyl)-; (6-methyl-3-pyridazinyl)-; (5-methyl-3-pyridazinyl)-; (3-pyridazinyl)-; (4,6-dimethyl-2-pyrimidinyl)-; (4-methyl-2-pyrimidinyl)-; (2-pyrimidinyl)-; (2-methyl-4-pyrimidinyl)-; (2-chloro-4-pyrimidinyl)-; (2,6-dimethyl-4-pyrimidinyl)-; (4-pyrimidinyl)-; (2-methyl-5-pyrimidinyl)-; (6-methyl-2-pyrazinyl)-; (2-pyrazinyl)-; (4,6-dimethyl-1,3,5-triazin-2-yl)-; (4,6-dichloro-1,3,5-triazin-2-yl)-; (1,3,5-triazin-2-yl)-; (4-methyl-1,3,5-triazin-2-yl)-; (3-methyl-1,2,4-triazin-5-yl)-; (3-methyl-1,2,4-triazin-6-yl)-;

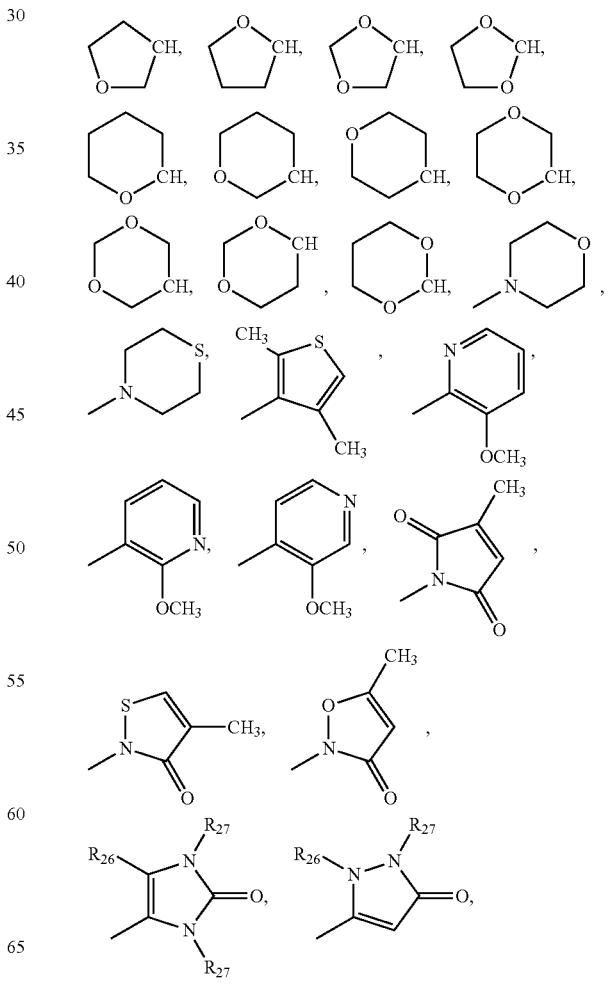

-continued

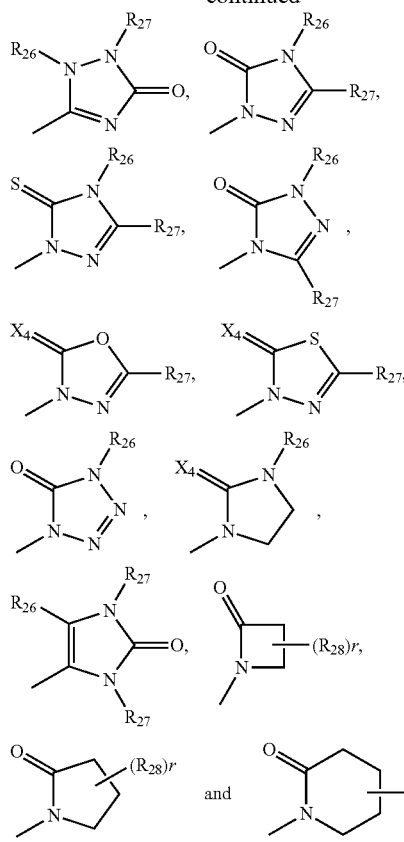

wherein each $R_{26}$ is methyl, each $R_{27}$ and each $R_{28}$ are independently hydrogen, $C_1$-$C_3$alkyl, $C_1$-$C_3$alkoxy, $C_1$-$C_3$alkylthio or trifluoromethyl, $X_4$ is oxygen or sulfur and r=1, 2, 3 or 4. Where no free valency is indicated in those definitions, for example as in

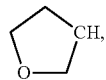

the linkage site is located at the carbon atom labelled "CH" or in a case such as, for example,

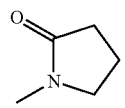

at the bonding site indicated at the bottom left.

In preferred compounds of formula I,
$R_2$ is selected from the group consisting of J-1 to J-24

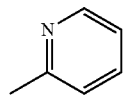
J-1

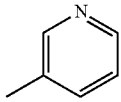
J-2

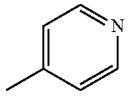
J-3

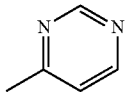
J-4

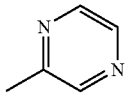
J-5

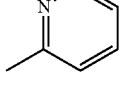
J-6

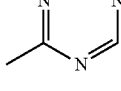
J-7

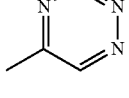
J-8

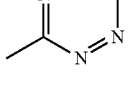
J-9

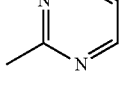
J-10

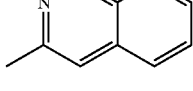
J-11

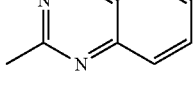
J-12

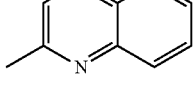
J-13

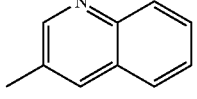
J-14

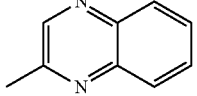
J-15

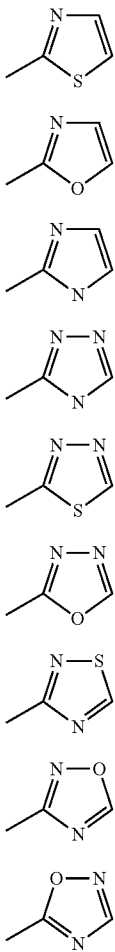

wherein each group J-1 to J-24 is mono- di- or trisubstituted with Rx, wherein
Rx is halogen, $C_1$-$C_6$alkyl, $C_1$-$C_6$alkoxy, $C_1$-$C_6$alkylthio, $C_1$-$C_6$alkylamino, $C_1$-$C_6$di-alkylamino, $C_1$-$C_6$alkoxycarbonylamino, pyrimidinyl, thiazolyl, pyridinyl, pyrazinyl, pyridazinyl, pyrazinyloxy, imidazolyl and oxazolyl, wherein said pyrimidinyl thiazolyl, pyridinyl, pyridazinyl, pyrazinyl, pyrazinyloxy, imidazolyl and oxazolyl in turn can be mono- to polysubstituted by substituents independently selected from the group consisting of halogen, $C_1$-$C_6$alkyl, di-$C_1$-$C_4$alkyl-phosphinoylmethylaminocarbonyl, $C_1$-$C_6$alkoxycarbonylamino, $C_1$-$C_6$alkoxy, $C_1$-$C_6$alkylthio, $C_1$-$C_6$alkylamino, $C_1$-$C_6$di-alkylamino, pyridinyl, pyrimidinyl, pyrazinyloxy and oxazolyl, which pyridinyl, pyrimidinyl, pyrazinyloxy and oxazolyl in turn can be mono- to polysubstituted by substituents independently selected from the group consisting of halogen, $C_1$-$C_6$alkyl and $C_1$-$C_6$alkoxy; or
$R_2$ is a group —C(O)N($R_3$)$R_4$; wherein
$R_3$ is hydrogen, $C_1$-$C_6$alkyl, which can be mono- to polysubstituted by substituents selected from the group consisting of $C_3$-$C_6$cycloalkyl, $C_1$-$C_6$alkylthio, $C_1$-$C_6$haloalkyl, $C_1$-$C_6$alkylsulfinyl, halogen, cyano, hydroxy, $C_1$-$C_6$alkoxy, $C_2$-$C_6$alkenyl, $C_2$-$C_6$alkynyl, $C_1$-$C_6$alkoxy-$C_3$-$C_6$alkynyl, oxolanyl, dioxolanyl, thienyl, thietanyl, thiethanyloxide, thiethanyldioxide, di-$C_1$-$C_4$alkyl-phosphinoylmethyl, 1-H-benzoimidazol-2-yl, benzo[1,3]dioxolyl, morpholinyl, piperidinyl, pyrimidinyl, pyrrolidinyl, benzylthio, 2,3-dihydro-benzo[1,4]dioxinyl, 1H-indolyl, furyl, —C=N—O—$C_1$-$C_6$alkyl, $C_1$-$C_6$alkylcarbonylamino, phenoxy and phenyl, said phenyl in turn can be mono- to polysubstituted by substituents selected from the group consisting of hydroxy, halogen, $C_1$-$C_6$alkoxy, $C_1$-$C_6$haloalkoxy, pyrazolyl, piperidinyl, phenoxy and $C_1$-$C_4$alkylsulfonyl;
or $R_3$ is $C_1$-$C_6$alkyl, which is substituted by pyridyl, which pyridyl in turn can be mono- to polysubstituted by substituents selected from the group consisting of halogen and $C_1$-$C_4$haloalkyl;
or $R_3$ is $C_1$-$C_6$alkyl, which is substituted by phenoxy, which phenoxy in turn can be mono- to polysubstituted by substituents selected from the group consisting of halogen and $C_1$-$C_4$alkyl;
or $R_3$ is $C_1$-$C_6$alkyl, which is substituted by phenylcarbonyl, which phenylcarbonyl in turn can be mono- to polysubstituted by substituents selected from the group consisting of halogen and $C_1$-$C_4$haloalkoxy;
or $R_3$ is $C_1$-$C_6$alkyl, which is substituted by imidazolinyl, which imidazolyl in turn can be mono- to polysubstituted by $C_1$-$C_4$alkyl;
or $R_3$ is $C_1$-$C_6$alkyl, which is substituted by isoxazolyl, which isoxazolyl in turn can be mono- to polysubstituted by halo-substituted phenyl;
or $R_3$ is pyridyl, which in turn can be mono- to polysubstituted by substituents selected from the group consisting of $C_1$-$C_4$alkyl, $C_1$-$C_4$alkoxycarbonyl, phenyl and phenoxy;
or is pyrimidinyl which in turn can be mono- to polysubstituted by substituents selected from the group consisting of hydroxy, $C_1$-$C_4$alkoxy and $C_1$-$C_4$alkyl;
or is piperazinyl, which in turn can be monosubstituted by benzyl;
or is piperidinyl, which in turn can be mono- to polysubstituted by $C_1$-$C_4$alkyl;
or is pyrazolyl, which in turn can be mono- to polysubstituted by substituents selected from the group consisting of $C_1$-$C_4$alkyl, cyano and phenyl;
or is thiethanyl, which can be substituted by $C_1$-$C_4$alkyl;
or is dihydro-thiophene-2-one-3-yl;
or is $C_3$-$C_6$cycloalkyl, which in turn can be mono- to polysubstituted by substituents selected from the group consisting of $C_3$-$C_6$cycloalkyl, $C_2$-$C_6$alkynyl and =N—O—$C_1$-$C_4$haloalkyl;
or is azetidinyl, which in turn can be mono- to polysubstituted by substituents selected from the group consisting of $C_1$-$C_4$haloalkyl and benzyl;
or is pyrrolidinyl which can be substituted by benzyl;
or is $C_1$-$C_6$alkoxycarbonylamino;
or is $C_3$-$C_6$cycloalkenyl which in turn can be mono- to polysubstituted by $C_1$-$C_6$alkoxycarbonyl;
or is phenyl, which in turn can be mono- to polysubstituted by substituents selected from the group consisting of halogen, $C_1$-$C_4$alkyl, $C_1$-$C_4$haloalkyl, $C_1$-$C_4$alkylthio, di($C_1$-$C_4$alkyl)aminosulfonyl, $C_1$-$C_4$alkoxy, phenyl, piperidyl, pyrrolyl, morpholinyl, indolyl, phenylcarbonyl and $C_1$-$C_4$alkoxycarbonyl;
or is quinolinyl, benzothiazolyl or indazolyl;
or is benzothiophenyl, which in turn can be monosubstituted by $C_1$-$C_6$alkoxycarbonyl;
or is thiazolyl, which in turn can be mono- to polysubstituted by substituents selected from the group consisting of $C_1$-$C_4$alkyl, pyridyl, phenyl, pyrimidinyl and $C_1$-$C_4$alkylcarbonyl;
wherein said phenyl can be mono- to polysubstituted by $C_1$-$C_4$alkyl and wherein said pyrimidinyl can be mono- to polysubstituted by $C_1$-$C_4$alkoxy;

or is benzothiazolyl which in turn can be mono- to polysubstituted by $C_1$-$C_4$alkyl;

or is chromen-2-one which in turn can be mono- to polysubstituted by $C_1$-$C_4$alkyl;

or is isoxazolyl, which in turn can be mono- to polysubstituted by substituents selected from the group consisting of $C_1$-$C_4$alkyl and phenyl;

or is thiadiazolyl, which in turn can be monosubstituted by substituents selected from the group consisting of $C_1$-$C_4$alkyl and halo-substituted phenyl;

or is furyl which in turn can be mono- to polysubstituted by substituents selected from the group consisting of cyano and phenyl;

or is pyrazolopyridinyl which in turn can be mono- to polysubstituted by $C_1$-$C_4$alkyl; or is thienyl which in turn can be mono- to polysubstituted by $C_1$-$C_4$alkoxycarbonyl;

or is thietanyloxide, thiethanyldioxide, bicyclo[2.2.1]heptyl or tetrahydrothienyl;

or is isoxazolidin-3-one, which can be monosubstituted by substituents selected from $C_1$-$C_4$alkyl and $C_1$-$C_4$haloalkyl;

or $R_3$ and $R_4$ form together with the nitrogen atom to which they are bonded a 3-6 membered saturated ring which can be mono- to polysubstituted by substituents selected from the group consisting of $C_1$-$C_4$alkyl, $C_1$-$C_4$alkoxy and halogen; and further mono- to polysubstituted by substituents selected from the group consisting of phenylcarbonyl, phenoxy-$C_1$-$C_4$alkyl and phenoxy, which both in turn can be mono- to polysubstituted by halogen; and said ring can be additionally substituted by an ethylene chain; and $R_4$ is hydrogen, $C_1$-$C_6$alkyl, $C_1$-$C_6$haloalkyl or $C_3$-$C_6$cycloalkyl.

Preferably J is selected from J-1 and J-4.

In further preferred compounds of formula I, $R_2$ is pyridyl or pyrimidinyl, said pyridyl or pyrimidinyl can be mono- to polysubstituted by substituents selected from the group consisting of pyrimidinyl, halogen and pyridyl, wherein said pyrimidinyl and pyridyl in turn can be mono- to polysubstituted by halogen, $C_1$-$C_6$alkyl, $C_1$-$C_6$haloalkyl, $C_1$-$C_6$alkoxy; or $R_2$ is thiazolyl which can be substituted by substituents selected from the group consisting of halogen, di-$C_1$-$C_4$alkyl-phosphinoylmethyl-aminocarbonyl and $C_1$-$C_6$alkoxycarbonylamino; or $R_2$ is [1,3,4]oxadiazole-2-yl, which can be substituted by pyridinyl which in turn can be substituted by $C_1$-$C_4$alkyl; or $R_2$ is [1,3,4]thiadiazole-2-yl, which can be substituted by pyridinyl which in turn can be substituted by $C_1$-$C_4$alkyl; or $R_2$ is pyrimidinyl which can be mono- to polysubstituted by $C_1$-$C_4$alkoxy; or $R_2$ is pyrazolyl; or $R_2$ is $C_2$-$C_6$alkynyl which is substituted by substituents selected from the group consisting of pyridinyl, pyrazinyloxy and oxazolyl, which oxazolyl in turn can be substituted by $C_1$-$C_6$alkyl;

or $R_2$ is a group —C(O)N($R_3$)$R_4$; wherein $R_3$ is hydrogen, $C_1$-$C_6$alkyl, which can be mono- to polysubstituted by substituents selected from the group consisting of $C_3$-$C_6$cycloalkyl, $C_1$-$C_6$alkylthio, $C_1$-$C_6$haloalkyl, $C_1$-$C_6$alkylsulfinyl, halogen, cyano, hydroxy, $C_1$-$C_6$alkoxy, $C_2$-$C_6$alkenyl, $C_2$-$C_6$alkynyl, $C_1$-$C_6$alkoxy-$C_3$-$C_6$alkynyl, oxolanyl, dioxolanyl, thienyl, thietanyl, thiethanyldioxide, 1-H-benzoimidazol-2-yl, benzo[1,3]dioxolyl, morpholinyl, piperidinyl, pyrimidinyl, pyrrolidinyl, benzylthio, 2,3-dihydro-benzo[1,4]dioxinyl, 1H-indolyl, furyl, —C=N—O—$C_1$-$C_6$alkyl, $C_1$-$C_6$alkylcarbonylamino, phenoxy and phenyl, said phenyl in turn can be mono- to polysubstituted by substituents selected from the group consisting of hydroxy, halogen, $C_1$-$C_6$alkoxy, $C_1$-$C_6$haloalkoxy, pyrazolyl, piperidinyl, phenoxy and $C_1$-$C_4$alkylsulfonyl;

or $R_3$ is $C_1$-$C_6$alkyl, which is substituted by pyridyl, which pyridyl in turn can be mono- to polysubstituted by substituents selected from the group consisting of halogen and $C_1$-$C_4$haloalkyl;

or $R_3$ is $C_1$-$C_6$alkyl, which is substituted by phenoxy, which phenoxy in turn can be mono- to polysubstituted by substituents selected from the group consisting of halogen and $C_1$-$C_4$alkyl;

or $R_3$ is $C_1$-$C_6$alkyl, which is substituted by phenylcarbonyl, which phenylcarbonyl in turn can be mono- to polysubstituted by substituents selected from the group consisting of halogen and $C_1$-$C_4$haloalkoxy;

or $R_3$ is $C_1$-$C_6$alkyl, which is substituted by imidazolinyl, which imidazolyl in turn can be mono- to polysubstituted by $C_1$-$C_4$alkyl;

or $R_3$ is $C_1$-$C_6$alkyl, which is substituted by isoxazolyl, which isoxazolyl in turn can be mono- to polysubstituted by halo-substituted phenyl;

or $R_3$ is pyridyl, which in turn can be mono- to polysubstituted by substituents selected from the group consisting of $C_1$-$C_4$alkyl, $C_1$-$C_4$alkoxycarbonyl, phenyl and phenoxy;

or is pyrimidinyl which in turn can be mono- to polysubstituted by substituents selected from the group consisting of hydroxy, $C_1$-$C_4$alkoxy and $C_1$-$C_4$alkyl;

or is piperazinyl, which in turn can be monosubstituted by benzyl;

or is piperidinyl, which in turn can be mono- to polysubstituted by $C_1$-$C_4$alkyl;

or is pyrazolyl, which in turn can be mono- to polysubstituted by substituents selected from the group consisting of $C_1$-$C_4$alkyl, cyano and phenyl;

or is thiethanyl, which can be substituted by $C_1$-$C_4$alkyl;

or is dihydro-thiophene-2-one-3-yl;

or is $C_3$-$C_6$cycloalkyl, which in turn can be mono- to polysubstituted by substituents selected from the group consisting of $C_3$-$C_6$cycloalkyl, $C_2$-$C_6$alkynyl and =N—O—$C_1$-$C_4$haloalkyl;

or is azetidinyl, which in turn can be mono- to polysubstituted by substituents selected from the group consisting of $C_1$-$C_4$haloalkyl and benzyl;

or is pyrrolidinyl which can be substituted by benzyl;

or is $C_1$-$C_6$alkoxycarbonylamino;

or is $C_3$-$C_6$cycloalkenyl which in turn can be mono- to polysubstituted by $C_1$-$C_6$alkoxycarbonyl;

or is phenyl, which in turn can be mono- to polysubstituted by substituents selected from the group consisting of halogen, $C_1$-$C_4$alkyl, $C_1$-$C_4$haloalkyl, $C_1$-$C_4$alkylthio, di($C_1$-$C_4$alkyl)aminosulfonyl, $C_1$-$C_4$alkoxy, phenyl, piperidyl, pyrrolyl, morpholinyl, indolyl, phenylcarbonyl and $C_1$-$C_4$alkoxycarbonyl;

or is quinolinyl, benzothiazolyl or indazolyl;

or is benzothiophenyl, which in turn can be monosubstituted by $C_1$-$C_6$alkoxycarbonyl;

or is thiazolyl which in turn can be mono- to polysubstituted by substituents selected from the group consisting of $C_1$-$C_4$alkyl, pyridyl, phenyl, pyrimidinyl and $C_1$-$C_4$alkylcarbonyl;

wherein said phenyl can be mono- to polysubstituted by $C_1$-$C_4$alkyl and wherein said pyrimidinyl can be mono- to polysubstituted by $C_1$-$C_4$alkoxy;

or is benzothiazolyl which in turn can be mono- to polysubstituted by $C_1$-$C_4$alkyl;

or is chromen-2-one which in turn can be mono- to polysubstituted by $C_1$-$C_4$alkyl;

or is isoxazolyl, which in turn can be mono- to polysubstituted by substituents selected from the group consisting of $C_1$-$C_4$alkyl and phenyl;
or is thiadiazolyl, which in turn can be monosubstituted by substituents selected from the group consisting of $C_1$-$C_4$alkyl and halo-substituted phenyl;
or is furyl which in turn can be mono- to polysubstituted by substituents selected from the group consisting of cyano and phenyl;
or is pyrazolopyridinyl which in turn can be mono- to polysubstituted by $C_1$-$C_4$alkyl; or is thienyl which in turn can be mono- to polysubstituted by $C_1$-$C_4$alkoxycarbonyl;
or is thietanyloxide, thiethanyldioxide, bicyclo[2.2.1]heptyl or tetrahydrothienyl;
or is isoxazolidin-3-one, which can be monosubstituted by substituents selected from $C_1$-$C_4$alkyl and $C_1$-$C_4$haloalkyl;
or $R_3$ and $R_4$ form together with the nitrogen atom to which they are bonded a 3-6 membered saturated ring which can be mono- to polysubstituted by substituents selected from the group consisting of $C_1$-$C_4$alkyl, $C_1$-$C_4$alkoxy and halogen; and further mono- to polysubstituted by substituents selected from the group consisting of
phenylcarbonyl, phenoxy-$C_1$-$C_4$alkyl and phenoxy, which both in turn can be mono- to polysubstituted by halogen; and said ring can be additionally substituted by an ethylene chain; and
$R_4$ is hydrogen, $C_1$-$C_6$alkyl, $C_1$-$C_6$haloalkyl or $C_3$-$C_6$cycloalkyl.

In especially preferred compounds of formula I,
$R_2$ is pyridyl, said pyridyl can be mono- to polysubstituted by substituents selected from the group consisting of pyrimidinyl, halogen and thiazolyl, wherein said thiazolyl in turn can be mono- to polysubstituted by halogen; or
$R_2$ is thiazolyl which can be substituted by substituents selected from the group consisting of halogen, di-$C_1$-$C_4$alkyl-phosphinoylmethyl-aminocarbonyl and $C_1$-$C_6$alkoxycarbonylamino; or
$R_2$ is [1,3,4]oxadiazole-2-yl, which can be substituted by pyridinyl which in turn can be substituted by $C_1$-$C_4$alkyl; or
$R_2$ is [1,3,4]thiadiazole-2-yl, which can be substituted by pyridinyl which in turn can be substituted by $C_1$-$C_4$alkyl; or
$R_2$ is pyrimidinyl which can be mono- to polysubstituted by $C_1$-$C_4$alkoxy; or
$R_2$ is pyrazolyl; or
$R_2$ is $C_2$-$C_6$alkynyl which is substituted by substituents selected from the group consisting of pyridinyl, pyrazinyloxy and oxazolyl, which oxazolyl in turn can be substituted by $C_1$-$C_6$alkyl;
or
$R_2$ is pyridylcarbonylamino, which can be substituted by $C_1$-$C_4$alkyl; or
$R_2$ is a group —C(O)N($R_3$)$R_4$; wherein
$R_3$ is hydrogen, $C_1$-$C_6$alkyl, which can be mono- to polysubstituted by substituents selected from the group consisting of $C_3$-$C_6$cycloalkyl, $C_1$-$C_6$alkylthio, $C_1$-$C_6$haloalkyl, $C_1$-$C_6$alkylsulfinyl, halogen, cyano, hydroxy, $C_1$-$C_6$alkoxy, $C_2$-$C_6$alkenyl, $C_2$-$C_6$alkynyl, $C_1$-$C_6$alkoxy-$C_3$-$C_6$alkynyl, oxolanyl, dioxolanyl, thienyl, thietanyl, thiethanyldioxide, 1-H-benzoimidazol-2-yl, benzo[1,3]dioxolyl, morpholinyl, piperidinyl, pyrimidinyl, pyrrolidinyl, benzylthio, 2,3-dihydro-benzo[1,4]dioxinyl, 1H-indolyl, furyl, —C=N—O—$C_1$-$C_6$alkyl, $C_1$-$C_6$alkylcarbonylamino, phenoxy and phenyl, said phenyl can be mono- to polysubstituted by substituents selected from the group consisting of hydroxy, halogen, $C_1$-$C_6$alkoxy, $C_1$-$C_6$haloalkoxy, pyrazolyl, piperidinyl, phenoxy and $C_1$-$C_4$alkylsulfonyl;
or $R_3$ is $C_1$-$C_6$alkyl, which is substituted by pyridyl, which pyridyl in turn can be mono- to polysubstituted by substituents selected from the group consisting of halogen and $C_1$-$C_4$haloalkyl;
or $R_3$ is $C_1$-$C_6$alkyl, which is substituted by phenoxy, which phenoxy in turn can be mono- to polysubstituted by substituents selected from the group consisting of halogen and $C_1$-$C_4$alkyl;
or $R_3$ is $C_1$-$C_6$alkyl, which is substituted by phenylcarbonyl, which phenylcarbonyl in turn can be mono- to polysubstituted by substituents selected from the group consisting of halogen and $C_1$-$C_4$haloalkoxy;
or $R_3$ is $C_1$-$C_6$alkyl, which is substituted by imidazolinyl, which imidazolyl in turn can be mono- to polysubstituted by $C_1$-$C_4$alkyl;
or $R_3$ is $C_1$-$C_6$alkyl, which is substituted by isoxazolyl, which isoxazolyl in turn can be mono- to polysubstituted by halo-substituted phenyl;
or $R_3$ is pyridyl, which in turn can be mono- to polysubstituted by substituents selected from the group consisting of $C_1$-$C_4$alkyl, $C_1$-$C_4$alkoxycarbonyl, phenyl and phenoxy;
or is pyrimidinyl which in turn can be mono- to polysubstituted by substituents selected from the group consisting of hydroxy, $C_1$-$C_4$alkoxy and $C_1$-$C_4$alkyl;
or is piperazinyl, which in turn can be monosubstituted by benzyl;
or is piperidinyl, which in turn can be mono- to polysubstituted by $C_1$-$C_4$alkyl;
or is pyrazolyl, which in turn can be mono- to polysubstituted by substituents selected from the group consisting of $C_1$-$C_4$alkyl, cyano and phenyl;
or is thiethanyl, which can be substituted by $C_1$-$C_4$alkyl;
or is dihydro-thiophene-2-one-3-yl;
or is $C_3$-$C_6$cycloalkyl, which in turn can be mono- to polysubstituted by substituents selected from the group consisting of $C_3$-$C_6$cycloalkyl, $C_2$-$C_6$alkynyl and =N—O—$C_1$-$C_4$haloalkyl;
or is azetidinyl, which in turn can be mono- to polysubstituted by substituents selected from the group consisting of $C_1$-$C_4$haloalkyl and benzyl;
or is pyrrolidinyl which can be substituted by benzyl;
or is $C_1$-$C_6$alkoxycarbonylamino;
or is $C_3$-$C_6$cycloalkenyl which in turn can be mono- to polysubstituted by $C_1$-$C_6$alkoxycarbonyl;
or is phenyl, which in turn can be mono- to polysubstituted by substituents selected from the group consisting of halogen, $C_1$-$C_4$alkyl, $C_1$-$C_4$haloalkyl, $C_1$-$C_4$alkylthio, di($C_1$-$C_4$alkyl)aminosulfonyl, $C_1$-$C_4$alkoxy, phenyl, piperidyl, pyrrolyl, morpholinyl, indolyl, phenylcarbonyl and $C_1$-$C_4$alkoxycarbonyl;
or is quinolinyl, benzothiazolyl or indazolyl;
or is benzothiophenyl, which in turn can be monosubstituted by $C_1$-$C_6$alkoxycarbonyl;
or is thiazolyl, which in turn can be mono- to polysubstituted by substituents selected from the group consisting of $C_1$-$C_4$alkyl, pyridyl, phenyl, pyrimidinyl and $C_1$-$C_4$alkylcarbonyl;
wherein said phenyl can be mono- to polysubstituted by $C_1$-$C_4$alkyl and wherein said pyrimidinyl can be mono- to polysubstituted by $C_1$-$C_4$alkoxy;
or is benzothiazolyl which in turn can be mono- to polysubstituted by $C_1$-$C_4$alkyl;
or is chromen-2-one which in turn can be mono- to polysubstituted by $C_1$-$C_4$alkyl;
or is isoxazolyl, which in turn can be mono- to polysubstituted by substituents selected from the group consisting of $C_1$-$C_4$alkyl and phenyl;

or is thiadiazolyl, which in turn can be monosubstituted by substituents selected from the group consisting of $C_1$-$C_4$alkyl and halo-substituted phenyl;
or is furyl which in turn can be mono- to polysubstituted by substituents selected from the group consisting of cyano and phenyl;
or is pyrazolopyridinyl which in turn can be mono- to polysubstituted by $C_1$-$C_4$alkyl; or is thienyl which in turn can be mono- to polysubstituted by $C_1$-$C_4$alkoxycarbonyl; or is thietanyloxide, thiethanyldioxide, bicyclo[2.2.1]heptyl or tetrahydrothienyl;
or is isoxazolidin-3-one, which can be monosubstituted by substituents selected from $C_1$-$C_4$alkyl and $C_1$-$C_4$haloalkyl;
or $R_3$ and $R_4$ form together with the nitrogen atom to which they are bonded a 3-6 membered saturated ring which can be mono- to polysubstituted by substituents selected from the group consisting of $C_1$-$C_4$alkyl, $C_1$-$C_4$alkoxy and halogen; and further mono- to polysubstituted by substituents selected from the group consisting of
phenylcarbonyl, phenoxy-$C_1$-$C_4$alkyl and phenoxy, which both in turn can be mono- to polysubstituted by halogen; and said ring can be additionally substituted by an ethylene chain; and
$R_4$ is hydrogen, $C_1$-$C_6$alkyl, $C_1$-$C_6$haloalkyl or $C_3$-$C_6$cycloalkyl.

Further preferred are compounds of formula I, wherein $R_2$ is pyridyl, said pyridyl can be mono- to polysubstituted by substituents selected from the group consisting of pyrimidinyl, halogen and pyrimidinyl and pyridyl, wherein said pyrimidinyl and pyridyl in turn can be mono- to polysubstituted by halogen, $C_1$-$C_6$alkyl, $C_1$-$C_6$haloalkyl, $C_1$-$C_6$alkoxy; or
$R_2$ is thiazolyl which can be substituted by substituents selected from the group consisting of halogen, di-$C_1$-$C_4$alkyl-phosphinoylmethyl-aminocarbonyl and $C_1$-$C_6$alkoxycarbonylamino; or
$R_2$ is [1,3,4]oxadiazole-2-yl, which can be substituted by pyridinyl which in turn can be substituted by $C_1$-$C_4$alkyl; or
$R_2$ is [1,3,4]thiadiazole-2-yl, which can be substituted by pyridinyl which in turn can be substituted by $C_1$-$C_4$alkyl; or
$R_2$ is pyrimidinyl which can be mono- to polysubstituted by $C_1$-$C_4$alkoxy; or
$R_2$ is pyrazolyl; or
$R_2$ is $C_2$-$C_6$alkynyl which is substituted by substituents selected from the group consisting of pyridinyl, pyraziny-loxy and oxazolyl, which oxazolyl in turn can be substituted by $C_1$-$C_6$alkyl; or
$R_2$ is a group —C(O)N($R_3$)$R_4$; wherein
$R_3$ is hydrogen, $C_1$-$C_6$alkyl, which can be mono- to polysubstituted by substituents selected from the group consisting of $C_3$-$C_6$cycloalkyl, $C_1$-$C_6$alkylthio, $C_1$-$C_6$haloalkyl, $C_1$-$C_6$alkylsulfinyl, halogen, cyano, hydroxy, $C_1$-$C_6$alkoxy, $C_2$-$C_6$alkenyl, $C_2$-$C_6$alkynyl, $C_1$-$C_6$alkoxy-$C_3$-$C_6$alkynyl, oxolanyl, dioxolanyl, thienyl, thietanyl, thiethanyldioxide, 1-H-benzoimidazol-2-yl, benzo[1,3]dioxolyl, morpholinyl, piperidinyl, pyrimidinyl, pyrrolidinyl, benzylthio, 2,3-di-hydro-benzo[1,4]dioxinyl, 1H-indolyl, furyl, —C═N—O—$C_1$-$C_6$alkyl, $C_1$-$C_6$alkylcarbonylamino and phenyl, said phenyl in turn can be mono- to polysubstituted by substituents selected from the group consisting of hydroxy, halogen, $C_1$-$C_6$alkoxy, $C_1$-$C_6$haloalkoxy, pyrazolyl, piperidinyl, phenoxy and $C_1$-$C_4$alkylsulfonyl;
or $R_3$ is $C_1$-$C_6$alkyl, which is substituted by pyridyl, which pyridyl in turn can be mono- to polysubstituted by substituents selected from the group consisting of halogen and $C_1$-$C_4$haloalkyl;

or $R_3$ is $C_1$-$C_6$alkyl, which is substituted by phenoxy, which phenoxy in turn can be mono- to polysubstituted by substituents selected from the group consisting of halogen and $C_1$-$C_4$alkyl;
or $R_3$ is $C_1$-$C_6$alkyl, which is substituted by phenylcarbonyl, which phenylcarbonyl in turn can be mono- to polysubstituted by substituents selected from the group consisting of halogen and $C_1$-$C_4$haloalkoxy;
or $R_3$ is $C_1$-$C_6$alkyl, which is substituted by imidazolinyl, which imidazolyl in turn can be mono- to polysubstituted by $C_1$-$C_4$alkyl;
or $R_3$ is $C_1$-$C_6$alkyl, which is substituted by isoxazolyl, which isoxazolyl in turn can be mono- to polysubstituted by halo-substituted phenyl;
or $R_3$ is pyridyl, which in turn can be mono- to polysubstituted by substituents selected from the group consisting of $C_1$-$C_4$alkyl, $C_1$-$C_4$alkoxycarbonyl, phenyl and phenoxy;
or is pyrimidinyl which in turn can be mono- to polysubstituted by substituents selected from the group consisting of hydroxy and $C_1$-$C_4$alkyl;
or is piperazinyl, which in turn can be monosubstituted by benzyl;
or is piperidinyl, which in turn can be mono- to polysubstituted by $C_1$-$C_4$alkyl;
or is pyrazolyl, which in turn can be mono- to polysubstituted by substituents selected from the group consisting of $C_1$-$C_4$alkyl, cyano and phenyl;
or is thiethanyl, which can be substituted by $C_1$-$C_4$alkyl;
or is dihydro-thiophene-2-one-3-yl;
or is $C_3$-$C_6$cycloalkyl, which in turn can be mono- to polysubstituted by substituents selected from the group consisting of $C_3$-$C_6$cycloalkyl, $C_2$-$C_6$alkynyl and ═N—O—$C_1$-$C_4$haloalkyl;
or is azetidinyl, which in turn can be mono- to polysubstituted by substituents selected from the group consisting of $C_1$-$C_4$haloalkyl and benzyl;
or is pyrrolidinyl which can be substituted by benzyl;
or is $C_3$-$C_6$cycloalkenyl which in turn can be mono- to polysubstituted by $C_1$-$C_6$alkoxycarbonyl;
or is phenyl, which in turn can be mono- to polysubstituted by substituents selected from the group consisting of halogen, $C_1$-$C_4$alkyl, $C_1$-$C_4$haloalkyl, $C_1$-$C_4$alkylthio, di($C_1$-$C_4$alkyl)aminosulfonyl, $C_1$-$C_4$alkoxy, phenyl, piperidyl, pyrrolyl, morpholinyl, indolyl, phenylcarbonyl and $C_1$-$C_4$alkoxycarbonyl;
or is quinolinyl, benzothiazolyl or indazolyl;
or is benzothiophenyl, which in turn can be monosubstituted by $C_1$-$C_6$alkoxycarbonyl;
or is thiazolyl, which in turn can be mono- to polysubstituted by substituents selected from the group consisting of $C_1$-$C_4$alkyl, pyridyl, phenyl, pyrimidinyl and $C_1$-$C_4$alkylcarbonyl;
wherein said phenyl can be mono- to polysubstituted by $C_1$-$C_4$alkyl and wherein said pyrimidinyl can be mono- to polysubstituted by $C_1$-$C_4$alkoxy;
or is benzothiazolyl which in turn can be mono- to polysubstituted by $C_1$-$C_4$alkyl;
or is chromen-2-one which in turn can be mono- to polysubstituted by $C_1$-$C_4$alkyl;
or is isoxazolyl, which in turn can be mono- to polysubstituted by substistents selected from the group consisting of $C_1$-$C_4$alkyl and phenyl;
or is thiadiazolyl, which in turn can be monosubstituted by substituents selected from the group consisting of $C_1$-$C_4$alkyl and halo-substituted phenyl;

or is furyl which in turn can be mono- to polysubstituted by substituents selected from the group consisting of cyano and phenyl;

or is pyrazolopyridinyl which in turn can be mono- to polysubstituted by $C_1$-$C_4$alkyl; or is thienyl which in turn can be mono- to polysubstituted by $C_1$-$C_4$alkoxycarbonyl; or is thietanyloxide, thiethanyldioxide, bicyclo[2.2.1]heptyl or tetrahydrothienyl;

or is isoxazolidin-3-one, which can be monosubstituted by substituents selected from $C_1$-$C_4$alkyl and $C_1$-$C_4$haloalkyl;

or $R_3$ and $R_4$ form together with the nitrogen atom to which they are bonded a 3-6 membered saturated ring which can be mono- to polysubstituted by substituents selected from the group consisting of $C_1$-$C_4$alkyl, $C_1$-$C_4$alkoxy and halogen; and further mono- to polysubstituted by substituents selected from the group consisting of
phenylcarbonyl, phenoxy-$C_1$-$C_4$alkyl and phenoxy, which both in turn can be mono- to polysubstituted by halogen; and said ring can be additionally substituted by an ethylene chain; and $R_4$ is hydrogen, $C_1$-$C_6$alkyl, $C_1$-$C_6$haloalkyl or $C_3$-$C_6$cycloalkyl.

In said especially preferred compounds of formula I, $R_2$ is a group —C(O)N($R_3$)$R_4$.

In said especially preferred compounds of formula I, $R_2$ is pyridine substituted by substituents independently selected from halogen or pyrimidinyl;

or $R_2$ is a group —C(O)N($R_3$)$R_4$; wherein $R_3$ is thiethanyl, which can be substituted by $C_1$-$C_4$alkyl; or is thiethanyldioxide, thietanyloxide or tetrahydrothienyl; or is $C_1$-$C_6$alkyl substituted by substituents selected from the group consisting of $C_2$-$C_6$alkynyl, $C_1$-$C_6$alkylthio, $C_1$-$C_6$alkylcarbonylamino, $C_1$-$C_6$haloalkyl, thienyl, thietanyl and thiethanyldioxide;

and $R_4$ is hydrogen. In particular $R_3$ is thiethanyl, which can be substituted by $C_1$-$C_4$alkyl; or is thiethanyldioxide, thietanyloxide or tetrahydrothienyl; or is $C_1$-$C_6$alkyl substituted by $C_1$-$C_6$alkylthio, thienyl, thietanyl and thiethanyldioxide.

In a preferred group of compounds of formula I, the substituents are defined as follows $R_2$ is selected from the group consisting of J-1 to J-24

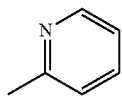
J-1

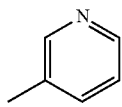
J-2

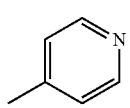
J-3

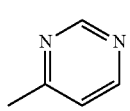
J-4

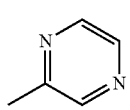
J-5

-continued

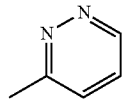
J-6

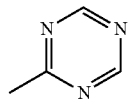
J-7

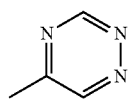
J-8

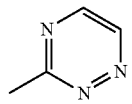
J-9

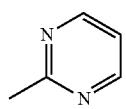
J-10

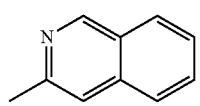
J-11

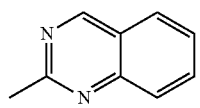
J-12

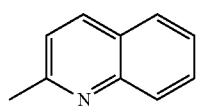
J-13

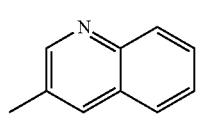
J-14

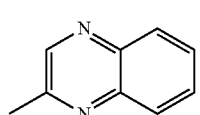
J-15

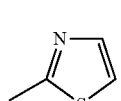
J-16

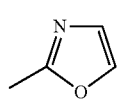
J-17

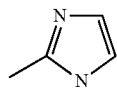
J-18

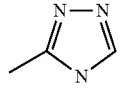
J-19

-continued

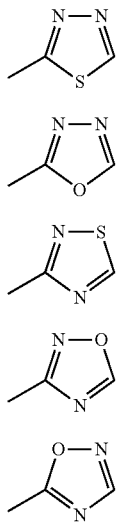

J-20

J-21

J-22

J-23

J-24 wherein each group J-1 to J-24 is mono- di- or trisubstituted with Rx, wherein
Rx is halogen, $C_1$-$C_6$alkyl, $C_1$-$C_6$alkoxy, $C_1$-$C_6$alkylthio, $C_1$-$C_6$alkylamino, $C_1$-$C_6$di-alkylamino or $C_1$-$C_6$alkoxycarbonylamino; or
$R_2$ is a group —C(O)N($R_3$)$R_4$; wherein
$R_3$ is hydrogen, $C_1$-$C_6$alkyl, which can be mono- to polysubstituted by substituents selected from the group consisting of $C_3$-$C_6$cycloalkyl, $C_1$-$C_6$alkylthio, $C_1$-$C_6$haloalkyl, $C_1$-$C_6$alkylsulfinyl, halogen, cyano, hydroxy, $C_1$-$C_6$alkoxy, $C_2$-$C_6$alkenyl, $C_2$-$C_6$alkynyl, $C_1$-$C_6$alkoxy-$C_3$-$C_6$alkynyl, oxolanyl, dioxolanyl, thienyl, thietanyl, thiethanyloxide, thiethanyldioxide, di-$C_1$-$C_4$alkyl-phosphinoylmethyl, 1-H-benzoimidazol-2-yl, benzo[1,3]dioxolyl, morpholinyl, piperidinyl, pyrimidinyl, pyrrolidinyl, benzylthio, 2,3-dihydrobenzo[1,4]dioxinyl, 1H-indolyl, furyl, —C=N—O—$C_1$-$C_6$alkyl, $C_1$-$C_6$alkylcarbonylamino, phenoxy and phenyl, said phenyl in turn can be mono- to polysubstituted by substituents selected from the group consisting of hydroxy, halogen, $C_1$-$C_6$alkoxy, $C_1$-$C_6$haloalkoxy, pyrazolyl, piperidinyl, phenoxy and $C_1$-$C_4$alkylsulfonyl;
or $R_3$ is $C_1$-$C_6$alkyl, which is substituted by pyridyl, which pyridyl in turn can be mono- to polysubstituted by substituents selected from the group consisting of halogen and $C_1$-$C_4$haloalkyl;
or $R_3$ is $C_1$-$C_6$alkyl, which is substituted by phenoxy, which phenoxy in turn can be mono- to polysubstituted by substituents selected from the group consisting of halogen and $C_1$-$C_4$alkyl;
or $R_3$ is $C_1$-$C_6$alkyl, which is substituted by phenylcarbonyl, which phenylcarbonyl in turn can be mono- to polysubstituted by substituents selected from the group consisting of halogen and $C_1$-$C_4$haloalkoxy;
or $R_3$ is $C_1$-$C_6$alkyl, which is substituted by imidazolinyl, which imidazolyl in turn can be mono- to polysubstituted by $C_1$-$C_4$alkyl;
or $R_3$ is $C_1$-$C_6$alkyl, which is substituted by isoxazolyl, which isoxazolyl in turn can be mono- to polysubstituted by halo-substituted phenyl;
or $R_3$ is pyridyl, which in turn can be mono- to polysubstituted by substituents selected from the group consisting of $C_1$-$C_4$alkyl, $C_1$-$C_4$alkoxycarbonyl, phenyl and phenoxy;

or is pyrimidinyl which in turn can be mono- to polysubstituted by substituents selected from the group consisting of hydroxy, $C_1$-$C_4$alkoxy and $C_1$-$C_4$alkyl;
or is piperazinyl, which in turn can be monosubstituted by benzyl;
or is piperidinyl, which in turn can be mono- to polysubstituted by $C_1$-$C_4$alkyl;
or is pyrazolyl, which in turn can be mono- to polysubstituted by substituents selected from the group consisting of $C_1$-$C_4$alkyl, cyano and phenyl;
or is thiethanyl, which can be substituted by $C_1$-$C_4$alkyl;
or is dihydro-thiophene-2-one-3-yl;
or is $C_3$-$C_6$cycloalkyl, which in turn can be mono- to polysubstituted by substituents selected from the group consisting of $C_3$-$C_6$cycloalkyl, $C_2$-$C_6$alkynyl and =N—O—$C_1$-$C_4$haloalkyl;
or is azetidinyl, which in turn can be mono- to polysubstituted by substituents selected from the group consisting of $C_1$-$C_4$haloalkyl and benzyl;
or is pyrrolidinyl which can be substituted by benzyl;
or is $C_1$-$C_6$alkoxycarbonylamino;
or is $C_3$-$C_6$cycloalkenyl which in turn can be mono- to polysubstituted by $C_1$-$C_6$alkoxycarbonyl;
or is phenyl, which in turn can be mono- to polysubstituted by substituents selected from the group consisting of halogen, $C_1$-$C_4$alkyl, $C_1$-$C_4$haloalkyl, $C_1$-$C_4$alkylthio, di($C_1$-$C_4$alkyl)aminosulfonyl, $C_1$-$C_4$alkoxy, phenyl, piperidyl, pyrrolyl, morpholinyl, indolyl, phenylcarbonyl and $C_1$-$C_4$alkoxycarbonyl;
or is quinolinyl, benzothiazolyl or indazolyl;
or is benzothiophenyl, which in turn can be monosubstituted by $C_1$-$C_6$alkoxycarbonyl;
or is thiazolyl, which in turn can be mono- to polysubstituted by substituents selected from the group consisting of $C_1$-$C_4$alkyl, pyridyl, phenyl, pyrimidinyl and $C_1$-$C_4$alkylcarbonyl;
wherein said phenyl can be mono- to polysubstituted by $C_1$-$C_4$alkyl and wherein said pyrimidinyl can be mono- to polysubstituted by $C_1$-$C_4$alkoxy;
or is benzothiazolyl which in turn can be mono- to polysubstituted by $C_1$-$C_4$alkyl;
or is chromen-2-one which in turn can be mono- to polysubstituted by $C_1$-$C_4$alkyl;
or is isoxazolyl, which in turn can be mono- to polysubstituted by substituents selected from the group consisting of $C_1$-$C_4$alkyl and phenyl;
or is thiadiazolyl, which in turn can be monosubstituted by substituents selected from the group consisting of $C_1$-$C_4$alkyl and halo-substituted phenyl;
or is furyl which in turn can be mono- to polysubstituted by substituents selected from the group consisting of cyano and phenyl;
or is pyrazolopyridinyl which in turn can be mono- to polysubstituted by $C_1$-$C_4$alkyl; or is thienyl which in turn can be mono- to polysubstituted by $C_1$-$C_4$alkoxycarbonyl;
or is thietanyloxide, thiethanyldioxide, bicyclo[2.2.1]heptyl or tetrahydrothienyl;
or is isoxazolidin-3-one, which can be monosubstituted by substituents selected from $C_1$-$C_4$alkyl and $C_1$-$C_4$haloalkyl;
or $R_3$ and $R_4$ form together with the nitrogen atom to which they are bonded a 3-6 membered saturated ring which can be mono- to polysubstituted by substituents selected from the group consisting of $C_1$-$C_4$alkyl, $C_1$-$C_4$alkoxy and halogen; and further mono- to polysubstituted by substituents selected from the group consisting of phenylcarbonyl, phenoxy-$C_1$-$C_4$alkyl and phenoxy, which both in turn can be mono- to polysubstituted by halogen; and said ring can be additionally substituted by an ethylene chain; and $R_4$ is hydrogen, $C_1$-$C_6$alkyl, $C_1$-$C_6$haloalkyl or $C_3$-$C_6$cycloalkyl.

In said preferred group of compounds of formula I J is selected from J-1 and J-4.

In said preferred group of compound of formula I, the following meanings of the substituents are especially preferred:

$R_2$ is pyridyl or pyrimidinyl, said pyridyl or pyrimidinyl can be mono- to polysubstituted by halogen; or $R_2$ is thiazolyl which can be substituted by substituents selected from the group consisting of halogen, di-$C_1$-$C_4$alkyl-phosphinoylmethyl-aminocarbonyl and $C_1$-$C_6$alkoxycarbonylamino; or $R_2$ is pyrimidinyl which can be mono- to polysubstituted by $C_1$-$C_4$alkoxy; or $R_2$ is pyrazolyl; or $R_2$ is $C_2$-$C_6$alkynyl which is substituted by substituents selected from the group consisting of pyridinyl, pyraziny-loxy and oxazolyl, which oxazolyl in turn can be substituted by $C_1$-$C_6$alkyl; or $R_2$ is a group —C(O)N($R_3$)$R_4$; wherein $R_3$ is hydrogen, $C_1$-$C_6$alkyl, which can be mono- to polysubstituted by substituents selected from the group consisting of $C_3$-$C_6$cycloalkyl, $C_1$-$C_6$alkylthio, $C_1$-$C_6$haloalkyl, $C_1$-$C_6$alkylsulfinyl, halogen, cyano, hydroxy, $C_1$-$C_6$alkoxy, $C_2$-$C_6$alkenyl, $C_2$-$C_6$alkynyl, $C_1$-$C_6$alkoxy-$C_3$-$C_6$alkynyl, oxolanyl, dioxolanyl, thienyl, thietanyl, thiethanyldioxide, 1-H-benzoimidazol-2-yl, benzo[1,3]dioxolyl, morpholinyl, piperidinyl, pyrimidinyl, pyrrolidinyl, benzylthio, 2,3-dihydro-benzo[1,4]dioxinyl, 1H-indolyl, furyl, —C=N—O—$C_1$-$C_6$alkyl, $C_1$-$C_6$alkylcarbonylamino, phenoxy and phenyl, said phenyl in turn can be mono- to polysubstituted by substituents selected from the group consisting of hydroxy, halogen, $C_1$-$C_6$alkoxy, $C_1$-$C_6$haloalkoxy, pyrazolyl, piperidinyl, phenoxy and $C_1$-$C_4$alkylsulfonyl;

or $R_3$ is $C_1$-$C_6$alkyl, which is substituted by pyridyl, which pyridyl in turn can be mono- to polysubstituted by substituents selected from the group consisting of halogen and $C_1$-$C_4$haloalkyl;

or $R_3$ is $C_1$-$C_6$alkyl, which is substituted by phenoxy, which phenoxy in turn can be mono- to polysubstituted by substituents selected from the group consisting of halogen and $C_1$-$C_4$alkyl;

or $R_3$ is $C_1$-$C_6$alkyl, which is substituted by phenylcarbonyl, which phenylcarbonyl in turn can be mono- to polysubstituted by substituents selected from the group consisting of halogen and $C_1$-$C_4$haloalkoxy;

or $R_3$ is $C_1$-$C_6$alkyl, which is substituted by imidazolinyl, which imidazolyl in turn can be mono- to polysubstituted by $C_1$-$C_4$alkyl;

or $R_3$ is $C_1$-$C_6$alkyl, which is substituted by isoxazolyl, which isoxazolyl in turn can be mono- to polysubstituted by halo-substituted phenyl;

or $R_3$ is pyridyl, which in turn can be mono- to polysubstituted by substituents selected from the group consisting of $C_1$-$C_4$alkyl, $C_1$-$C_4$alkoxycarbonyl, phenyl and phenoxy;

or is pyrimidinyl which in turn can be mono- to polysubstituted by substituents selected from the group consisting of hydroxy, $C_1$-$C_4$alkoxy and $C_1$-$C_4$alkyl;

or is piperazinyl, which in turn can be monosubstituted by benzyl;

or is piperidinyl, which in turn can be mono- to polysubstituted by $C_1$-$C_4$alkyl;

or is pyrazolyl, which in turn can be mono- to polysubstituted by substituents selected from the group consisting of $C_1$-$C_4$alkyl, cyano and phenyl;

or is thiethanyl, which can be substituted by $C_1$-$C_4$alkyl;

or is dihydro-thiophene-2-one-3-yl;

or is $C_3$-$C_6$cycloalkyl, which in turn can be mono- to polysubstituted by substituents selected from the group consisting of $C_3$-$C_6$cycloalkyl, $C_2$-$C_6$alkynyl and =N—O—$C_1$-$C_4$haloalkyl;

or is azetidinyl, which in turn can be mono- to polysubstituted by substituents selected from the group consisting of $C_1$-$C_4$haloalkyl and benzyl;

or is pyrrolidinyl which can be substituted by benzyl;

or is $C_1$-$C_6$alkoxycarbonylamino;

or is $C_3$-$C_6$cycloalkenyl which in turn can be mono- to polysubstituted by $C_1$-$C_6$alkoxycarbonyl;

or is phenyl, which in turn can be mono- to polysubstituted by substituents selected from the group consisting of halogen, $C_1$-$C_4$alkyl, $C_1$-$C_4$haloalkyl, $C_1$-$C_4$alkylthio, di($C_1$-$C_4$alkyl)aminosulfonyl, $C_1$-$C_4$alkoxy, phenyl, piperidyl, pyrrolyl, morpholinyl, indolyl, phenylcarbonyl and $C_1$-$C_4$alkoxycarbonyl;

or is quinolinyl, benzothiazolyl or indazolyl;

or is benzothiophenyl, which in turn can be monosubstituted by $C_1$-$C_6$alkoxycarbonyl;

or is thiazolyl, which in turn can be mono- to polysubstituted by substituents selected from the group consisting of $C_1$-$C_4$alkyl, pyridyl, phenyl, pyrimidinyl and $C_1$-$C_4$alkylcarbonyl;

wherein said phenyl can be mono- to polysubstituted by $C_1$-$C_4$alkyl and wherein said pyrimidinyl can be mono- to polysubstituted by $C_1$-$C_4$alkoxy;

or is benzothiazolyl which in turn can be mono- to polysubstituted by $C_1$-$C_4$alkyl;

or is chromen-2-one which in turn can be mono- to polysubstituted by $C_1$-$C_4$alkyl;

or is isoxazolyl, which in turn can be mono- to polysubstituted by substituents selected from the group consisting of $C_1$-$C_4$alkyl and phenyl;

or is thiadiazolyl, which in turn can be monosubstituted by substituents selected from the group consisting of $C_1$-$C_4$alkyl and halo-substituted phenyl;

or is furyl which in turn can be mono- to polysubstituted by substituents selected from the group consisting of cyano and phenyl;

or is pyrazolopyridinyl which in turn can be mono- to polysubstituted by $C_1$-$C_4$alkyl; or is thienyl which in turn can be mono- to polysubstituted by $C_1$-$C_4$alkoxycarbonyl;

or is thietanyloxide, thiethanyldioxide, bicyclo[2.2.1]heptyl or tetrahydrothienyl;

or is isoxazolidin-3-one, which can be monosubstituted by substituents selected from $C_1$-$C_4$alkyl and $C_1$-$C_4$haloalkyl;

or $R_3$ and $R_4$ form together with the nitrogen atom to which they are bonded a 3-6 membered saturated ring which can be mono- to polysubstituted by substituents selected from the group consisting of $C_1$-$C_4$alkyl, $C_1$-$C_4$alkoxy and halogen; and further mono- to polysubstituted by substituents selected from the group consisting of phenylcarbonyl, phenoxy-$C_1$-$C_4$alkyl and phenoxy, which both in turn can be mono- to polysubstituted by halogen; and said ring can be additionally substituted by an ethylene chain; and $R_4$ is hydrogen, $C_1$-$C_6$alkyl, $C_1$-$C_6$haloalkyl or $C_3$-$C_6$cycloalkyl.

In said preferred group of compound of formula I, the following meanings of the substituents have to be emphasized:

$R_2$ is pyridyl, said pyridyl can be mono- to polysubstituted by halogen; or $R_2$ is thiazolyl which can be substituted by substituents selected from the group consisting of halogen, di-$C_1$-$C_4$alkyl-phosphinoylmethyl-aminocarbonyl and $C_1$-$C_6$alkoxycarbonylamino; or $R_2$ is pyrimidinyl which can be mono- to polysubstituted by $C_1$-$C_4$alkoxy; or $R_2$ is pyrazolyl; or $R_2$ is a group —C(O)N($R_3$)$R_4$; wherein $R_3$ is hydrogen, $C_1$-$C_6$alkyl, which can be mono- to polysubstituted by substituents selected from the group consisting of $C_3$-$C_6$cycloalkyl, $C_1$-$C_6$alkylthio, $C_1$-$C_6$haloalkyl, $C_1$-$C_6$alkylsulfinyl, halogen, cyano, hydroxy, $C_1$-$C_6$alkoxy, $C_2$-$C_6$alkenyl, $C_2$-$C_6$alkynyl, $C_1$-$C_6$alkoxy-$C_3$-$C_6$alkynyl, oxolanyl, dioxolanyl, thienyl, thietanyl, thiethanyldioxide, 1-H-benzoimidazol-2-yl, benzo[1,3]dioxolyl, morpholinyl, piperidinyl, pyrimidinyl, pyrrolidinyl, benzylthio, 2,3-dihydro-benzo[1,4]dioxinyl, 1H-indolyl, furyl, —C=N—O—$C_1$-$C_6$alkyl, $C_1$-$C_6$alkylcarbonylamino, phenoxy and phenyl, said phenyl in turn can be mono- to polysubstituted by substituents selected from the group consisting of hydroxy, halogen, $C_1$-$C_6$alkoxy, $C_1$-$C_6$haloalkoxy, pyrazolyl, piperidinyl, phenoxy and $C_1$-$C_4$alkylsulfonyl;

or $R_3$ is $C_1$-$C_6$alkyl, which is substituted by pyridyl, which pyridyl in turn can be mono- to polysubstituted by substituents selected from the group consisting of halogen and $C_1$-$C_4$haloalkyl;

or $R_3$ is $C_1$-$C_6$alkyl, which is substituted by phenoxy, which phenoxy in turn can be mono- to polysubstituted by substituents selected from the group consisting of halogen and $C_1$-$C_4$alkyl;

or $R_3$ is $C_1$-$C_6$alkyl, which is substituted by phenylcarbonyl, which phenylcarbonyl in turn can be mono- to polysubstituted by substituents selected from the group consisting of halogen and $C_1$-$C_4$haloalkoxy;

or $R_3$ is $C_1$-$C_6$alkyl, which is substituted by imidazolinyl, which imidazolyl in turn can be mono- to polysubstituted by $C_1$-$C_4$alkyl;

or $R_3$ is $C_1$-$C_6$alkyl, which is substituted by isoxazolyl, which isoxazolyl in turn can be mono- to polysubstituted by halo-substituted phenyl;

or $R_3$ is pyridyl, which in turn can be mono- to polysubstituted by substituents selected from the group consisting of $C_1$-$C_4$alkyl, $C_1$-$C_4$alkoxycarbonyl, phenyl and phenoxy;

or is pyrimidinyl which in turn can be mono- to polysubstituted by substituents selected from the group consisting of hydroxy, $C_1$-$C_4$alkoxy and $C_1$-$C_4$alkyl;

or is piperazinyl, which in turn can be monosubstituted by benzyl;

or is piperidinyl, which in turn can be mono- to polysubstituted by $C_1$-$C_4$alkyl;

or is pyrazolyl, which in turn can be mono- to polysubstituted by substituents selected from the group consisting of $C_1$-$C_4$alkyl, cyano and phenyl;

or is thiethanyl, which can be substituted by $C_1$-$C_4$alkyl;

or is dihydro-thiophene-2-one-3-yl;

or is $C_3$-$C_6$cycloalkyl, which in turn can be mono- to polysubstituted by substituents selected from the group consisting of $C_3$-$C_6$cycloalkyl, $C_2$-$C_6$alkynyl and =N—O—$C_1$-$C_4$haloalkyl;

or is azetidinyl, which in turn can be mono- to polysubstituted by substituents selected from the group consisting of $C_1$-$C_4$haloalkyl and benzyl;

or is pyrrolidinyl which can be substituted by benzyl;

or is $C_1$-$C_6$alkoxycarbonylamino;

or is $C_3$-$C_6$cycloalkenyl which in turn can be mono- to polysubstituted by $C_1$-$C_4$alkoxycarbonyl;

or is phenyl, which in turn can be mono- to polysubstituted by substituents selected from the group consisting of halogen, $C_1$-$C_4$alkyl, $C_1$-$C_4$haloalkyl, $C_1$-$C_4$alkylthio, di($C_1$-$C_4$alkyl)aminosulfonyl, $C_1$-$C_4$alkoxy, phenyl, piperidyl, pyrrolyl, morpholinyl, indolyl, phenylcarbonyl and $C_1$-$C_4$alkoxycarbonyl;

or is quinolinyl, benzothiazolyl or indazolyl;

or is benzothiophenyl, which in turn can be monosubstituted by $C_1$-$C_6$alkoxycarbonyl;

or is thiazolyl, which in turn can be mono- to polysubstituted by substituents selected from the group consisting of $C_1$-$C_4$alkyl, pyridyl, phenyl, pyrimidinyl and $C_1$-$C_4$alkylcarbonyl;

wherein said phenyl can be mono- to polysubstituted by $C_1$-$C_4$alkyl and wherein said pyrimidinyl can be mono- to polysubstituted by $C_1$-$C_4$alkoxy;

or is benzothiazolyl, which in turn can be mono- to polysubstituted by $C_1$-$C_4$alkyl;

or is chromen-2-one which in turn can be mono- to polysubstituted by $C_1$-$C_4$alkyl;

or is isoxazolyl, which in turn can be mono- to polysubstituted by substituents selected from the group consisting of $C_1$-$C_4$alkyl and phenyl;

or is thiadiazolyl, which in turn can be monosubstituted by substituents selected from the group consisting of $C_1$-$C_4$alkyl and halo-substituted phenyl;

or is furyl which in turn can be mono- to polysubstituted by substituents selected from the group consisting of cyano and phenyl;

or is pyrazolopyridinyl which in turn can be mono- to polysubstituted by $C_1$-$C_4$alkyl; or is thienyl which in turn can be mono- to polysubstituted by $C_1$-$C_4$alkoxycarbonyl; or is thietanyloxide, thiethanyldioxide, bicyclo[2.2.1]heptyl or tetrahydrothienyl;

or is isoxazolidin-3-one, which can be monosubstituted by substituents selected from $C_1$-$C_4$alkyl and $C_1$-$C_4$haloalkyl;

or $R_3$ and $R_4$ form together with the nitrogen atom to which they are bonded a 3-6 membered saturated ring which can be mono- to polysubstituted by substituents selected from the group consisting of $C_1$-$C_4$alkyl, $C_1$-$C_4$alkoxy and halogen; and further mono- to polysubstituted by substituents selected from the group consisting of phenylcarbonyl, phenoxy-$C_1$-$C_4$alkyl and phenoxy, which both in turn can be mono- to polysubstituted by halogen; and said ring can be additionally substituted by an ethylene chain; and $R_4$ is hydrogen, $C_1$-$C_6$alkyl, $C_1$-$C_6$haloalkyl or $C_3$-$C_6$cycloalkyl.

In said preferred group of compound of formula I, the following meanings of the substituents have to be especially emphasized:

$R_2$ is pyridyl, said pyridyl can be mono- to polysubstituted by halogen; or $R_2$ is thiazolyl which can be substituted by substituents selected from the group consisting of halogen, di-$C_1$-$C_4$alkyl-phosphinoylmethyl-aminocarbonyl and $C_1$-$C_6$alkoxycarbonylamino; or $R_2$ is pyrimidinyl which can be mono- to polysubstituted by $C_1$-$C_4$alkoxy; or $R_2$ is pyrazolyl; or $R_2$ is $C_2$-$C_6$alkynyl which is substituted by substituents selected from the group consisting of pyridinyl, pyraziny-loxy and oxazolyl, which oxazolyl in turn can be substituted by $C_1$-$C_6$alkyl; or $R_2$ is a group —C(O)N($R_3$)$R_4$; wherein $R_3$ is hydrogen, $C_1$-$C_6$alkyl, which can be mono- to polysubstituted by substituents selected from the group consisting of $C_3$-$C_6$cycloalkyl, $C_1$-$C_6$alkylthio, $C_1$-$C_6$haloalkyl, $C_1$-$C_6$alkylsulfinyl, halogen, cyano, hydroxy, $C_1$-$C_6$alkoxy, $C_2$-$C_6$alkenyl, $C_2$-$C_6$alkynyl, $C_1$-$C_6$alkoxy-$C_3$-$C_6$alkynyl, oxolanyl, dioxolanyl, thienyl, thietanyl, thiethanyldioxide, 1-H-benzoimidazol-2-yl, benzo[1,3]dioxolyl, morpholinyl, piperidinyl, pyrimidinyl, pyrrolidinyl, benzylthio, 2,3-dihydro-benzo[1,4]dioxinyl, 1H-indolyl, furyl, —C=N—

O—$C_1$-$C_6$alkyl, $C_1$-$C_6$alkylcarbonylamino and phenyl, said phenyl in turn can be mono- to polysubstituted by substituents selected from the group consisting of hydroxy, halogen, $C_1$-$C_6$alkoxy, $C_1$-$C_6$haloalkoxy, pyrazolyl, piperidinyl, phenoxy and $C_1$-$C_4$alkylsulfonyl;

or $R_3$ is $C_1$-$C_6$alkyl, which is substituted by pyridyl, which pyridyl in turn can be mono- to polysubstituted by substituents selected from the group consisting of halogen and $C_1$-$C_4$haloalkyl;

or $R_3$ is $C_1$-$C_6$alkyl, which is substituted by phenoxy, which phenoxy in turn can be mono- to polysubstituted by substituents selected from the group consisting of halogen and $C_1$-$C_4$alkyl;

or $R_3$ is $C_1$-$C_6$alkyl, which is substituted by phenylcarbonyl, which phenylcarbonyl in turn can be mono- to polysubstituted by substituents selected from the group consisting of halogen and $C_1$-$C_4$haloalkoxy;

or $R_3$ is $C_1$-$C_6$alkyl, which is substituted by imidazolinyl, which imidazolyl in turn can be mono- to polysubstituted by $C_1$-$C_4$alkyl;

or $R_3$ is $C_1$-$C_6$alkyl, which is substituted by isoxazolyl, which isoxazolyl in turn can be mono- to polysubstituted by halo-substituted phenyl;

or $R_3$ is pyridyl, which in turn can be mono- to polysubstituted by substituents selected from the group consisting of $C_1$-$C_4$alkyl, $C_1$-$C_4$alkoxycarbonyl, phenyl and phenoxy;

or is pyrimidinyl which in turn can be mono- to polysubstituted by substituents selected from the group consisting of hydroxy and $C_1$-$C_4$alkyl;

or is piperazinyl, which in turn can be monosubstituted by benzyl;

or is piperidinyl, which in turn can be mono- to polysubstituted by $C_1$-$C_4$alkyl;

or is pyrazolyl, which in turn can be mono- to polysubstituted by substituents selected from the group consisting of $C_1$-$C_4$alkyl, cyano and phenyl;

or is thiethanyl, which can be substituted by $C_1$-$C_4$alkyl;

or is dihydro-thiophene-2-one-3-yl;

or is $C_3$-$C_6$cycloalkyl, which in turn can be mono- to polysubstituted by substituents selected from the group consisting of $C_3$-$C_6$cycloalkyl, $C_2$-$C_6$alkynyl and =N—O—$C_1$-$C_4$haloalkyl;

or is azetidinyl, which in turn can be mono- to polysubstituted by substituents selected from the group consisting of $C_1$-$C_4$haloalkyl and benzyl;

or is pyrrolidinyl which can be substituted by benzyl;

or is $C_3$-$C_6$cycloalkenyl which in turn can be mono- to polysubstituted by $C_1$-$C_6$alkoxycarbonyl;

or is phenyl, which in turn can be mono- to polysubstituted by substituents selected from the group consisting of halogen, $C_1$-$C_4$alkyl, $C_1$-$C_4$haloalkyl, $C_1$-$C_4$alkylthio, di($C_1$-$C_4$alkyl)aminosulfonyl, $C_1$-$C_4$alkoxy, phenyl, piperidyl, pyrrolyl, morpholinyl, indolyl, phenylcarbonyl and $C_1$-$C_4$alkoxycarbonyl;

or is quinolinyl, benzothiazolyl or indazolyl;

or is benzothiophenyl, which in turn can be monosubstituted by $C_1$-$C_6$alkoxycarbonyl;

or is thiazolyl, which in turn can be mono- to polysubstituted by substituents selected from the group consisting of $C_1$-$C_4$alkyl, pyridyl, phenyl, pyrimidinyl and $C_1$-$C_4$alkylcarbonyl; wherein said phenyl can be mono- to polysubstituted by $C_1$-$C_4$alkyl and wherein said pyrimidinyl can be mono- to polysubstituted by $C_1$-$C_4$alkoxy;

or is benzothiazolyl which in turn can be mono- to polysubstituted by $C_1$-$C_4$alkyl;

or is chromen-2-one which in turn can be mono- to polysubstituted by $C_1$-$C_4$alkyl;

or is isoxazolyl, which in turn can be mono- to polysubstituted by substistents selected from the group consisting of $C_1$-$C_4$alkyl and phenyl;

or is thiadiazolyl, which in turn can be monosubstituted by substituents selected from the group consisting of $C_1$-$C_4$alkyl and halo-substituted phenyl;

or is furyl which in turn can be mono- to polysubstituted by substituents selected from the group consisting of cyano and phenyl;

or is pyrazolopyridinyl which in turn can be mono- to polysubstituted by $C_1$-$C_4$alkyl; or is thienyl which in turn can be mono- to polysubstituted by $C_1$-$C_4$alkoxycarbonyl; or is thietanyloxide, thiethanyldioxide, bicyclo[2.2.1]heptyl or tetrahydrothienyl;

or is isoxazolidin-3-one, which can be monosubstituted by substituents selected from $C_1$-$C_4$alkyl and $C_1$-$C_4$haloalkyl;

or $R_3$ and $R_4$ form together with the nitrogen atom to which they are bonded a 3-6 membered saturated ring which can be mono- to polysubstituted by substituents selected from the group consisting of $C_1$-$C_4$alkyl, $C_1$-$C_4$alkoxy and halogen; and further mono- to polysubstituted by substituents selected from the group consisting of phenylcarbonyl, phenoxy-$C_1$-$C_4$alkyl and phenoxy, which both in turn can be mono- to polysubstituted by halogen; and said ring can be additionally substituted by an ethylene chain; and $R_4$ is hydrogen, $C_1$-$C_6$alkyl, $C_1$-$C_6$haloalkyl or $C_3$-$C_6$cycloalkyl.

In said preferred group of compound of formula I, $R_2$ is preferably a group —C(O)N($R_3$)$R_4$; wherein preferably $R_3$ is thiethanyl, which can be substituted by $C_1$-$C_4$alkyl; or is thietanyldioxide, thietanyloxide or tetrahydrothienyl; or is $C_1$-$C_6$alkyl substituted by substituents selected from the group consisting of $C_2$-$C_6$alkynyl, $C_1$-$C_6$alkylthio, $C_1$-$C_6$alkylcarbonylamino, $C_1$-$C_6$haloalkyl, thienyl, thietanyl and thiethanyldioxide; in particular $R_3$ is thiethanyl, which can be substituted by $C_1$-$C_4$alkyl; or is thietanyldioxide, thietanyloxide or tetrahydrothienyl; or is $C_1$-$C_6$alkyl substituted by $C_1$-$C_6$alkylthio, thienyl, thietanyl and thiethanyldioxide; and $R_4$ is hydrogen.

The method according to the invention for the preparation of compounds of formula Ia

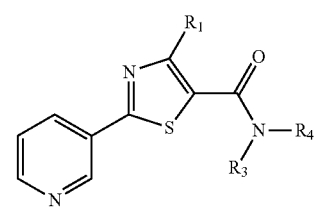

(Ia)

wherein $R_1$, $R_3$ and $R_4$ are as described under formula I above, comprises reacting a compound of formula II

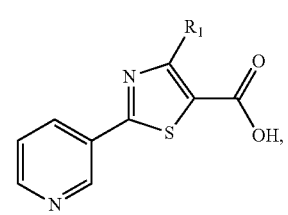

(II)

wherein R₁ is chlorine, with a compound of formula IIa $$HNR_3R_4 \tag{IIa}$$

wherein R₃ and R₄ are as described under formula I above, in the presence of a coupling reagent as described e.g. by C. A. G. N. Montalbetti and V. Falque in Tetrahedron, 2005, 61, 10827 or in Aldrich ChemFiles, 2007, 7 (2), url: http://www.sigmaaldrich.com/etc/medialib/docs/Aldrich/Brochure/al_chemfile_v7_n2.Par.0001.File.tmp/al_chemfile_v7_n2.pdf.

Alternatively, compounds of formula Ia can be prepared from compound of formula III

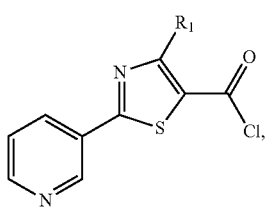

(III)

wherein R₁ is as described under formula I above, and compound of formula IIa $$HNR_3R_4, \tag{IIa},$$

wherein R₃ and R₄ are as described under formula I above, in the presence of a base and optionally in the presence of a catalyst such as dimethylaminopyridine.

Examples of a suitable base are triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU) or 1,5-Diazabicyclo (4.3.0)non-5-ene (DBN).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

The compound of formula III is prepared from the compound of formula II under routine reaction conditions as described in March's Advanced Organic Chemistry, 6ᵗʰ edition, Wiley, New York, 2007, p. 1440-1.

The compound of formula II is prepared according to reaction scheme 1. The known compound of formula IV is chlorinated to the compound of formula V, as described e.g. in WO 2008/083070 p. 63, which is deprotonated with a base such as LDA, LiHMDS, NaHMDS, KHMDS and reacted with CO₂ as described e.g. in J. Chem. Soc. Perkin Trans. I, 1992, 215. The compound of formula VI is coupled in a Suzuki reaction with a boronic derivative of formula VII wherein Ra is B(OH)₂, B(OMe)₂, B(OiPr)₂, BF₃K or B(—OCMe₂CMe2O—) to compound of formula II. Alternatively compound of formula VI is esterified to compound of formula VIII which react with compound of formula VII to compound of formula IX, which is reacted in a Suzuki reaction with a compound of formula VII, with Ra as defined above, and then saponified to the compound of formula II. Methods of chlorination, esterification and saponification are described in March's Advanced Organic Chemistry, 6ᵗʰ edition, Wiley, New York, 2007. The Suzuki reaction is known from the literature e.g. J. P. Wolfe, J. S. Nakhla, The Suzuki Reaction in Name Reactions for Homologations, John Wiley & Sons, Inc., Hoboken, N.J., 2009, Pt. 1, 163.

Reaction Scheme 1:

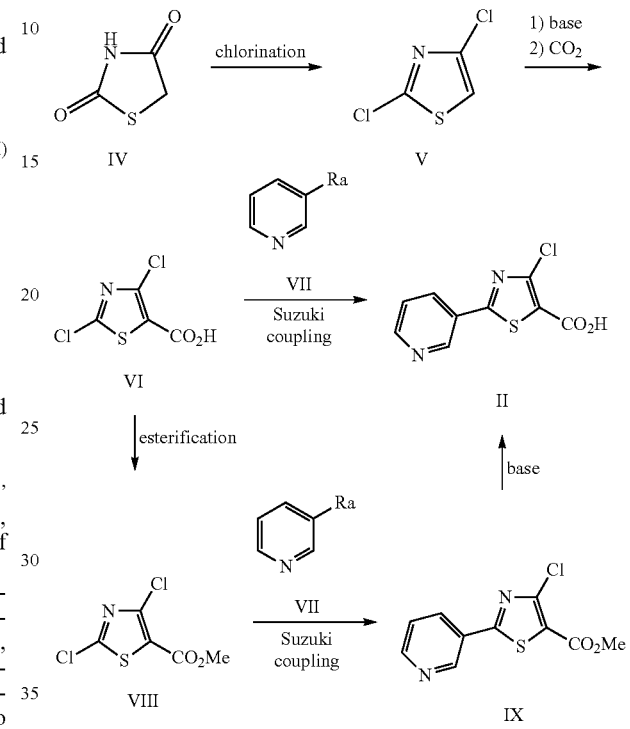

The method according to the invention for the preparation of compounds of formula Ib,

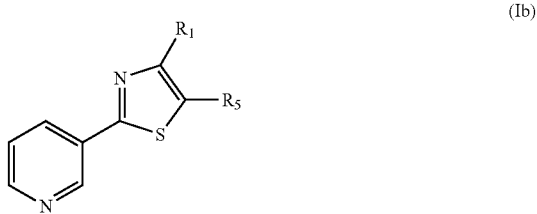

(Ib)

wherein the meanings of R₅ correspond to the meanings for R₂ in claim 1 except for the group —C(O)N(R₃)R₄, preferably R₅ is a 5- or 6-membered optionally substituted heterocycle; preferably R₅ is pyridyl or pyrimidyl, said pyridyl or pyrimidyl can be mono- to polysubstituted by substituents selected from the group consisting of pyrimidinyl, halogen and pyridyl, wherein said pyrimidinyl and pyridyl in turn can be mono- to polysubstituted by halogen, C₁-C₆alkyl, C₁-C₆haloalkyl, C₁-C₆alkoxy; or is thiazolyl which can be substituted by substituents selected from the group consisting of halogen, di-C₁-C₄alkyl-phosphinoylmethylaminocarbonyl and C₁-C₆alkoxycarbonylamino; is [1,3,4]oxadiazole-2-yl, which can be substituted by pyridinyl which in turn can be substituted by C₁-C₄alkyl; or is [1,3,4]thiadiazole-2-yl, which can be substituted by pyridinyl which in turn can be substituted by C₁-C₄alkyl; comprises reacting a compound of formula X,

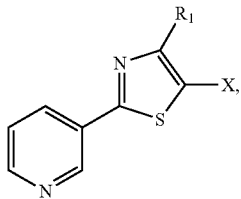

(X)

wherein $R_1$ is as described under formula I above and X is chloro, bromo, iodo, OMesyl or trifluoromethanesulfonate (OTf), in a Suzuki reaction with a compound of formula $R_5$-Ra, wherein $R_5$ is as described under formula Ib above and Ra is $B(OH)_2$, $B(OMe)_2$, $B(OiPr)_2$, $BF_3K$ or $B(—OCMe_2CMe2O—)$.

Compounds of formula X, wherein X is chloro, bromo or iodo, can be made from compounds of formula XI according to the reaction scheme 2. Halogenation reactions are known from literature, e.g. March's Advanced Organic Chemistry, 6th edition, Wiley, New York, 2007.

Reaction Scheme 2:

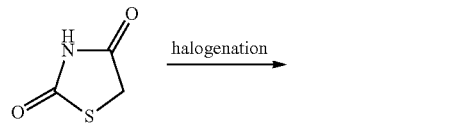

As depicted in the reaction scheme 3, the method according to the invention for the preparation of compounds of formula Ib, wherein $R_5$ is as described above,

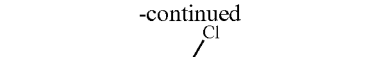

(Ib)

comprises reacting a compound of formula XI with a compound of formula $R_5$—X, wherein X is chloro, bromo, iodo, OMesyl or trifluoromethanesulfonate (OTf), by a C—H activation method, as known from the literature (e.g. L. Ackermann et al. Angew. Chem. Int Ed. 2009, 48, 9792 or J. Q. Yu, Z. Shi Eds., Topics in Current Chemistry, 2010, vol. 292, Springer). Alternatively, the compound of formula X, wherein X is chloro, bromo, iodo OMesyl or trifluoromethanesulfonate, is borylated under known condition to a compound of formula XII, which react with a compound of formula $R_5$—X, wherein X is chloro, bromo, iodo, OMesyl or trifluoromethanesulfonate (OTf) in a Suzuki reaction to give a compound of formula Ib.

Reaction Scheme 3:

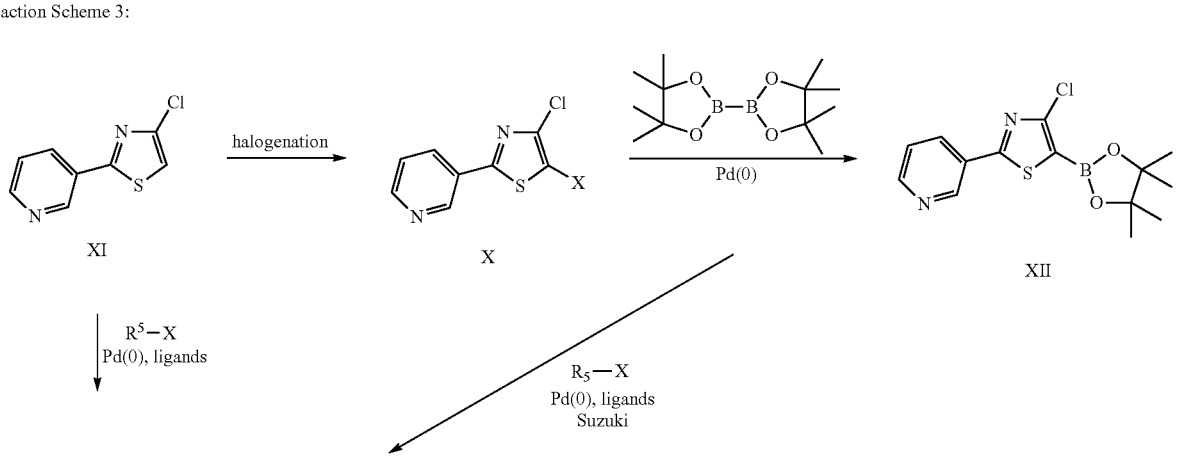

Ib

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties can be obtained in free form or in the form of salts.

The compounds of formula I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from J. Med. Chem., 32 (12), 2561-73, 1989 or WO 00/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds of formula I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i. e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

Examples of the abovementioned animal pests are:

from the order Acarina, for example,

*Acalitus* spp, *Aculus* spp, *Acaricalus* spp, *Aceria* spp, *Acarus siro*, *Amblyomma* spp., *Argas* spp., *Boophilus* spp., *Brevipalpus* spp., *Bryobia* spp, *Calipitrimerus* spp., *Chorioptes* spp., *Dermanyssus gallinae*, *Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.;

from the order Coleoptera, for example,

*Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp., *Psylliodes* spp., *Rhyssomatus aubtilis*, *Rhizopertha* spp., *Scarabeida* spp., *Sitophilus* spp., *Sitotroga* spp., *Somaticus* spp, *Sphenophorus* spp, *Sternechus subsignatus*, *Tenebrio* spp., *Tribolium* spp. and *Trogoderma* spp.;

from the order Diptera, for example,

*Aedes* spp., *Anopheles* spp, *Antherigona soccata*, *Bactrocea oleae*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;

from the order Hemiptera, for example,

*Acanthocoris scabrator*, *Acrosternum* spp, *Adelphocoris lineolatus*, *Amblypelta nitida*, *Bathycoelia thalassina*, *Blissus* spp, *Cimex* spp., *Clavigralla tomentosicollis*, *Creontiades* spp, *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp, *Murgantia histrionic*, *Neomegalotomus* spp, *Nesidiocoris tenuis*, *Nezara* spp., *Nysius simulans*, *Oebalus insularis*, *Piesma* spp., *Piezodorus* spp, *Rhodnius* spp., *Sahlbergella singularis*, *Scaptocoris castanea*, *Scotinophara* spp., *Thyanta* spp, *Triatoma* spp., *Vatiga illudens*;

*Acyrthosium pisum*, *Adalges* spp, *Agalliana ensigera*, *Agonoscena targionii*, *Aleurodicus* spp, *Aleurocanthus* spp, *Aleurolobus barodensis*, *Aleurothrixus floccosus*, *Aleyrodes brassicae*, *Amarasca biguttula*, *Amritodus atkinsoni*, *Aonidiella* spp., *Aphididae*, *Aphis* spp., *Aspidiotus* spp., *Aulacorthum solani*, *Bactericera cockerelli*, *Bemisia* spp, *Brachycaudus* spp, *Brevicoryne brassicae*, *Cacopsylla* spp, *Cavariella aegopodii* Scop., *Ceroplaster* spp., *Chrysomphalus aonidium*, *Chrysomphalus dictyospermi*, *Cicadella* spp, *Cofana spectra*, *Cryptomyzus* spp, *Cicadulina* spp, *Coccus hesperidum*, *Dalbulus maidis*, *Dialeurodes* spp, *Diaphorina citri*, *Diuraphis noxia*, *Dysaphis* spp, *Empoasca* spp., *Eriosoma larigerum*, *Erythroneura* spp., *Gascardia* spp., *Glycaspis brimblecombei*, *Hyadaphis pseudobrassicae*, *Hyalopterus* spp, *Hyperomyzus pallidus*, *Idioscopus clypealis*, *Jacobiasca lybica*, *Laodelphax* spp., *Lecanium corni*, *Lepidosaphes* spp., *Lopaphis erysimi*, *Lyogenys maidis*, *Macrosiphum* spp., *Mahanarva* spp, *Metcalfa pruinosa*, *Metopolophium dirhodum*, *Myndus crudus*, *Myzus* spp., *Neotoxoptera* sp, *Nephotettix* spp., *Nilaparvata* spp., *Nippolachnus piri* Mats, *Odonaspis ruthae*, *Oregma lanigera* Zehnter, *Parabemisia myricae*, *Paratrioza cockerelli*, *Parlatoria* spp., *Pemphigus* spp., *Peregrinus maidis*, *Perkinsiella* spp, *Phorodon humuli*, *Phylloxera* spp, *Planococcus* spp., *Pseudaulacaspis* spp., *Pseudococcus* spp., *Pseudatomoscelis seriatus*, *Psylla* spp., *Pulvinaria aethiopica*, *Quadraspidiotus* spp., *Quesada gigas*, *Recilia dorsalis*, *Rhopalosiphum* spp., *Saissetia* spp., *Scaphoideus* spp., *Schizaphis* spp., *Sitobion* spp., *Sogatella furcifera*, *Spissistilus festinus*, *Tarophagus Proserpina*, *Toxoptera* spp, *Trialeurodes* spp, *Tridiscus sporoboli*, *Trionymus* spp, *Trioza erytreae*, *Unaspis citri*, *Zygina flammigera*, *Zyginidia scutellaris*;

from the order Hymenoptera, for example,

*Acromyrmex*, *Arge* spp, *Atta* spp., *Cephus* spp., *Diprion* spp., *Diprionidae*, *Gilpinia polytoma*, *Hoplocampa* spp., *Lasius* spp., *Monomorium pharaonis, Neodiprion* spp., *Pogonomyrmex* spp, *Slenopsis invicta, Solenopsis* spp. and *Vespa* spp.;
from the order Isoptera, for example,
*Coptotermes* spp, *Corniternes cumulans, Incisitermes* spp, *Macrotermes* spp, *Mastotermes* spp, *Microtermes* spp, *Reticulitermes* spp.; *Solenopsis geminate*
from the order Lepidoptera, for example,
*Acleris* spp., *Adoxophyes* spp., *Aegeria* spp., *Agrotis* spp., *Alabama argillaceae, Amylois* spp., *Anticarsia gemmatalis, Archips* spp., *Argyresthia* spp, *Argyrotaenia* spp., *Autographa* spp., *Bucculatrix thurberiella, Busseola fusca, Cadra cautella, Carposina nipponensis, Chilo* spp., *Choristoneura* spp., *Chrysoteuchia topiaria, Clysia ambiguella, Cnaphalocrocis* spp., *Cnephasia* spp., *Cochylis* spp., *Coleophora* spp., *Colias lesbia, Cosmophila flava, Crambus* spp, *Crocidolomia binotalis, Cryptophlebia leucotreta, Cydalima perspectalis, Cydia* spp., *Diaphania perspectalis, Diatraea* spp., *Diparopsis castanea, Earias* spp., *Eldana saccharina, Ephestia* spp., *Epinotia* spp, *Estigmene acrea, Etiella zinckinella, Eucosma* spp., *Eupoecilia ambiguella, Euproctis* spp., *Euxoa* spp., *Feltia jaculiferia, Grapholita* spp., *Hedya nubiferana, Heliothis* spp., *Hellula undalis, Herpetogramma* spp, *Hyphantria cunea, Keiferia lycopersicella, Lasmopalpus lignosellus, Leucoptera scitella, Lithocollethis* spp., *Lobesia botrana, Loxostege bifidalis, Lymantria* spp., *Lyonetia* spp., *Malacosoma* spp., *Mamestra brassicae, Manduca sexta, Mythimna* spp, *Noctua* spp, *Operophtera* spp., *Orniodes indica, Ostrinia nubilalis, Pammene* spp., *Pandemis* spp., *Panolis flammea, Papaipema nebris, Pectinophora gossypiela, Perileucoptera coffeella, Pseudaletia unipuncta, Phthorimaea operculella, Pieris rapae, Pieris* spp., *Plutella xylostella, Prays* spp., *Pseudoplusia* spp, *Rachiplusia nu, Richia albicosta, Scirpophaga* spp., *Sesamia* spp., *Sparganothis* spp., *Spodoptera* spp., *Sylepta derogate, Synanthedon* spp., *Thaumetopoea* spp., *Tortrix* spp., *Trichoplusia ni, Tuta absoluta*, and *Yponomeuta* spp.;
from the order Mallophaga, for example,
*Damalinea* spp. and *Trichodectes* spp.;
from the order Orthoptera, for example,
*Blatta* spp., *Blattella* spp., *Gryllotalpa* spp., *Leucophaea maderae, Locusta* spp., *Neocurtilla hexadactyla, Periplaneta* spp., *Scapteriscus* spp, and *Schistocerca* spp.;
from the order Psocoptera, for example,
*Liposcelis* spp.;
from the order Siphonaptera, for example,
*Ceratophyllus* spp., *Ctenocephalides* spp. and *Xenopsylla cheopis;*
from the order Thysanoptera, for example,
*Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp;
from the order Thysanura, for example, *Lepisma saccharina.*

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatos) and *Chilo supressalis* (preferably in rice).

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus.*

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as *Streptomycetes* toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); Nature-Gard®, Agrisure® GT Advantage (GA21 glyphosate-tolerant trait), Agrisure® CB Advantage (Bt11 corn borer (CB) trait) and Protecta®.

Further examples of such transgenic crops are:
1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and storerooms and the protection of raw materials, such as wood, textiles, floor coverings or buildings, and also in the hygiene sector, especially the protection of humans, domestic animals and productive livestock against pests of the mentioned type.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:
Of the order Anoplurida: *Haematopinus* spp., *Linognathus* spp., *Pediculus* spp. and *Phtirus* spp., *Solenopotes* spp.
Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis, Periplaneta americana, Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus,* and also hymenopterans such as *Sirex juvencus, Urocerus gigas, Urocerus gigas taignus* and *Urocerus augur,* and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus,* and bristletails such as *Lepisma saccharina.*

The invention therefore also relates to pesticidal compositions such as emulsifiable concentrates, suspension concentrates, microemulsions, oil dispersibles, directly sprayable or dilutable solutions, spreadable pastes, dilute emulsions, soluble powders, dispersible powders, wettable powders, dusts, granules or encapsulations in polymeric substances, which comprise—at least—one of the active ingredients according to the invention and which are to be selected to suit the intended aims and the prevailing circumstances.

In these compositions, the active ingredient is employed in pure form, a solid active ingredient for example in a specific particle size, or, preferably, together with—at least—one of the auxiliaries conventionally used in the art of formulation, such as extenders, for example solvents or solid carriers, or such as surface-active compounds (surfactants).

Examples of suitable solvents are: unhydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers. Suitable particulate adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopolypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylphenoxypolyethoxyethanol, polyethylene glycol or octylphenoxypolyethoxyethanol. Also suitable are fatty acid esters of polyoxyethylene sorbitan, such as polyoxyethylene sorbitan trioleate. The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethyl-ammonium bromide.

Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulphuric ester or of a fatty alcohol sulfate mixture prepared from natural fatty acids. This group also includes the salts of the sulphuric esters and sulfonic acids of fatty alcohol/ethylene oxide adducts. The sulfonated benzimidazole derivatives preferably contain 2 sulphonyl groups and a fatty acid radical of approximately 8 to approximately 22 C atoms. Examples of alkylarylsulfonates are the sodium, calcium or triethanolammonium salts of decylbenzenesulfonic acid, of dibutylnaphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids.

As a rule, the compositions comprise 0.1 to 99%, especially 0.1 to 95%, of active ingredient and 1 to 99.9%, especially 5 to 99.9%, of at least one solid or liquid adjuvant, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient. Preferred compositions are composed in particular as follows (%=percent by weight):

Emulsifiable Concentrates:
active ingredient: 1 to 95%, preferably 5 to 20%
surfactant: 1 to 30%, preferably 10 to 20%
solvent: 5 to 98%, preferably 70 to 85%
Dusts:
active ingredient: 0.1 to 10%, preferably 0.1 to 1%
solid carrier: 99.9 to 90%, preferably 99.9 to 99%
Suspension Concentrates:
active ingredient: 5 to 75%, preferably 10 to 50%
water: 94 to 24%, preferably 88 to 30%
surfactant: 1 to 40%, preferably 2 to 30%
Wettable Powders:
active ingredient: 0.5 to 90%, preferably 1 to 80%
surfactant: 0.5 to 20%, preferably 1 to 15%
solid carrier: 5 to 99%, preferably 15 to 98%
Granulates:
active ingredient: 0.5 to 30%, preferably 3 to 15%
solid carrier: 99.5 to 70%, preferably 97 to 85%

PREPARATORY EXAMPLES

"M.p." means melting point in ° C.

Example P1: Preparation of 2,4-dichlorothiazole

50 g (427 mmol) thiazolidine-2,4-dione was dissolved in 240 ml $POCl_3$ and 34 ml (422 mmol) pyridine were added at 5° C. during 15 minutes. The reaction mixture was heated at 125° C. for 4 hours and cooled down. Phosphoroxychloride was removed by evaporation and the residue was poured on a mixture of water and ice. 2,4-Dichlorothiazole crystallized and was filtered to give 34.8 g white crystals, m.p.: 45-6° C.

Example P2: Preparation of 2,4-dichloro-thiazole-5-carboxylic acid

Diisopropylamine (42 ml, 297 mmol) was dissolved in 1000 ml THF and cooled to −70° C. 181.2 ml nBuLi (1.6M in hexane, 290 mmol) was added. The temperature was briefly raised to 0° C. and the reaction mixture was again cooled down to −70° C. 2,4-Dichlorothiazole (40.8 g, 265 mmol) in 200 ml THF was slowly added at −70° C. Dry ice was put in a separate vessel connected to the reaction mixture with a Teflon tube and the $CO_2$ formed bubbled in the reaction mixture at −78° C. The mixture was stirred for 18 hours in the cooling bath and the temperature reached 20° C. The mixture was quenched with 2N HCl. After saturating the water phase with NaCl, the mixture was extracted with ethyl acetate, dried with $MgSO_4$ and evaporated to give 48.0 g 2,4-dichloro-thiazole-5-carboxylic acid, mp: 165-166° C.

Example P3: Preparation of 4-chloro-2-pyridin-3-yl-thiazole-5-carboxylic acid

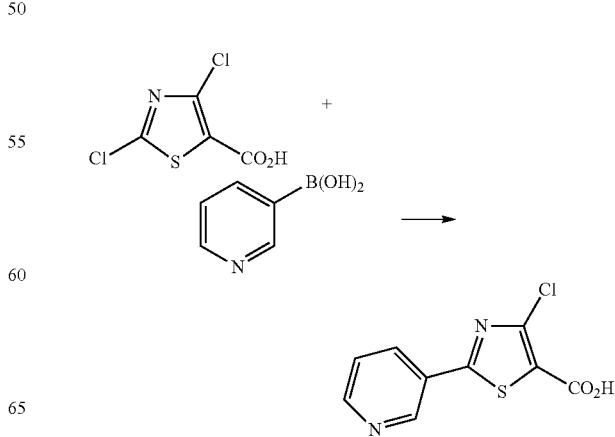

9.0 g (45 mmol) 2,4-dichloro-thiazole-5-carboxylic acid and 7.5 g (60 mmol) 3-pyridine boronic acid were dissolved in 180 ml dimethoxyethane. 12.0 g Na$_2$CO$_3$ in 60 ml water was added and the mixture was purged with argon for 5 min. Pd(PPh$_3$)$_4$ (1.5 g, 1.3 mmol) was added and the reaction was heated at 85° C. for 18 hours. After cooling, 100 ml NaOH 1N and 150 ml ethyl acetate were added and the mixture was stirred 15 min. The water phase was separated and acidified with HCl 1N to pH 2-3. Crystals separated which were filtered and digested with diethyl ether/acetonitrile to give 9.4 g brown crystals of 4-chloro-2-pyridin-3-yl-thiazole-5-carboxylic acid. M.p.: 238-251° C.

Example P4: Preparation of 4-chloro-2-pyridin-3-yl-thiazole-5-carbonyl chloride hydrochloride

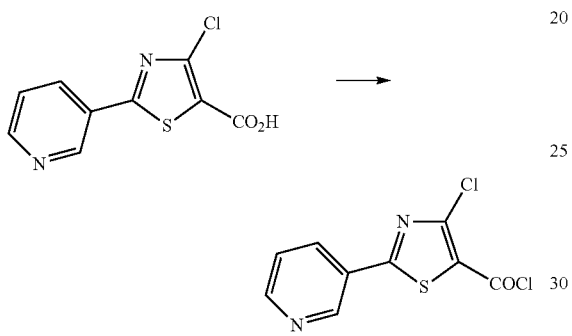

2.9 g (12.0 mmol) 4-chloro-2-pyridin-3-yl-thiazole-5-carboxylic acid was suspended in 50 ml CH$_2$Cl$_2$ and 15 ml oxalylchloride were added. After heating 3 h at 45° C., the mixture was evaporated to give 3.5 g 4-chloro-2-pyridin-3-yl-thiazole-5-carbonyl chloride hydrochloride which was directly used in the subsequent reaction.

Example P5: Preparation of 4-chloro-2-pyridin-3-yl-thiazole-5-carboxylic acid (2-methylsulfanyl-ethyl)-amide

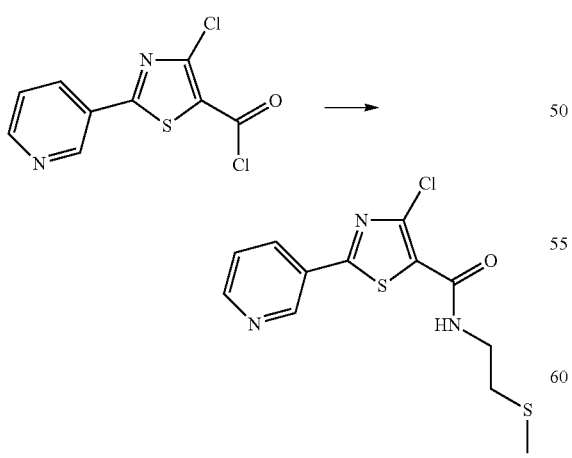

860 mg (2.9 mmol) 4-chloro-2-pyridin-3-yl-thiazole-5-carbonyl chloride hydrochloride was suspended in 20 ml THF. 2-Methylsulfanyl-ethylamine (264 mg, 2.9 mmol), triethylamine (1.2 ml, 8.7 mmol) and catalytic DMAP were added. The reaction was stirred overnight at RT. After filtration of the insoluble material, the residue was evaporated and directly submitted to flash-chromatography (ethyl acetate/hexane 1:1 to ethyl acetate 100%) to give 430 mg of the desired compound. M.p.: 97-98° C.

Example P6: Preparation of 3-(4-chloro-thiazol-2-yl)-pyridine

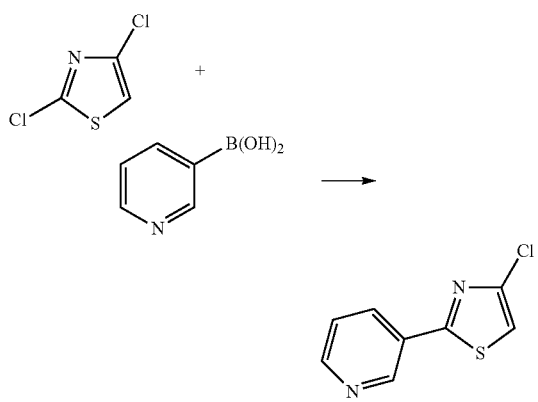

In a mixture of 600 ml toluene and 180 ml ethanol were suspended 26.0 g (169 mmol) 2,4-dichlorothiazole, 22.0 g (180 mmol) 3-pyridine boronic acid and a solution of 46 g K$_2$CO$_3$ in 350 ml water. The suspension was purged with argon for 5 min and 8.0 g (6.9 mmol) Pd(PPh$_3$)$_4$ was added. The mixture was heated at 80° C. for 18 hours. The mixture was cooled down, diluted with ethyl acetate and washed with water. The organic phase was concentrated and extracted with HCl 1N. The water phase was cooled with ice and neutralized with a 4M NaOH solution. Crystals separated which were filtered, solved in ethyl acetate. The organic phase was dried over MgSO$_4$ and evaporated. The residue was digested in petrol ether to give 16.1 g crystals of 3-(4-chloro-thiazol-2-yl)-pyridine. M.p.: 87-90° C.

Example P7: Preparation of 3-(5-bromo-4-chloro-thiazol-2-yl)-pyridine

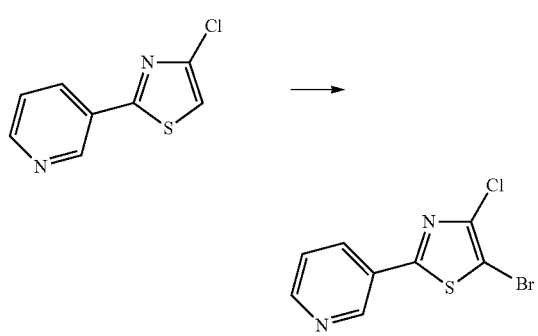

11.0 g (56 mmol) 3-(4-chloro-thiazol-2-yl)-pyridine was solved in 120 ml CH$_2$Cl$_2$ and cool to 0° C. 10 ml (mmol) bromine was slowly added at that temperature. The crystals formed were filtered. The crystals were suspended in 200 ml water and treated with sodium thiosulfate. The solution was made basic with NaOH 1N (pH~12) and was extracted with ethyl acetate. After drying the organic phase (MgSO$_4$) and evaporating the solvent, the residue was crystallized in petrol ether/diisopropanol to give 12.9 g crystals of 2-[6-(4-chloro-2-pyridin-3-yl-thiazol-5-yl)-pyridin-2-yl]-pyrimidine. M.p.: 114-115° C.

Example P8: Preparation of 3-(4-chloro-5-pyrid-3-yl-thiazol-2-yl)-pyridine

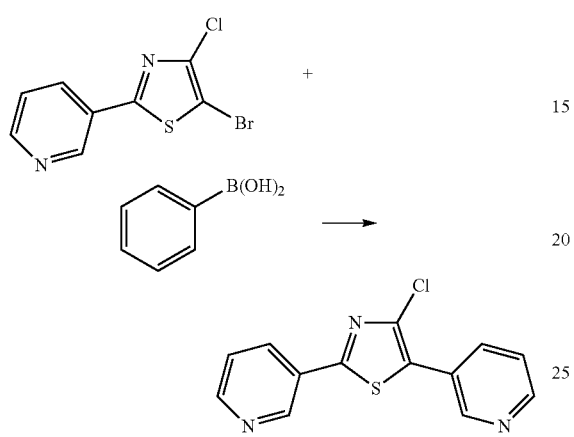

In a solution of 50 ml toluene and 15 ml ethanol, 1 g (3.6 mmol) 3-(5-bromo-4-chloro-thiazol-2-yl)-pyridine, 0.5 g (4.0 mmol) pyridine-3-boronic acid and a solution of 1.1 g K$_2$CO$_3$ in 10 ml water were added. After purging with argon for 10 minutes, 0.5 g (0.43 mmol) Pd(PPh$_3$)$_4$ was added and the reaction was heated at reflux for 18 hours. After cooling, the mixture was extracted with 1N HCl. The acidic phase was basified with NaOH 1M (pH-8-9) and crystals separated. After filtration and digestion of the crystals in acetonitrile, 0.31 of 3-(4-chloro-5-pyrid-3-yl-thiazol-2-yl)-pyridine was isolated. M.p.: 145-7° C.

The compounds according to the following table P can be prepared analogously. The examples which follow are intended to illustrate the invention and show preferred compounds of formula I.

Table P: Physical Data of Compounds of Formula I:

In the drawings, free radicals signify a methyl group. For example, compound No. 1.021

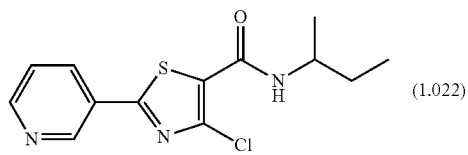 [SMILES: CCC(C)NC(=O)c1sc(-c2cccnc2)nc1Cl]

can also be drawn as:

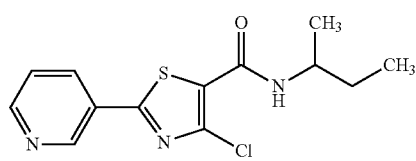 [SMILES: CCC(C)NC(=O)c1sc(-c2cccnc2)nc1Cl]

(1.022)

| Compound No. | Structure | Phys. Data |
|---|---|---|
| 1.001 | 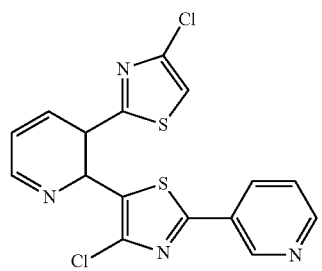 [SMILES: Clc1csc(C2C=CC=NC2c2sc(-c3cccnc3)nc2Cl)n1] | LCMS_2: 393 (M + 1) |
| 1.002 | 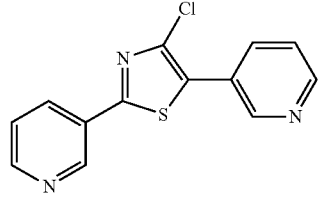 [SMILES: Clc1nc(-c2cccnc2)sc1-c1cccnc1] | LCMS_2: 274 (M + 1) |

-continued
(1.022)
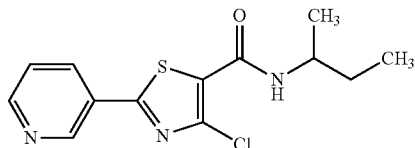
| Compound No. | Structure | Phys. Data |
|---|---|---|
| 1.003 | 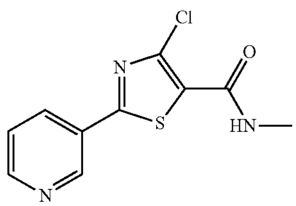 [SMILES: CNC(=O)c1sc(-c2cccnc2)nc1Cl] | LCMS_2: 254 (M + 1) |
| 1.004 | 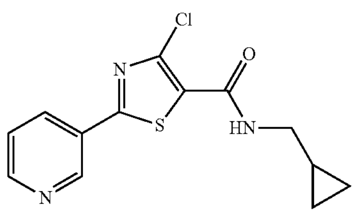 [SMILES: O=C(NCC1CC1)c1sc(-c2cccnc2)nc1Cl] | LCMS_2: 294 (M + 1) |
| 1.005 | 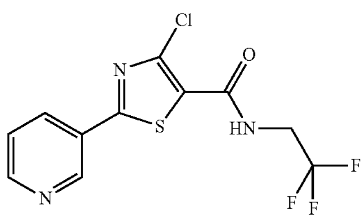 [SMILES: O=C(NCC(F)(F)F)c1sc(-c2cccnc2)nc1Cl] | LCMS_1: 322 (M + 1) |
| 1.006 | 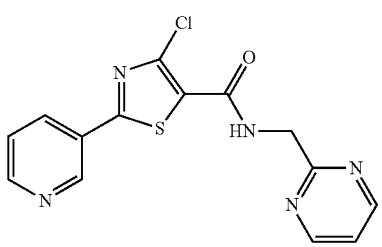 [SMILES: O=C(NCc1ncccn1)c1sc(-c2cccnc2)nc1Cl] | LCMS_2: 332 (M + 1) |
| 1.007 | 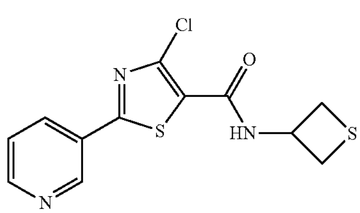 [SMILES: O=C(NC1CSC1)c1sc(-c2cccnc2)nc1Cl] | LCMS_1: 312 (M + 1) |
| 1.008 | 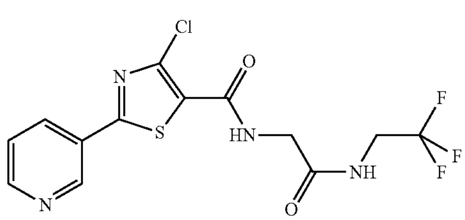 [SMILES: O=C(CNC(=O)c1sc(-c2cccnc2)nc1Cl)NCC(F)(F)F] | LCMS_1: 379 (M + 1) |

(1.022)
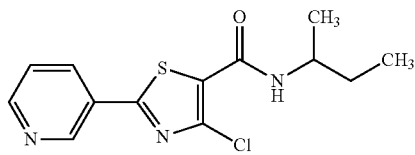
| Compound No. | Structure | Phys. Data |
|---|---|---|
| 1.009 | 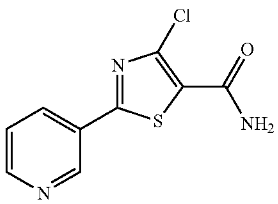 [SMILES: NC(=O)c1sc(-c2cccnc2)nc1Cl] | LCMS_2: 240 (M + 1) |
| 1.010 | 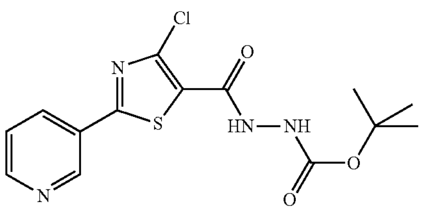 [SMILES: CC(C)(C)OC(=O)NNC(=O)c1sc(-c2cccnc2)nc1Cl] | LCMS_2: 355 (M + 1) |
| 1.011 | 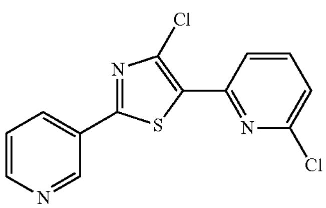 [SMILES: Clc1cccc(-c2sc(-c3cccnc3)nc2Cl)n1] | LCMS_2: 308 (M + 1) |
| 1.012 | 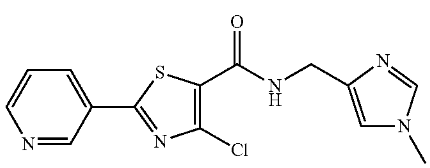 [SMILES: Cn1cnc(CNC(=O)c2sc(-c3cccnc3)nc2Cl)c1] | LCMS_1: 334 (M + 1) |
| 1.013 | 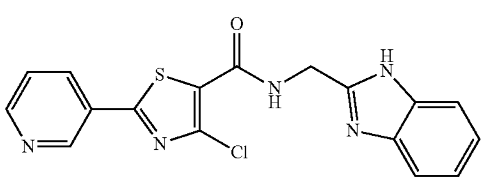 [SMILES: O=C(NCc1nc2ccccc2[nH]1)c1sc(-c2cccnc2)nc1Cl] | LCMS_1: 370 (M + 1) |
| 1.014 | 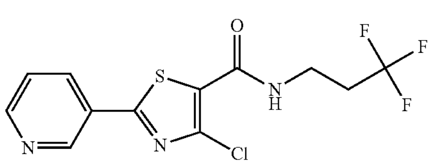 [SMILES: O=C(NCCC(F)(F)F)c1sc(-c2cccnc2)nc1Cl] | LCMS_1: 335 (M + 1) |
| 1.015 | 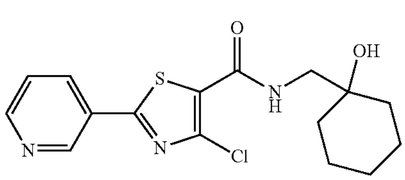 [SMILES: O=C(NCC1(O)CCCCC1)c1sc(-c2cccnc2)nc1Cl] | LCMS_1: 351 (M + 1) |

(1.022)
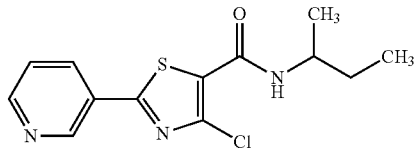
| Compound No. | Structure | Phys. Data |
|---|---|---|
| 1.016 | 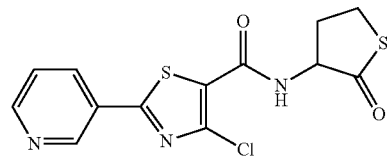 [SMILES: O=C(NC1CCSC1=O)c1sc(-c2cccnc2)nc1Cl] | LCMS_1: 334 (M + 1) |
| 1.017 | 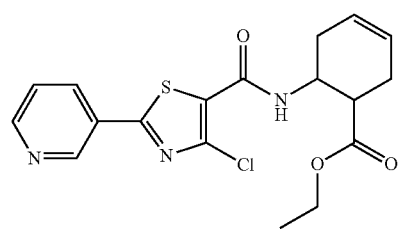 [SMILES: CCOC(=O)C1CC=CCC1NC(=O)c1sc(-c2cccnc2)nc1Cl] | LCMS_1: 392 (M + 1) |
| 1.018 | 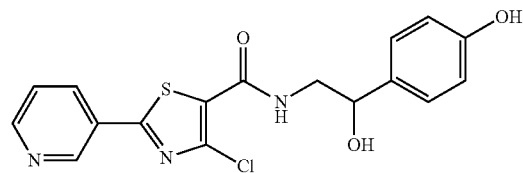 [SMILES: O=C(NCC(O)c1ccc(O)cc1)c1sc(-c2cccnc2)nc1Cl] | LCMS_1: 376 (M + 1) |
| 1.019 | 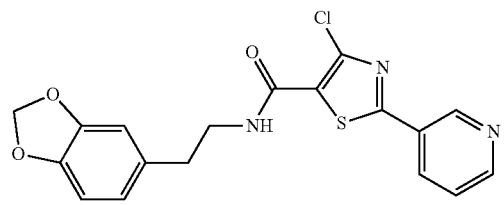 [SMILES: O=C(NCCc1ccc2c(c1)OCO2)c1sc(-c2cccnc2)nc1Cl] | LCMS_1: 388 (M + 1) |
| 1.020 | 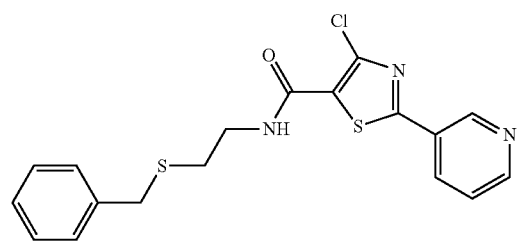 [SMILES: O=C(NCCSCc1ccccc1)c1sc(-c2cccnc2)nc1Cl] | LCMS_1: 390 (M + 1) |
| 1.021 | 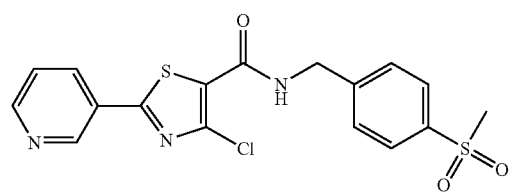 [SMILES: CS(=O)(=O)c1ccc(CNC(=O)c2sc(-c3cccnc3)nc2Cl)cc1] | LCMS_1: 408 (M + 1) |
| 1.022 | 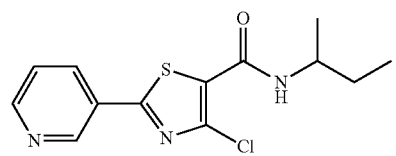 [SMILES: CCC(C)NC(=O)c1sc(-c2cccnc2)nc1Cl] | LCMS_1: 296 (M + 1) |

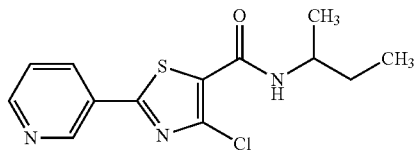
(1.022)
| Compound No. | Structure | Phys. Data |
|---|---|---|
| 1.023 | 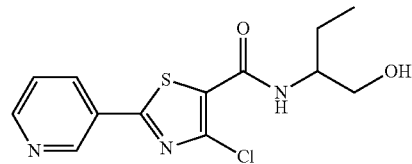 [SMILES: CCC(CO)NC(=O)c1sc(-c2cccnc2)nc1Cl] | LCMS_1: 312 (M + 1) |
| 1.024 | 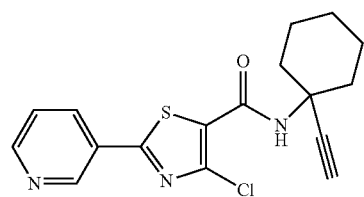 [SMILES: C#CC1(NC(=O)c2sc(-c3cccnc3)nc2Cl)CCCCC1] | LCMS_1: 346 (M + 1) |
| 1.025 | 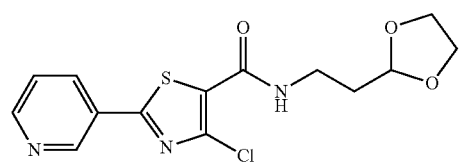 [SMILES: O=C(NCCC1OCCO1)c1sc(-c2cccnc2)nc1Cl] | LCMS_1: 340 (M + 1) |
| 1.026 | 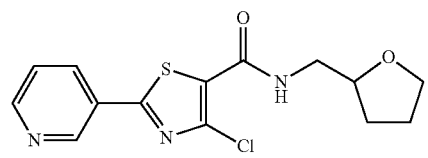 | LCMS_1: 324 (M + 1) |
| 1.027 | 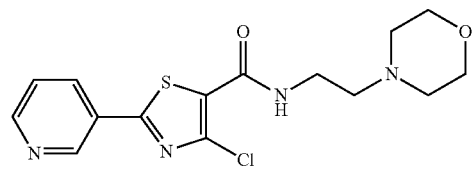 [SMILES: O=C(NCCN1CCOCC1)c1sc(-c2cccnc2)nc1Cl] | LCMS_1: 353 (M + 1) |
| 1.028 | 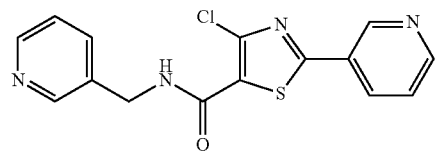 [SMILES: O=C(NCc1cccnc1)c1sc(-c2cccnc2)nc1Cl] | LCMS_1: 331 (M + 1) |
| 1.029 | 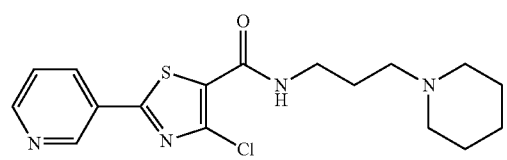 [SMILES: O=C(NCCCN1CCCCC1)c1sc(-c2cccnc2)nc1Cl] | LCMS_1: 365 (M + 1) |
| 1.030 | 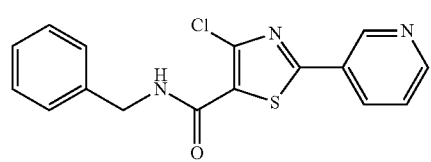 [SMILES: O=C(NCc1ccccc1)c1sc(-c2cccnc2)nc1Cl] | LCMS_1: 330 (M + 1) |

(1.022)
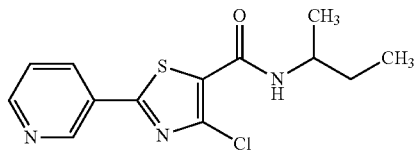
| Compound No. | Structure | Phys. Data |
|---|---|---|
| 1.031 | 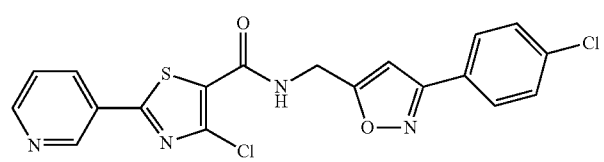 [SMILES: O=C(NCc1cc(-c2ccc(Cl)cc2)no1)c1sc(-c2cccnc2)nc1Cl] | LCMS_1: 431 (M + 1) |
| 1.032 | 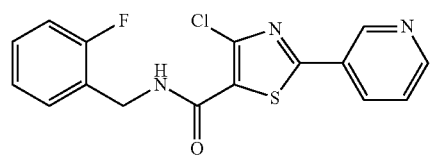 | LCMS_1: 348 (M + 1) |
| 1.033 | 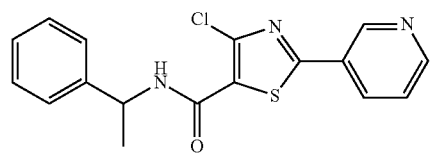 [SMILES: CC(NC(=O)c1sc(-c2cccnc2)nc1Cl)c1ccccc1] | LCMS_1: 344 (M + 1) |
| 1.034 | 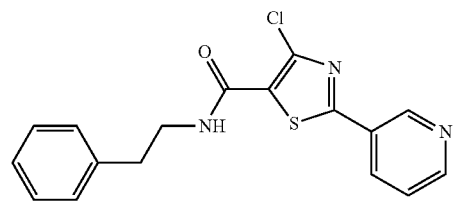 [SMILES: O=C(NCCc1ccccc1)c1sc(-c2cccnc2)nc1Cl] | LCMS_1: 344 (M + 1) |
| 1.035 | 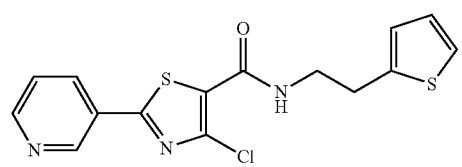 [SMILES: O=C(NCCc1cccs1)c1sc(-c2cccnc2)nc1Cl] | LCMS_1: 350 (M + 1) |
| 1.036 | 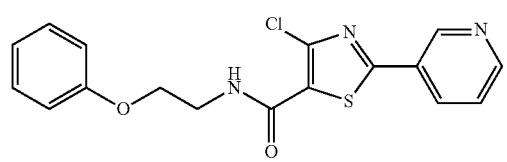 [SMILES: O=C(NCCOc1ccccc1)c1sc(-c2cccnc2)nc1Cl] | LCMS_1: 360 (M + 1) |
| 1.037 | 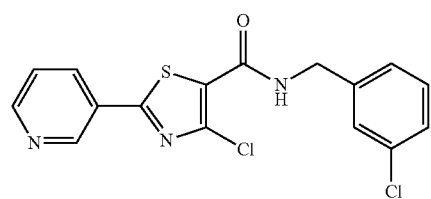 [SMILES: O=C(NCc1cccc(Cl)c1)c1sc(-c2cccnc2)nc1Cl] | LCMS_1: 364 (M + 1) |

(1.022)
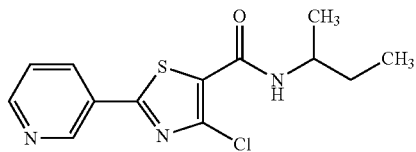
| Compound No. | Structure | Phys. Data |
|---|---|---|
| 1.038 | 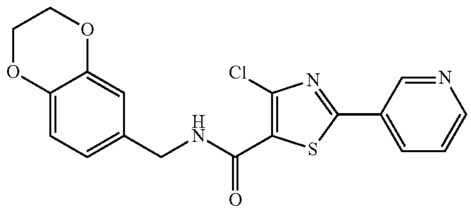 [SMILES: O=C(NCc1ccc2c(c1)OCCO2)c1sc(-c2cccnc2)nc1Cl] | LCMS_1: 388 (M + 1) |
| 1.039 | 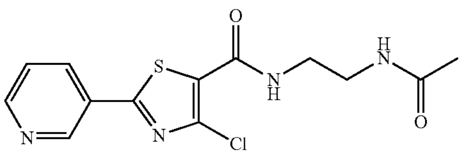 [SMILES: CC(=O)NCCNC(=O)c1sc(-c2cccnc2)nc1Cl] | LCMS_1: 325 (M + 1) |
| 1.040 | 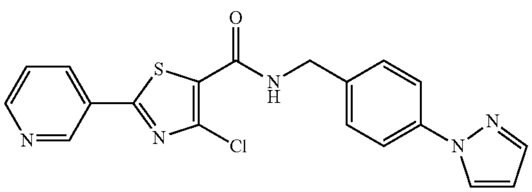 [SMILES: O=C(NCc1ccc(-n2cccn2)cc1)c1sc(-c2cccnc2)nc1Cl] | LCMS_1: 396 (M + 1) |
| 1.041 | 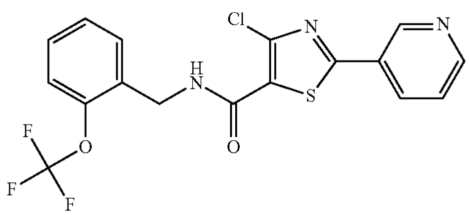 [SMILES: O=C(NCc1ccccc1OC(F)(F)F)c1sc(-c2cccnc2)nc1Cl] | LCMS_1: 414 (M + 1) |
| 1.042 | 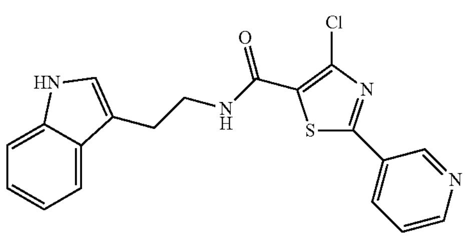 [SMILES: O=C(NCCc1c[nH]c2ccccc12)c1sc(-c2cccnc2)nc1Cl] | LCMS_1: 383 (M + 1) |
| 1.043 | 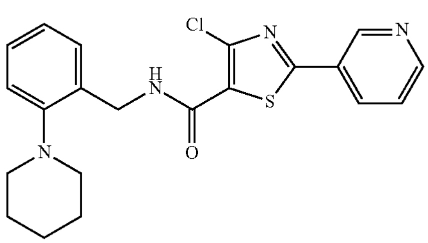 [SMILES: O=C(NCc1ccccc1N1CCCCC1)c1sc(-c2cccnc2)nc1Cl] | LCMS_1: 413 (M + 1) |

-continued
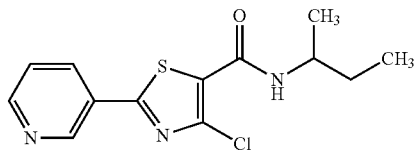
(1.022)
| Compound No. | Structure | Phys. Data |
|---|---|---|
| 1.044 | 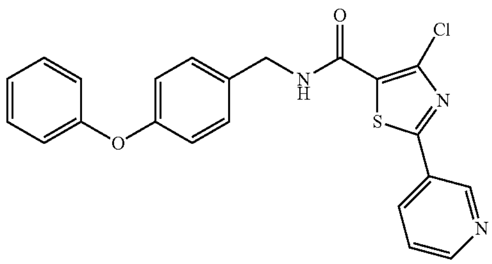 [SMILES: O=C(NCc1ccc(Oc2ccccc2)cc1)c1sc(-c2cccnc2)nc1Cl] | LCMS_1: 422 (M + 1) |
| 1.045 | 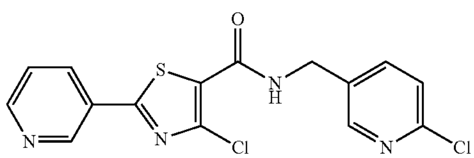 [SMILES: O=C(NCc1ccc(Cl)nc1)c1sc(-c2cccnc2)nc1Cl] | LCMS_1: 365 (M + 1) |
| 1.046 | 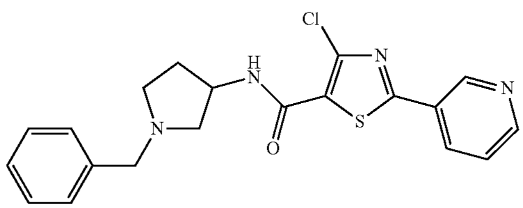 [SMILES: O=C(NC1CCN(Cc2ccccc2)C1)c1sc(-c2cccnc2)nc1Cl] | LCMS_1: 399 (M + 1) |
| 1.047 | 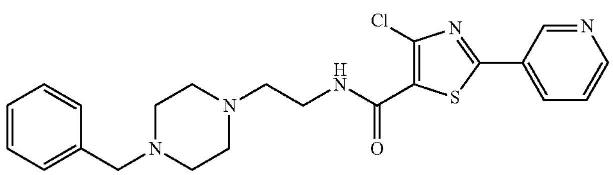 [SMILES: O=C(NCCN1CCN(Cc2ccccc2)CC1)c1sc(-c2cccnc2)nc1Cl] | LCMS_1: 442 (M + 1) |
| 1.048 | 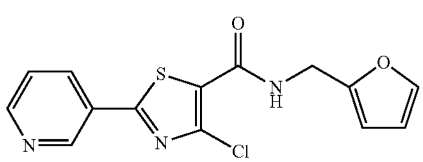 [SMILES: O=C(NCc1ccco1)c1sc(-c2cccnc2)nc1Cl] | LCMS_1: 320 (M + 1) |
| 1.049 | 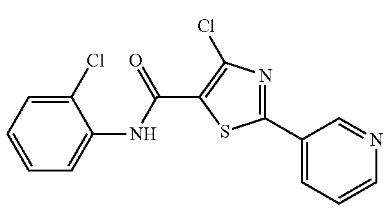 [SMILES: O=C(Nc1ccccc1Cl)c1sc(-c2cccnc2)nc1Cl] | LCMS_1: 350 (M + 1) |
| 1.050 | 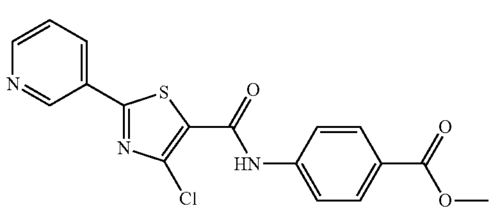 [SMILES: COC(=O)c1ccc(NC(=O)c2sc(-c3cccnc3)nc2Cl)cc1] | LCMS_1: 374 (M + 1) |

(1.022)
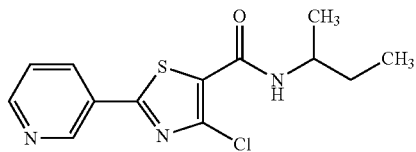
| Compound No. | Structure | Phys. Data |
|---|---|---|
| 1.051 | 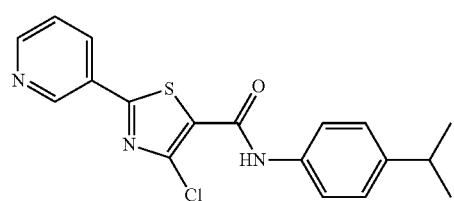 [SMILES: CC(C)c1ccc(NC(=O)c2sc(-c3cccnc3)nc2Cl)cc1] | LCMS_1: 358 (M + 1) |
| 1.052 | 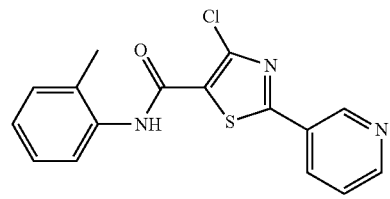 [SMILES: Cc1ccccc1NC(=O)c1sc(-c2cccnc2)nc1Cl] | LCMS_1: 330 (M + 1) |
| 1.053 | 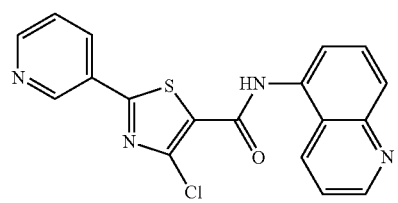 [SMILES: O=C(Nc1cccc2ncccc12)c1sc(-c2cccnc2)nc1Cl] | LCMS_1: 367 (M + 1) |
| 1.054 | 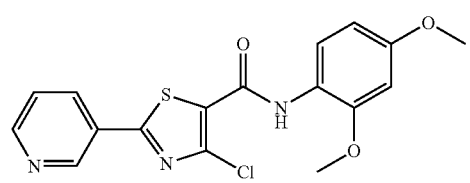 [SMILES: COc1ccc(NC(=O)c2sc(-c3cccnc3)nc2Cl)c(OC)c1] | LCMS_1: 376 (M + 1) |
| 1.055 | 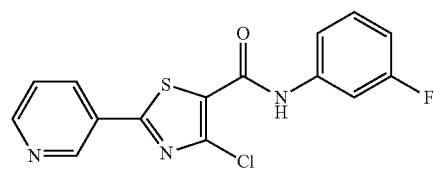 [SMILES: O=C(Nc1cccc(F)c1)c1sc(-c2cccnc2)nc1Cl] | LCMS_1: 334 (M + 1) |
| 1.056 | 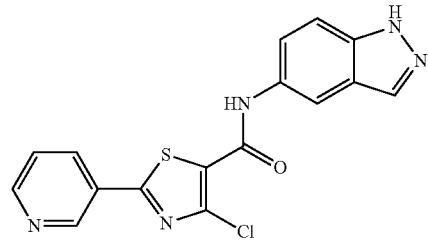 [SMILES: O=C(Nc1ccc2[nH]ncc2c1)c1sc(-c2cccnc2)nc1Cl] | LCMS_1: 356 (M + 1) |

(1.022)
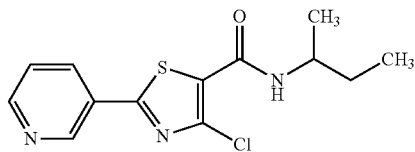
| Compound No. | Structure | Phys. Data |
|---|---|---|
| 1.057 | 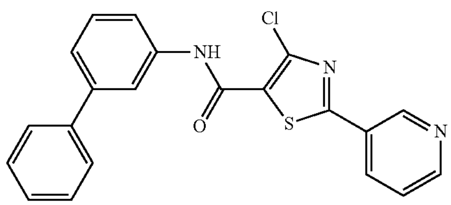 [SMILES: O=C(Nc1cccc(-c2ccccc2)c1)c1sc(-c2cccnc2)nc1Cl] | LCMS_1: 392 (M + 1) |
| 1.058 | 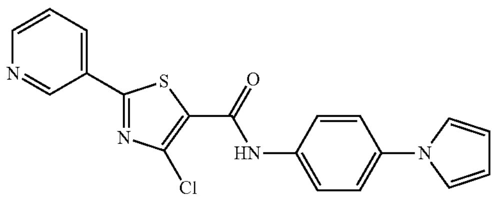 [SMILES: O=C(Nc1ccc(-n2cccc2)cc1)c1sc(-c2cccnc2)nc1Cl] | LCMS_1: 381 (M + 1) |
| 1.059 | 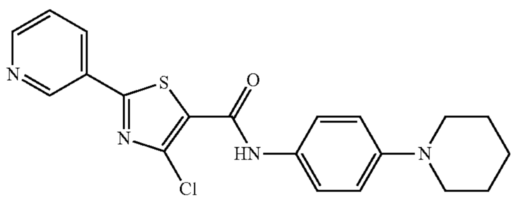 [SMILES: O=C(Nc1ccc(N2CCCCC2)cc1)c1sc(-c2cccnc2)nc1Cl] | LCMS_1: 399 (M + 1) |
| 1.060 | 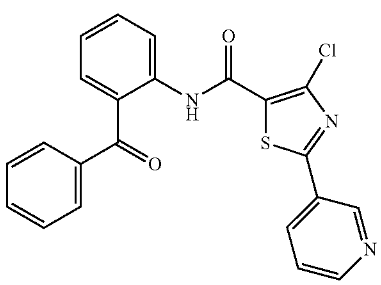 [SMILES: O=C(c1ccccc1)c1ccccc1NC(=O)c1sc(-c2cccnc2)nc1Cl] | LCMS_1: 420 (M + 1) |
| 1.061 | 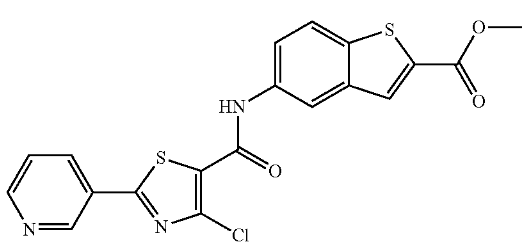 [SMILES: COC(=O)c1cc2cc(NC(=O)c3sc(-c4cccnc4)nc3Cl)ccc2s1] | LCMS_1: 430 (M + 1) |
| 1.062 | 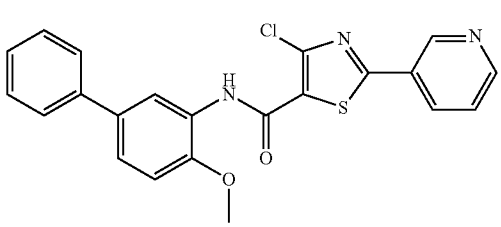 [SMILES: COc1ccc(-c2ccccc2)cc1NC(=O)c1sc(-c2cccnc2)nc1Cl] | LCMS_1: 422 (M + 1) |

(1.022)
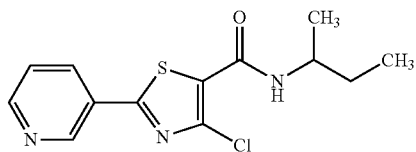
| Compound No. | Structure | Phys. Data |
|---|---|---|
| 1.063 | 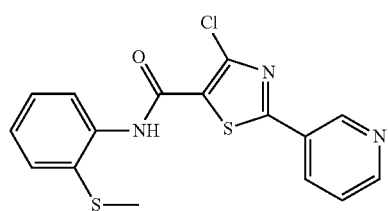 [SMILES: CSc1ccccc1NC(=O)c1sc(-c2cccnc2)nc1Cl] | LCMS_1: 362 (M + 1) |
| 1.064 | 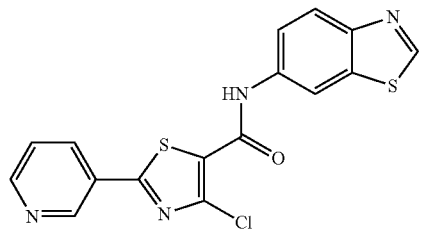 [SMILES: O=C(Nc1ccc2ncsc2c1)c1sc(-c2cccnc2)nc1Cl] | LCMS_1: 373 (M + 1) |
| 1.065 | 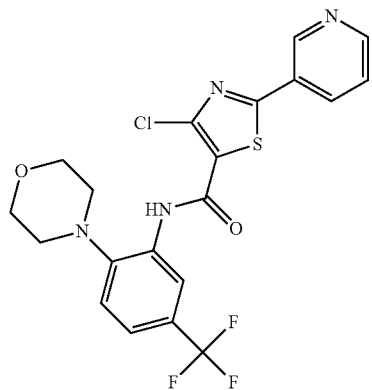 [SMILES: O=C(Nc1cc(C(F)(F)F)ccc1N1CCOCC1)c1sc(-c2cccnc2)nc1Cl] | LCMS_1: 469 (M + 1) |
| 1.066 | 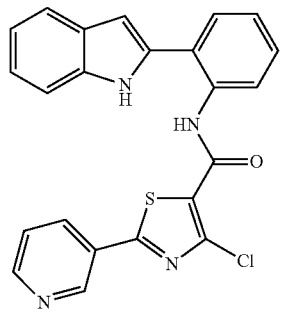 [SMILES: O=C(Nc1ccccc1-c1cc2ccccc2[nH]1)c1sc(-c2cccnc2)nc1Cl] | LCMS_1: 431 (M + 1) |

(1.022)
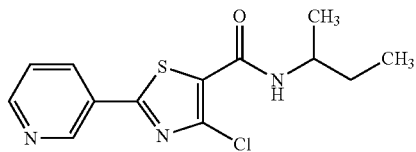
| Compound No. | Structure | Phys. Data |
|---|---|---|
| 1.067 | 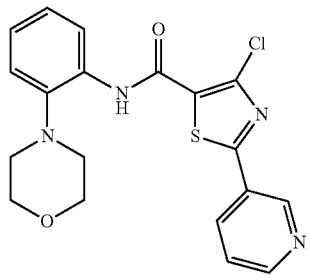 [SMILES: O=C(Nc1ccccc1N1CCOCC1)c1sc(-c2cccnc2)nc1Cl] | LCMS_1: 401 (M + 1) |
| 1.068 | 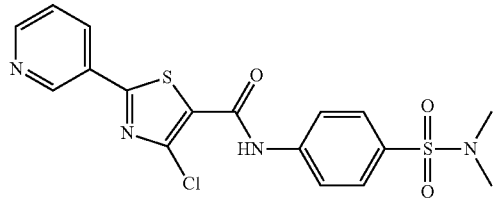 [SMILES: CN(C)S(=O)(=O)c1ccc(NC(=O)c2sc(-c3cccnc3)nc2Cl)cc1] | LCMS_1: 423 (M + 1) |
| 1.069 | 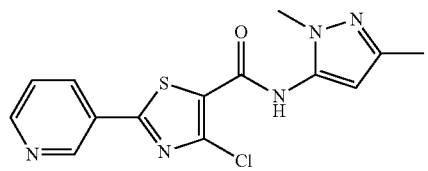 [SMILES: Cc1cc(NC(=O)c2sc(-c3cccnc3)nc2Cl)n(C)n1] | LCMS_1: 334 (M + 1) |
| 1.070 | 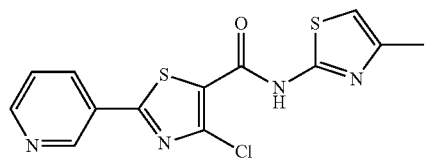 [SMILES: Cc1csc(NC(=O)c2sc(-c3cccnc3)nc2Cl)n1] | LCMS_1: 337 (M + 1) |
| 1.071 | 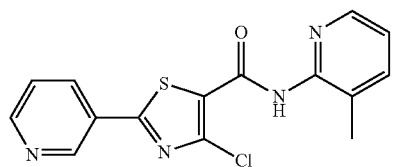 [SMILES: Cc1cccnc1NC(=O)c1sc(-c2cccnc2)nc1Cl] | LCMS_1: 331 (M + 1) |
| 1.072 | 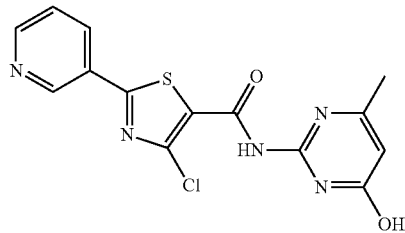 [SMILES: Cc1cc(O)nc(NC(=O)c2sc(-c3cccnc3)nc2Cl)n1] | LCMS_1: 348 (M + 1) |

(1.022)
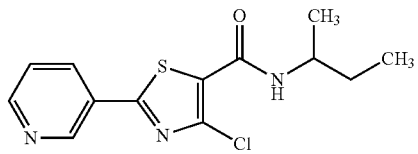
| Compound No. | Structure | Phys. Data |
|---|---|---|
| 1.073 | 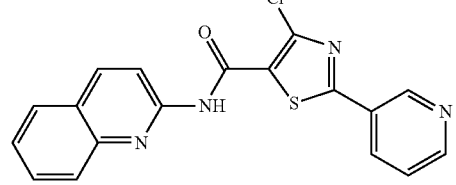 | LCMS_1: 367 (M + 1) |
| 1.074 | 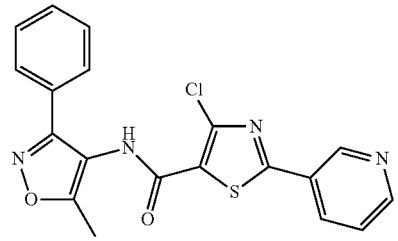 [SMILES: Cc1onc(-c2ccccc2)c1NC(=O)c1sc(-c2cccnc2)nc1Cl] | LCMS_1: 397 (M + 1) |
| 1.075 | 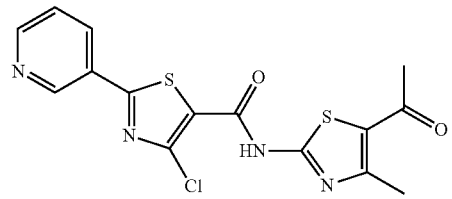 [SMILES: CC(=O)c1sc(NC(=O)c2sc(-c3cccnc3)nc2Cl)nc1C] | LCMS_1: 379 (M + 1) |
| 1.076 | 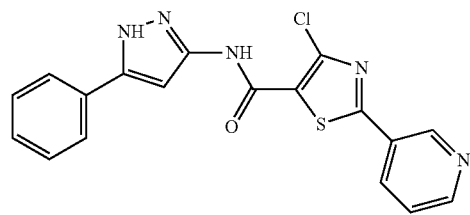 [SMILES: O=C(Nc1cc(-c2ccccc2)[nH]n1)c1sc(-c2cccnc2)nc1Cl] | LCMS_1: 382 (M + 1) |
| 1.077 | 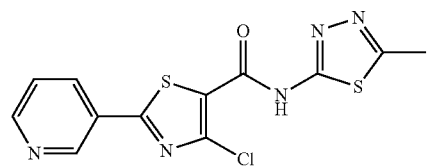 [SMILES: Cc1nnc(NC(=O)c2sc(-c3cccnc3)nc2Cl)s1] | LCMS_1: 338 (M + 1) |
| 1.078 | 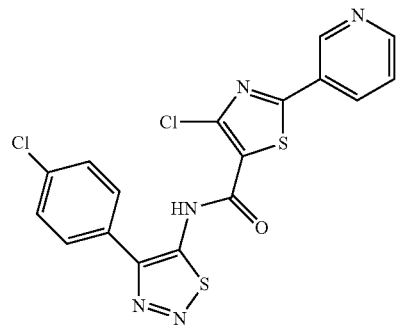 [SMILES: O=C(Nc1snnc1-c1ccc(Cl)cc1)c1sc(-c2cccnc2)nc1Cl] | LCMS_1: 434 (M + 1) |

(1.022)
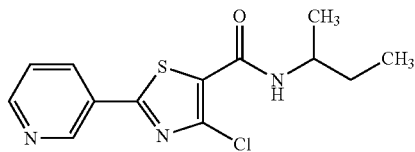
| Compound No. | Structure | Phys. Data |
|---|---|---|
| 1.079 | 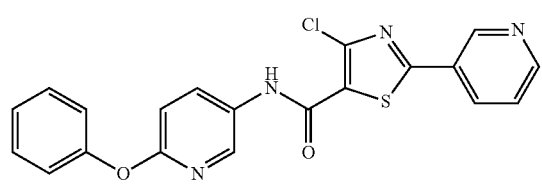 [SMILES: O=C(Nc1ccc(Oc2ccccc2)nc1)c1sc(-c2cccnc2)nc1Cl] | LCMS_1: 409 (M + 1) |
| 1.080 | 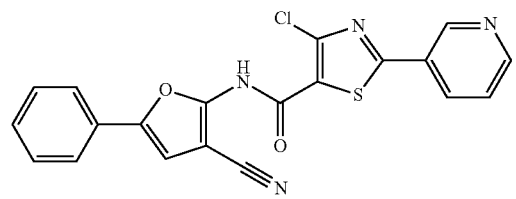 [SMILES: N#Cc1cc(-c2ccccc2)oc1NC(=O)c1sc(-c2cccnc2)nc1Cl] | LCMS_1: 407 (M + 1) |
| 1.081 | 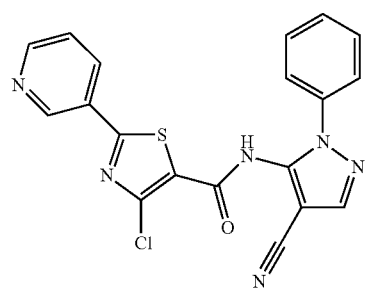 [SMILES: N#Cc1cnn(-c2ccccc2)c1NC(=O)c1sc(-c2cccnc2)nc1Cl] | LCMS_1: 407 (M + 1) |
| 1.082 | 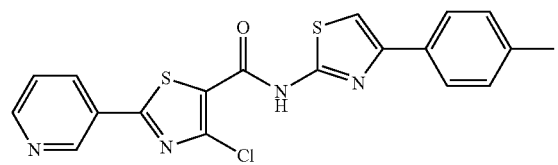 [SMILES: Cc1ccc(-c2csc(NC(=O)c3sc(-c4cccnc4)nc3Cl)n2)cc1] | LCMS_1: 413 (M + 1) |
| 1.083 | 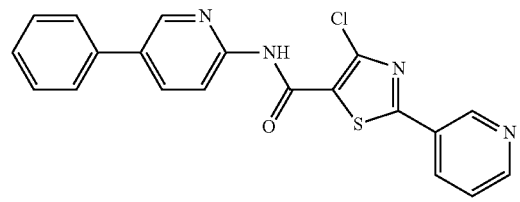 [SMILES: O=C(Nc1ccc(-c2ccccc2)cn1)c1sc(-c2cccnc2)nc1Cl] | LCMS_1: 393 (M + 1) |
| 1.084 | 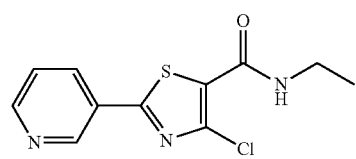 [SMILES: CCNC(=O)c1sc(-c2cccnc2)nc1Cl] | LCMS_1: 268 (M + 1) |

(1.022)
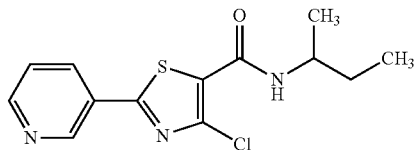
| Compound No. | Structure | Phys. Data |
|---|---|---|
| 1.085 | 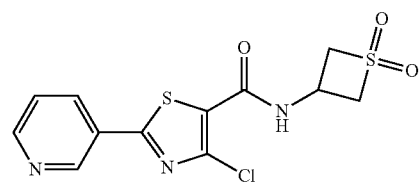 [SMILES: O=C(NC1CS(=O)(=O)C1)c1sc(-c2cccnc2)nc1Cl] | LCMS_1: 344 (M + 1) |
| 1.086 | 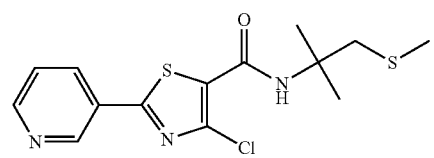 | LCMS_1: 342 (M + 1) |
| 1.087 | 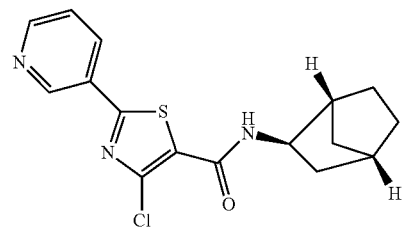 [SMILES: O=C(N[C@@H]1C[C@H]2CC[C@@H]1C2)c1sc(-c2cccnc2)nc1Cl] | LCMS_1: 334 (M + 1) |
| 1.088 | 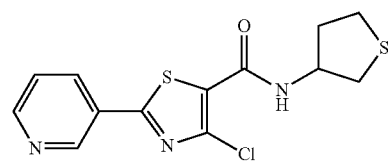 [SMILES: O=C(NC1CCSC1)c1sc(-c2cccnc2)nc1Cl] | LCMS_1: 326 (M + 1) |
| 1.089 | 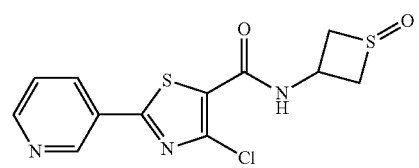 [SMILES: O=C(NC1CS(=O)C1)c1sc(-c2cccnc2)nc1Cl] | LCMS_1: 328 (M + 1), cis |
| 1.090 | 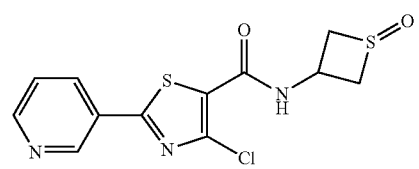 [SMILES: O=C(NC1CS(=O)C1)c1sc(-c2cccnc2)nc1Cl] | LCMS_1: 328 (M + 1), trans |
| 1.091 | 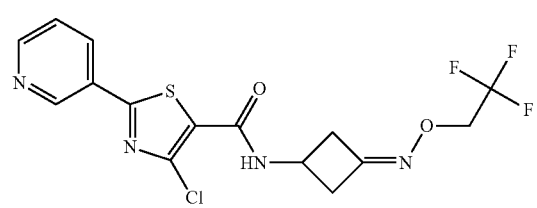 [SMILES: O=C(NC1CC(=NOCC(F)(F)F)C1)c1sc(-c2cccnc2)nc1Cl] | LCMS_1: 405 (M + 1) |

(1.022)
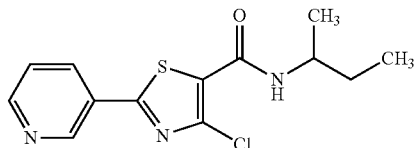
| Compound No. | Structure | Phys. Data |
|---|---|---|
| 1.092 | 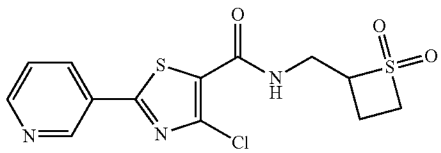 [SMILES: O=C(NCC1CCS1(=O)=O)c1sc(-c2cccnc2)nc1Cl] | LCMS_1: 358 (M + 1) |
| 1.093 | 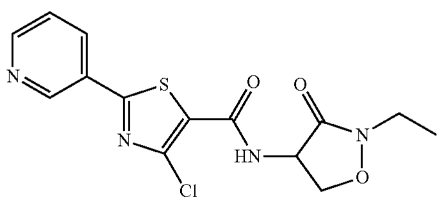 [SMILES: CCN1OCC(NC(=O)c2sc(-c3cccnc3)nc2Cl)C1=O] | LCMS_1: 353 (M + 1) |
| 1.094 | 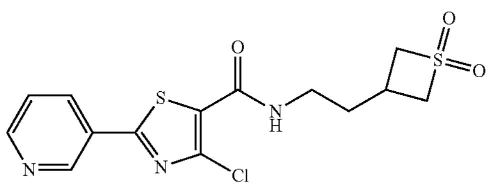 [SMILES: O=C(NCCC1CS(=O)(=O)C1)c1sc(-c2cccnc2)nc1Cl] | LCMS_1: 372 (M + 1) |
| 1.095 | 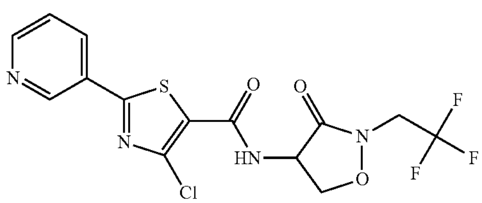 [SMILES: O=C(NC1CON(CC(F)(F)F)C1=O)c1sc(-c2cccnc2)nc1Cl] | LCMS_1: 407 (M + 1) |
| 1.096 | 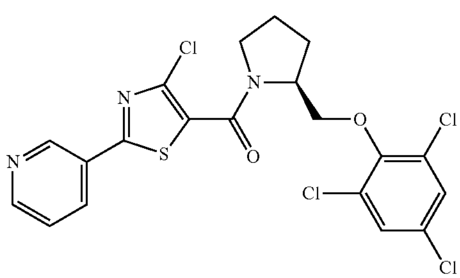 [SMILES: O=C(c1sc(-c2cccnc2)nc1Cl)N1CCC[C@H]1COc1c(Cl)cc(Cl)cc1Cl] | LCMS_1: 502 (M + 1) |
| 1.097 | 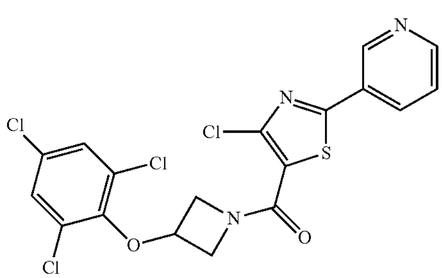 [SMILES: O=C(c1sc(-c2cccnc2)nc1Cl)N1CC(Oc2c(Cl)cc(Cl)cc2Cl)C1] | LCMS_1: 474 (M + 1) |

-continued
(1.022)
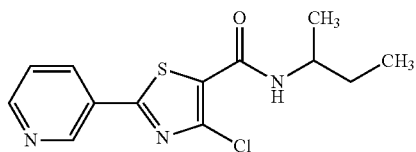
| Compound No. | Structure | Phys. Data |
|---|---|---|
| 1.098 | 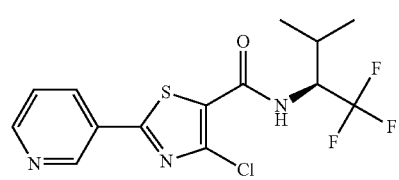 [SMILES: CC(C)[C@H](NC(=O)c1sc(-c2cccnc2)nc1Cl)C(F)(F)F] | LCMS_1: 364 (M + 1) |
| 1.099 | 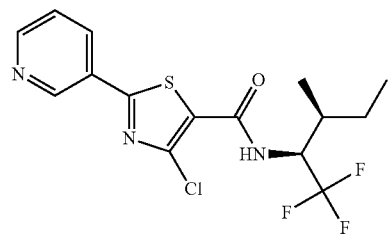 [SMILES: CC[C@H](C)[C@H](NC(=O)c1sc(-c2cccnc2)nc1Cl)C(F)(F)F] | LCMS_1: 378 (M + 1) |
| 1.100 | 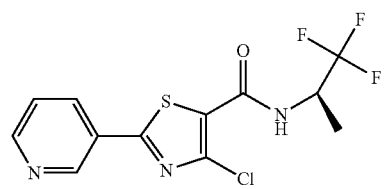 [SMILES: C[C@@H](NC(=O)c1sc(-c2cccnc2)nc1Cl)C(F)(F)F] | LCMS_1: 336 (M + 1) |
| 1.101 | 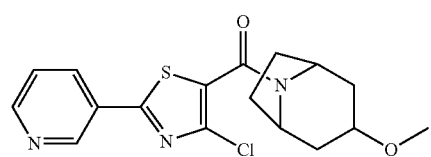 [SMILES: COC1CC2CCC(C1)N2C(=O)c1sc(-c2cccnc2)nc1Cl] | LCMS_1: 364 (M + 1) |
| 1.102 | 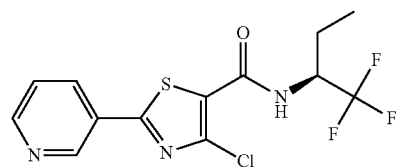 [SMILES: CC[C@H](NC(=O)c1sc(-c2cccnc2)nc1Cl)C(F)(F)F] | LCMS_1: 350 (M + 1) |
| 1.103 | 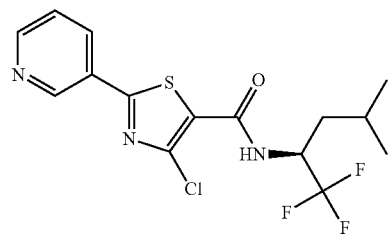 [SMILES: CC(C)C[C@H](NC(=O)c1sc(-c2cccnc2)nc1Cl)C(F)(F)F] | LCMS_1: 378 (M + 1) |

(1.022)
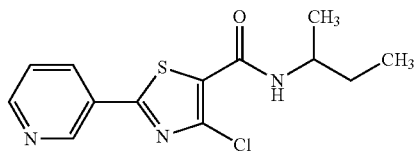
| Compound No. | Structure | Phys. Data |
|---|---|---|
| 1.104 | 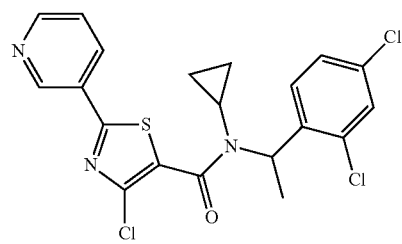 [SMILES: CC(c1ccc(Cl)cc1Cl)N(C(=O)c1sc(-c2cccnc2)nc1Cl)C1CC1] | LCMS_1: 452 (M + 1) |
| 1.105 | 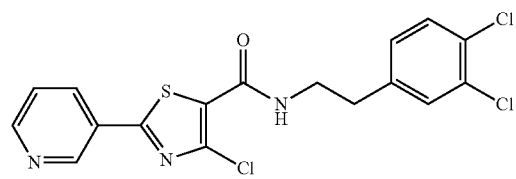 [SMILES: O=C(NCCc1ccc(Cl)c(Cl)c1)c1sc(-c2cccnc2)nc1Cl] | LCMS_1: 412 (M + 1) |
| 1.106 | 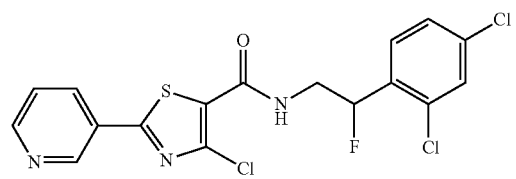 [SMILES: O=C(NCC(F)c1ccc(Cl)cc1Cl)c1sc(-c2cccnc2)nc1Cl] | LCMS_1: 430 (M + 1) |
| 1.107 | 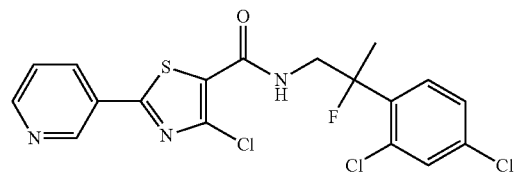 [SMILES: CC(F)(CNC(=O)c1sc(-c2cccnc2)nc1Cl)c1ccc(Cl)cc1Cl] | LCMS_1: 444 (M + 1) |
| 1.108 | 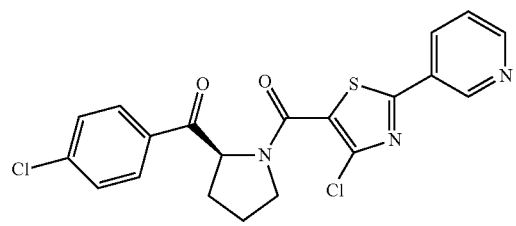 [SMILES: O=C(c1ccc(Cl)cc1)[C@@H]1CCCN1C(=O)c1sc(-c2cccnc2)nc1Cl] | LCMS_1: 432 (M + 1) |
| 1.109 | 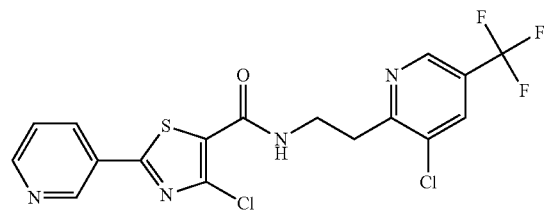 [SMILES: O=C(NCCc1ncc(C(F)(F)F)cc1Cl)c1sc(-c2cccnc2)nc1Cl] | LCMS_1: 447 (M + 1) |

-continued
(1.022)
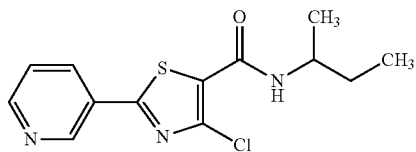
| Compound No. | Structure | Phys. Data |
|---|---|---|
| 1.110 | 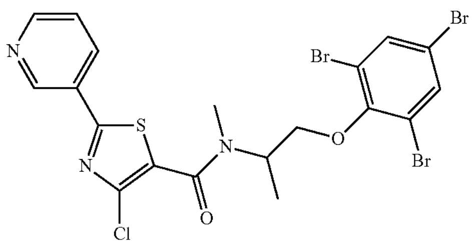 | LCMS_1: 647 (M + 1) |
| 1.111 | 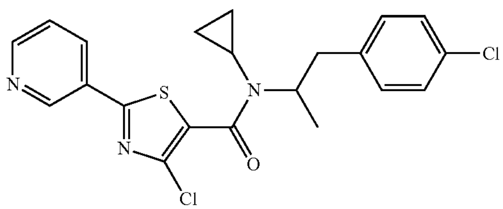 [SMILES: CC(Cc1ccc(Cl)cc1)N(C(=O)c1sc(-c2cccnc2)nc1Cl)C1CC1] | LCMS_1: 432 (M + 1) |
| 1.112 | 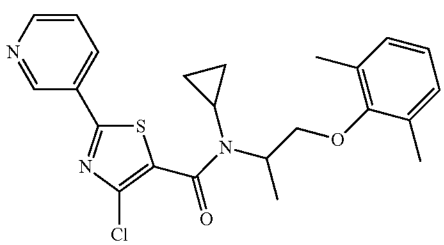 [SMILES: Cc1cccc(C)c1OCC(C)N(C(=O)c1sc(-c2cccnc2)nc1Cl)C1CC1] | LCMS_1: 442 (M + 1) |
| 1.113 | 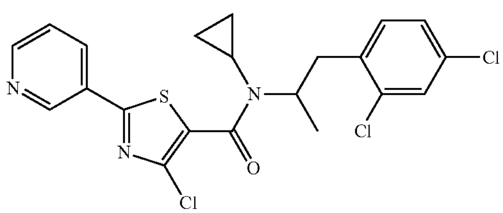 [SMILES: CC(Cc1ccc(Cl)cc1Cl)N(C(=O)c1sc(-c2cccnc2)nc1Cl)C1CC1] | LCMS_1: 466 (M + 1) |
| 1.114 | 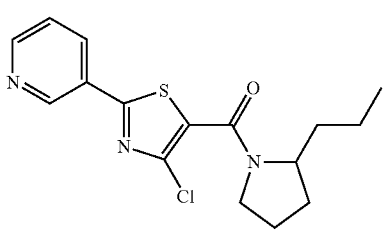 [SMILES: CCCC1CCCN1C(=O)c1sc(-c2cccnc2)nc1Cl] | LCMS_1: 336 (M + 1) |
| 1.115 | 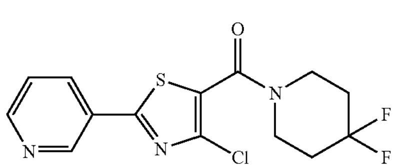 [SMILES: O=C(c1sc(-c2cccnc2)nc1Cl)N1CCC(F)(F)CC1] | LCMS_1: 344 (M + 1) |

(1.022)
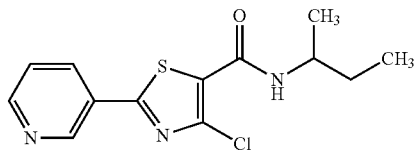
| Compound No. | Structure | Phys. Data |
|---|---|---|
| 1.116 | 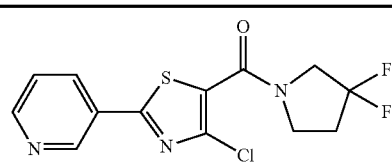 | LCMS_1: 330 (M + 1) |
| 1.117 | 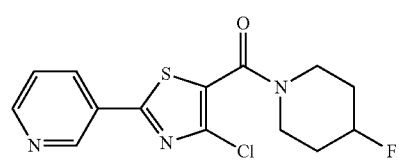 [SMILES: O=C(c1sc(-c2cccnc2)nc1Cl)N1CCC(F)CC1] | LCMS_1: 326 (M + 1) |
| 1.118 | 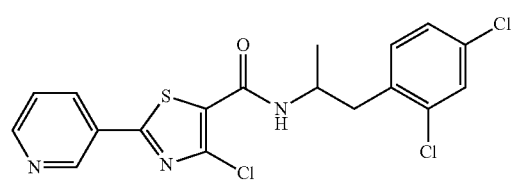 [SMILES: CC(Cc1ccc(Cl)cc1Cl)NC(=O)c1sc(-c2cccnc2)nc1Cl] | LCMS_1: 426 (M + 1) |
| 1.119 | 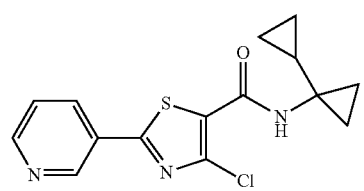 [SMILES: O=C(NC1(C2CC2)CC1)c1sc(-c2cccnc2)nc1Cl] | LCMS_1: 320 (M + 1) |
| 1.120 | 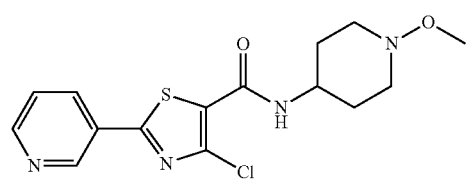 [SMILES: CON1CCC(NC(=O)c2sc(-c3cccnc3)nc2Cl)CC1] | LCMS_1: 353 (M + 1) |
| 1.121 | 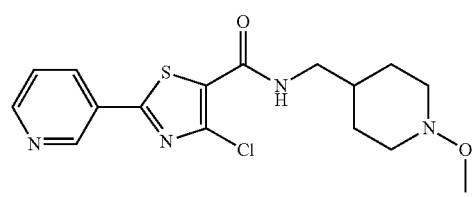 [SMILES: CON1CCC(CNC(=O)c2sc(-c3cccnc3)nc2Cl)CC1] | LCMS_1: 367 (M + 1) |
| 1.122 | 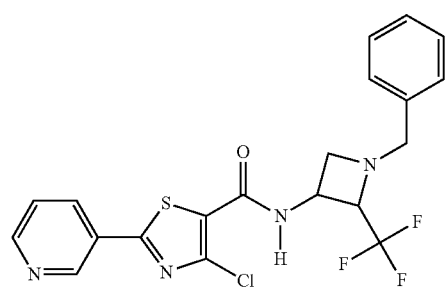 [SMILES: O=C(NC1CN(Cc2ccccc2)C1C(F)(F)F)c1sc(-c2cccnc2)nc1Cl] | LCMS_1: 453 (M + 1) |

(1.022)
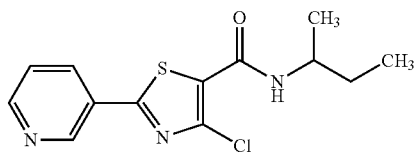
| Compound No. | Structure | Phys. Data |
|---|---|---|
| 1.123 | 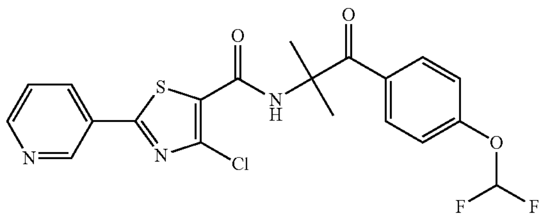 [SMILES: CC(C)(NC(=O)c1sc(-c2cccnc2)nc1Cl)C(=O)c1ccc(OC(F)F)cc1] | LCMS_1: 452 (M + 1) |
| 1.124 | 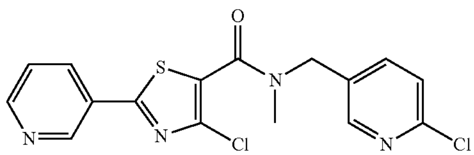 [SMILES: CN(Cc1ccc(Cl)nc1)C(=O)c1sc(-c2cccnc2)nc1Cl] | LCMS_1: 379 (M + 1) |
| 1.125 | 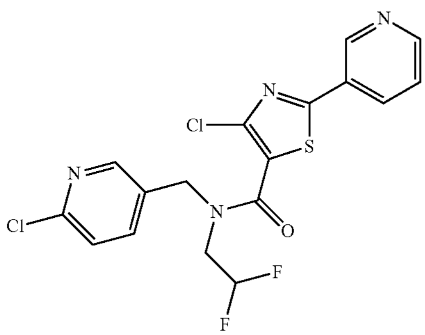 [SMILES: O=C(c1sc(-c2cccnc2)nc1Cl)N(Cc1ccc(Cl)nc1)CC(F)F] | LCMS_1: 429 (M + 1) |
| 1.126 | 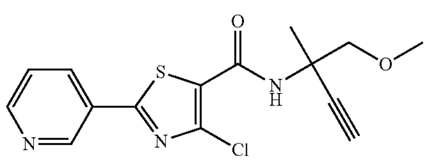 [SMILES: C#CC(C)(COC)NC(=O)c1sc(-c2cccnc2)nc1Cl] | LCMS_1: 336 (M + 1) |
| 1.127 | 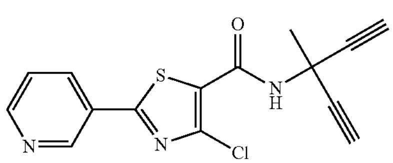 [SMILES: C#CC(C)(C#C)NC(=O)c1sc(-c2cccnc2)nc1Cl] | LCMS_1: 316 (M + 1) |
| 1.128 | 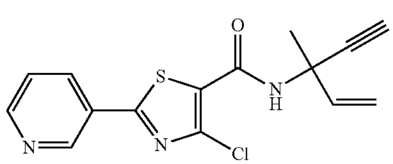 [SMILES: C#CC(C)(C=C)NC(=O)c1sc(-c2cccnc2)nc1Cl] | LCMS_1: 318 (M + 1) |
| 1.129 | 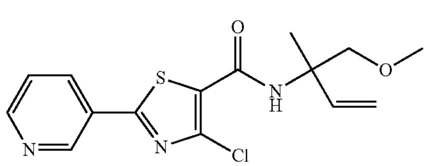 [SMILES: C=CC(C)(COC)NC(=O)c1sc(-c2cccnc2)nc1Cl] | LCMS_1: 338 (M + 1) |

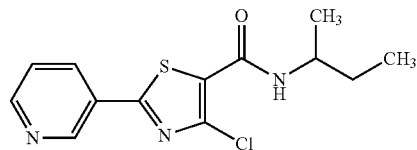
(1.022)
| Compound No. | Structure | Phys. Data |
|---|---|---|
| 1.130 | 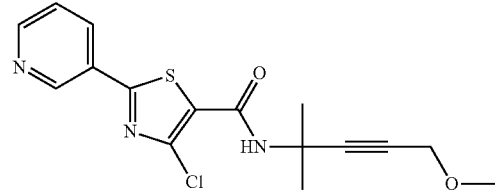 [SMILES: COCC#CC(C)(C)NC(=O)c1sc(-c2cccnc2)nc1Cl] | LCMS_1: 350 (M + 1) |
| 1.131 | 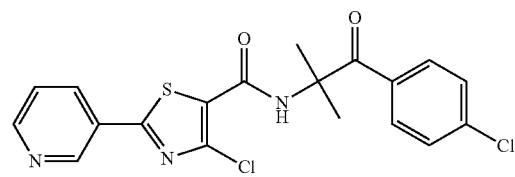 [SMILES: CC(C)(NC(=O)c1sc(-c2cccnc2)nc1Cl)C(=O)c1ccc(Cl)cc1] | LCMS_1: 420 (M + 1) |
| 1.132 | 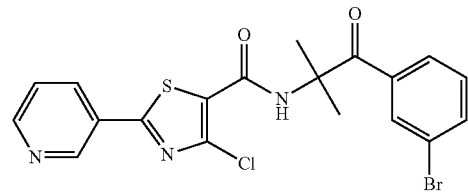 [SMILES: CC(C)(NC(=O)c1sc(-c2cccnc2)nc1Cl)C(=O)c1cccc(Br)c1] | LCMS_1: 464 (M + 1) |
| 1.133 | 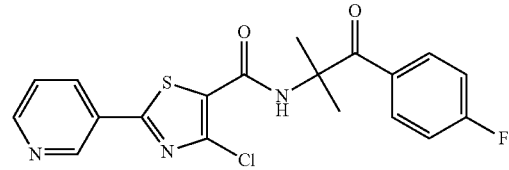 [SMILES: CC(C)(NC(=O)c1sc(-c2cccnc2)nc1Cl)C(=O)c1ccc(F)cc1] | LCMS_1: 404 (M + 1) |
| 1.134 | 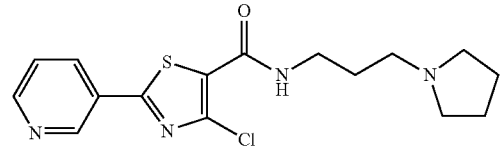 [SMILES: O=C(NCCCN1CCCC1)c1sc(-c2cccnc2)nc1Cl] | LCMS_1: 351 (M + 1) |
| 1.135 | 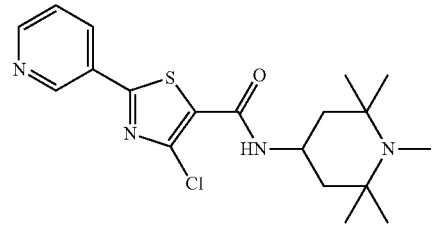 [SMILES: CN1C(C)(C)CC(NC(=O)c2sc(-c3cccnc3)nc2Cl)CC1(C)C] | LCMS_1: 393 (M + 1) |
| 1.136 | 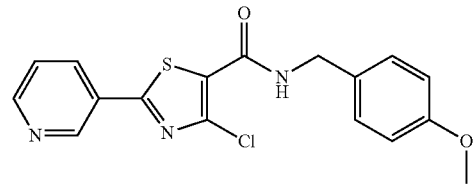 [SMILES: COc1ccc(CNC(=O)c2sc(-c3cccnc3)nc2Cl)cc1] | LCMS_1: 360 (M + 1) |

(1.022)
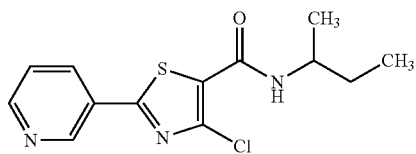
| Compound No. | Structure | Phys. Data |
|---|---|---|
| 1.137 | 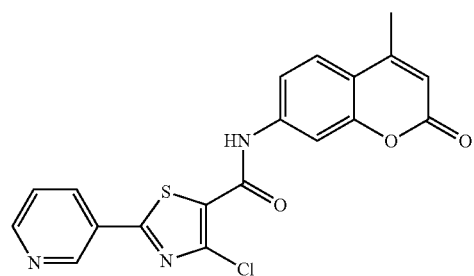 [SMILES: Cc1cc(=O)oc2cc(NC(=O)c3sc(-c4cccnc4)nc3Cl)ccc12] | LCMS_1: 398 (M + 1) |
| 1.138 | 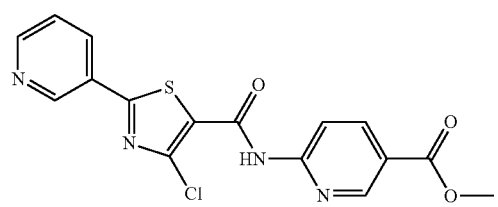 [SMILES: COC(=O)c1ccc(NC(=O)c2sc(-c3cccnc3)nc2Cl)nc1] | LCMS_1: 375 (M + 1) |
| 1.139 | 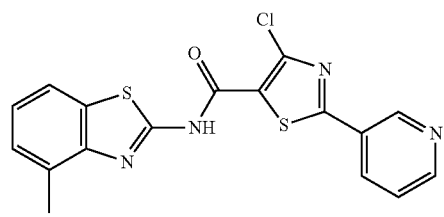 [SMILES: Cc1cccc2sc(NC(=O)c3sc(-c4cccnc4)nc3Cl)nc12] | LCMS_1: 387 (M + 1) |
| 1.140 | 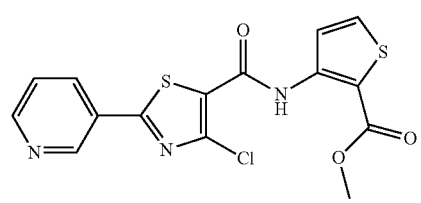 [SMILES: COC(=O)c1sccc1NC(=O)c1sc(-c2cccnc2)nc1Cl] | LCMS_1: 380 (M + 1) |
| 1.141 | 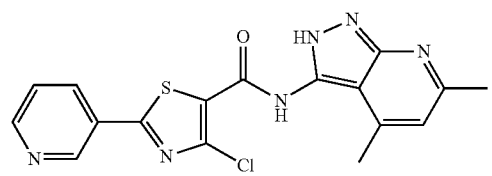 [SMILES: Cc1cc(C)c2c(NC(=O)c3sc(-c4cccnc4)nc3Cl)[nH]nc2n1] | LCMS_1: 385 (M + 1) |
| 1.142 | 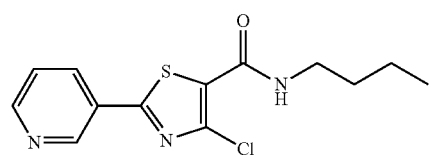 [SMILES: CCCCNC(=O)c1sc(-c2cccnc2)nc1Cl] | LCMS_1: 296 (M + 1) |

(1.022)
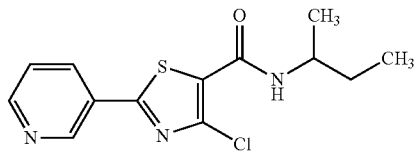
| Compound No. | Structure | Phys. Data |
|---|---|---|
| 1.143 | 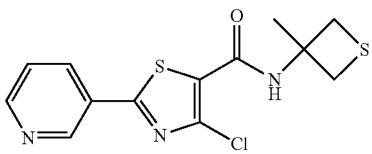 [SMILES: CC1(NC(=O)c2sc(-c3cccnc3)nc2Cl)CSC1] | LCMS_1: 326 (M + 1) |
| 1.144 | 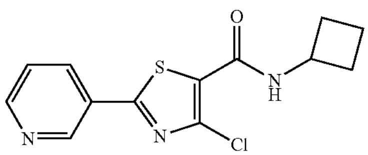 [SMILES: O=C(NC1CCC1)c1sc(-c2cccnc2)nc1Cl] | LCMS_1: 294 (M + 1) |
| 1.145 | 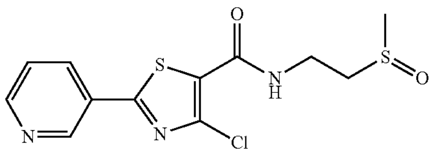 [SMILES: CS(=O)CCNC(=O)c1sc(-c2cccnc2)nc1Cl] | LCMS_1: 330 (M + 1) |
| 1.146 | 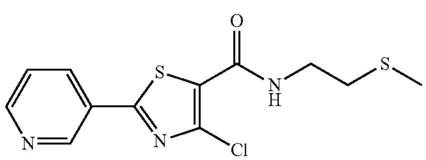 | LCMS_1: 314 (M + 1) |
| 1.147 | 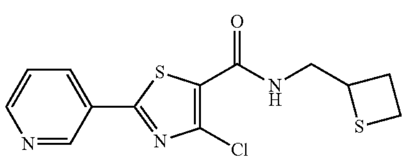 [SMILES: O=C(NCC1CCS1)c1sc(-c2cccnc2)nc1Cl] | LCMS_1: 326 (M + 1) |
| 1.148 | 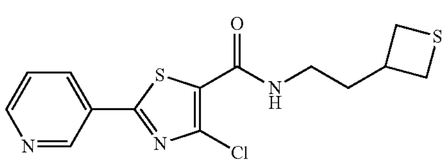 [SMILES: O=C(NCCC1CSC1)c1sc(-c2cccnc2)nc1Cl] | LCMS_1: 340 (M + 1) |
| 1.149 | 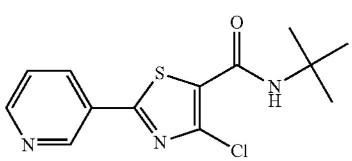 [SMILES: CC(C)(C)NC(=O)c1sc(-c2cccnc2)nc1Cl] | LCMS_1: 296 (M + 1) |
| 1.150 | 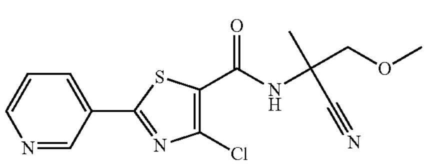 [SMILES: COCC(C)(C#N)NC(=O)c1sc(-c2cccnc2)nc1Cl] | LCMS_1: 337 (M + 1) |

(1.022)
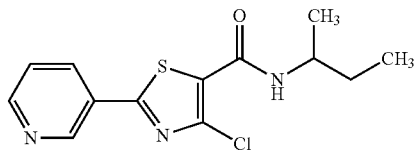
| Compound No. | Structure | Phys. Data |
|---|---|---|
| 1.151 | 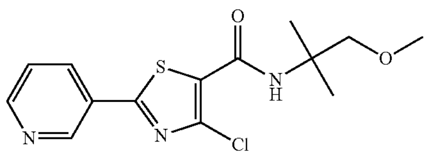 [SMILES: COCC(C)(C)NC(=O)c1sc(-c2cccnc2)nc1Cl] | LCMS_1: 326 (M + 1) |
| 1.152 | 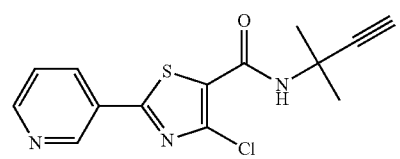 [SMILES: C#CC(C)(C)NC(=O)c1sc(-c2cccnc2)nc1Cl] | LCMS_1: 306 (M + 1) |
| 1.153 | 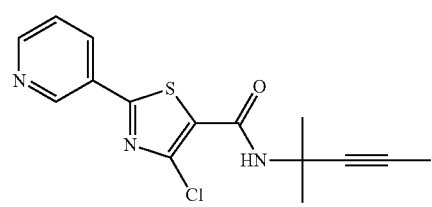 [SMILES: CC#CC(C)(C)NC(=O)c1sc(-c2cccnc2)nc1Cl] | LCMS_1: 320 (M + 1) |
| 1.154 | 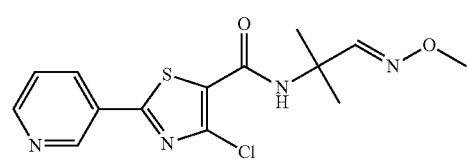 [SMILES: CO/N=C/C(C)(C)NC(=O)c1sc(-c2cccnc2)nc1Cl] | LCMS_1: 339 (M + 1) |
| 1.155 | 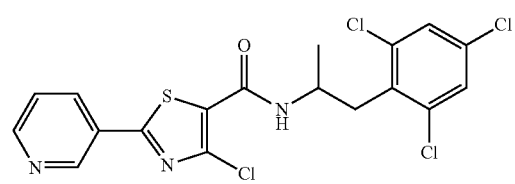 [SMILES: CC(Cc1c(Cl)cc(Cl)cc1Cl)NC(=O)c1sc(-c2cccnc2)nc1Cl] | LCMS_1: 460 (M + 1) |
| 1.156 | 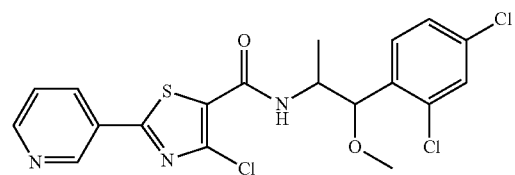 [SMILES: COC(c1ccc(Cl)cc1Cl)C(C)NC(=O)c1sc(-c2cccnc2)nc1Cl] | LCMS_1: 456 (M + 1) |
| 1.157 | 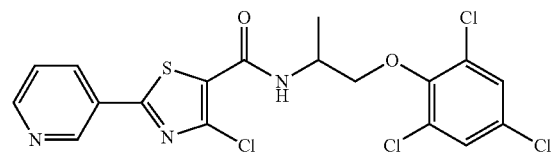 [SMILES: CC(COc1c(Cl)cc(Cl)cc1Cl)NC(=O)c1sc(-c2cccnc2)nc1Cl] | LCMS_1: 476 (M + 1) |
| 1.158 | 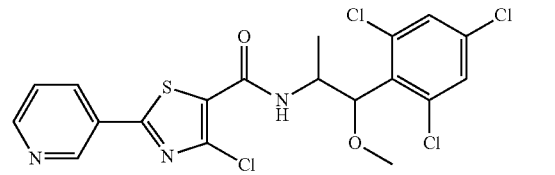 [SMILES: COC(c1c(Cl)cc(Cl)cc1Cl)C(C)NC(=O)c1sc(-c2cccnc2)nc1Cl] | LCMS_1: 490 (M + 1) |

-continued
(1.022)
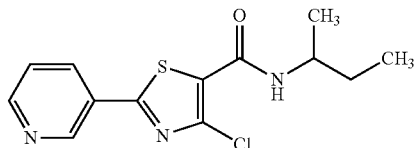
| Compound No. | Structure | Phys. Data |
|---|---|---|
| 1.159 | 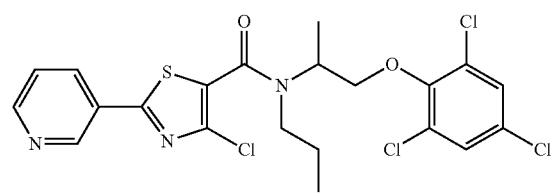 [SMILES: CCCN(C(=O)c1sc(-c2cccnc2)nc1Cl)C(C)COc1c(Cl)cc(Cl)cc1Cl] | LCMS_1: 516 (M + 1) |
| 1.160 | 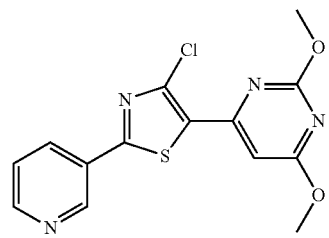 [SMILES: COc1cc(-c2sc(-c3cccnc3)nc2Cl)nc(OC)n1] | LCMS_2: 335 (M + 1) |
| 1.161 | 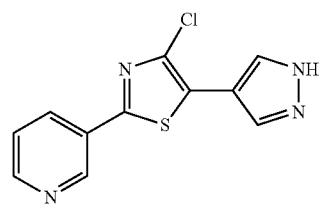 [SMILES: Clc1nc(-c2cccnc2)sc1-c1cn[nH]c1] | LCMS_2: 263 (M + 1) |
| 1.162 | 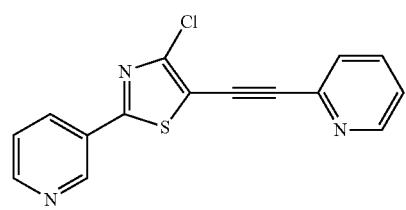 [SMILES: Clc1nc(-c2cccnc2)sc1C#Cc1ccccn1] | LCMS_2: 298 (M + 1) |
| 1.163 | 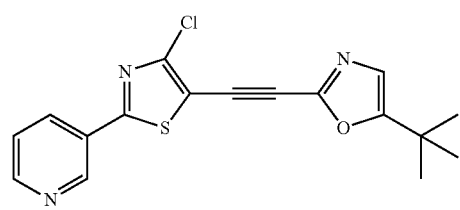 [SMILES: CC(C)(C)c1cnc(C#Cc2sc(-c3cccnc3)nc2Cl)o1] | LCMS_2: 344 (M + 1) |
| 1.164 | 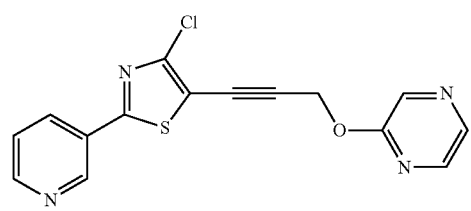 [SMILES: Clc1nc(-c2cccnc2)sc1C#CCOc1cnccn1] | LCMS_2: 329 (M + 1) |

(1.022)

| Compound No. | Structure | Phys. Data |
|---|---|---|
| | [structure: 2-(pyridin-3-yl)-4-chloro-N-(1-methylpropyl)thiazole-5-carboxamide] | |
| 1.165 | [structure: 4-chloro-2-(pyridin-3-yl)thiazole linked to oxadiazole bearing 6-methylpyridin-2-yl] | LCMS_2: 356 (M + 1) |
| 1.166 | [structure: 4-chloro-2-(pyridin-3-yl)thiazole linked to thiadiazole bearing 6-methylpyridin-2-yl] | LCMS_2: 372 (M + 1) |
| 1.167 | [structure: 4-chloro-2-(pyridin-3-yl)thiazole-5-carboxamide N-CH2-P(=O)(CH3)2] | $^{31}$P-NMR (162 MHz, CDCl3): 41.1 ppm |

LCMS Methods:

LCMS 1:

LCMS. Spectra were recorded on a ACQUITY SQD Mass Spectrometer (Waters Corp. Milford, Mass., USA) mass spectrometer equipped with an electrospray source (ESI; source temperature 150° C.; desolvation temperature 400° C.; cone voltage 20 V; cone gas flow 60 l/hour, desolvation gas flow 700 l/hour, mass range: 100 to 800 Da) and a Waters ACQUITY UPLC (column: Waters ACQUITY UPLC HSS T3, 30 mm, Internal diameter of column: 2.1 mm; Particle Size: 1.8 micron; column temperature: 60° C.; flow rate 0.75 ml/min; eluent A: Water/Methanol 9:1, 0.1% formic acid; eluent B: Acetonitrile, 0.1% formic acid; gradient: 0 min 5% B; 2-2.8 (6-7.7) min 100% B; 2.9-3 (7.8-8) min 5% B; UV-detection: 210-500 nm, resolution 2 nm. The flow was split postcolumn prior to MS analysis.

LCMS 2:

LCMS. Spectra were recorded on a ZDQ (Waters Corp. Milford, Mass., USA) mass spectrometer equipped with an electrospray source (ESI; source temperature 100° C.; desolvation temperature 350° C.; cone voltage 45 V; cone gas flow 50 l/hour, desolvation gas flow 400 l/hour, mass range: 100 to 900 Da) and an Agilent 1100 HPLC (column: Gemini C18, 3 um, 30×3 mm (Phenomenex, Torrance, Calif., USA); column temperature: 60° C.; flow rate 1.7 ml/min; eluent A: H$_2$O+5% MeOH+0.05% HCOOH; eluent B: Acetonitril+ 0.05% HCOOH; gradient: 0-10 min 5% B; 2-2.8 (6-7.7) min 100% B; 2.9-3 (7.8-8) min 5% B; UV-detection: 210-500 nm, resolution 2 nm. The flow was split postcolumn prior to MS analysis.

FORMULATION EXAMPLES (%=PERCENT BY WEIGHT)

Example F1: Emulsion Concentrates

| | a) | b) | c) |
|---|---|---|---|
| Active ingredient | 25% | 40% | 50% |
| Calcium dodecylbenzenesulfonate | 5% | 8% | 6% |
| Castor oil polyethylene glycol ether (36 mol of EO) | 5% | — | — |
| Tributylphenoxypolyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by dilution with water.

Example F2: Solutions

|  | a) | b) | c) | d) |
|---|---|---|---|---|
| Active ingredient | 80% | 10% | 5% | 95% |
| Ethylene glycol monomethyl ether | 20% | — | — | — |
| Polyethylene glycol MW 400 | — | 70% | — | — |
| N-Methylpyrrolid-2-one | — | 20% | — | — |
| Epoxidized coconut oil | — | — | 1% | 5% |
| Petroleum ether (boiling range: 160-190°) | — | — | 94% | — |

The solutions are suitable for use in the form of microdrops.

Example F3: Granules

|  | a) | b) | c) | d) |
|---|---|---|---|---|
| Active ingredient | 5% | 10% | 8% | 21% |
| Kaolin | 94% | — | 79% | 54% |
| Highly disperse silica | 1% | — | 13% | 7% |
| Attapulgite | — | 90% | — | 18% |

The active ingredient is dissolved in dichloromethane, the solution is sprayed onto the carrier(s), and the solvent is subsequently evaporated in vacuo.

Example F4: Dusts

|  | a) | b) |
|---|---|---|
| Active ingredient | 2% | 5% |
| Highly disperse silica | 1% | 5% |
| Talc | 97% | — |
| Kaolin | — | 90% |

Ready-to-use dusts are obtained by intimately mixing the carriers and the active ingredient.

Example F5: Wettable Powders

|  | a) | b) | c) |
|---|---|---|---|
| Active ingredient | 25% | 50% | 75% |
| Sodium lignosulfonate | 5% | 5% | — |
| Sodium lauryl sulfate | 3% | — | 5% |
| Sodium diisobutylnaphthalenesulfonate | — | 6% | 10% |
| Octylphenoxypolyethylene glycol ether (7-8 mol of EO) | — | 2% | — |
| Highly disperse silica | 5% | 10% | 10% |
| Kaolin | 62% | 27% | — |

The active ingredient is mixed with the additives and the mixture is ground thoroughly in a suitable mill. This gives wettable powders, which can be diluted with water to give suspensions of any desired concentration.

Example F6: Extruder Granules

| Active ingredient | 10% |
|---|---|
| Sodium lignosulfonate | 2% |
| Carboxymethylcellulose | 1% |
| Kaolin | 87% |

The active ingredient is mixed with the additives, and the mixture is ground, moistened with water, extruded, granulated and dried in a stream of air.

Example F7: Coated Granules

| Active ingredient | 3% |
|---|---|
| Polyethylene glycol (MW 200) | 3% |
| Kaolin | 94% |

In a mixer, the finely ground active ingredient is applied uniformly to the kaolin, which has been moistened with the polyethylene glycol. This gives dust-free coated granules.

Example F8: Suspension Concentrate

| Active ingredient | 40% |
|---|---|
| Ethylene glycol | 10% |
| Nonylphenoxypolyethylene glycol ether (15 mol of EO) | 6% |
| Sodium lignosulfonate | 10% |
| Carboxymethylcellulose | 1% |
| 37% aqueous formaldehyde solution | 0.2% |
| Silicone oil (75% aqueous emulsion) | 0.8% |
| Water | 32% |

The finely ground active ingredient is mixed intimately with the additives. Suspensions of any desired concentration can be prepared from the thus resulting suspension concentrate by dilution with water.

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "P" means "one compound selected from the group consisting of the compounds of formulae 1.001 to 1.167 described in Tables P of the present invention"):

an adjuvant selected from the group of substances consisting of petroleum oils (alternative name) (628)+P, an acaricide selected from the group of substances consisting of 1,1-bis(4-chlorophenyl)-2-ethoxyethanol (IUPAC name) (910)+P, 2,4-dichlorophenyl benzenesulfonate (IUPAC/Chemical Abstracts name) (1059)+P, 2-fluoro-N-methyl-N-1-naphthylacetamide (IUPAC name) (1295)+P, 4-chlorophenyl phenyl sulfone (IUPAC name) (981)+P, abamectin (1)+P, acequinocyl (3)+P, acetoprole [CCN]+P, acrinathrin (9)+P, aldicarb (16)+P, aldoxycarb (863)+P, alpha-cypermethrin (202)+P, amidithion (870)+P, amidoflumet [CCN]+P, amidothioate (872)+P, amiton (875)+P, amiton hydrogen oxalate (875)+P, amitraz (24)+P, aramite (881)+P, arsenous oxide (882)+P, AVI 382 (compound code)+P, AZ 60541 (compound code)+P, azinphos-ethyl (44)+P, azinphos-methyl (45)+P, azobenzene (IUPAC name) (888)+P, azocyclotin (46)+P, azothoate (889)+P, benomyl (62)+P, benoxafos (alternative name) [CCN]+P, benoximate (71)+P, benzyl benzoate (IUPAC name) [CCN]+P, bifenazate (74)+P, bifenthrin (76)+P, binapacryl (907)+P, brofenvalerate (alternative name)+P, bromocyclen (918)+P, bromophos (920)+P, bromophos-ethyl (921)+P, bromopropylate (94)+P, buprofezin (99)+P, butocarboxim (103)+P, butoxycarboxim (104)+P, butylpyridaben (alternative name)+P, calcium polysulfide (IUPAC name) (111)+P, camphechlor (941)+P, carbanolate (943)+P, carbaryl (115)+P, carbofuran (118)+P, carbophenothion (947)+P, CGA 50'439 (development code) (125)+P, chinomethionat (126)+P, chlorbenside (959)+P, chlordimeform (964)+P, chlordimeform hydrochloride (964)+P, chlorfenapyr (130)+P, chlorfenethol (968)+P, chlorfenson (970)+P, chlorfensulphide (971)+P, chlorfenvinphos (131)+P, chlorobenzilate (975)+P, chloromebuform (977)+P, chloromethiuron (978)+P, chloropropylate (983)+P, chlorpyrifos (145)+P, chlorpyrifos-methyl (146)+P, chlorthiophos (994)+P, cinerin I (696)+P, cinerin II (696)+P, cinerins (696)+P, clofentezine (158)+P, closantel (alternative name) [CCN]+P, coumaphos (174)+P, crotamiton (alternative name) [CCN]+P, crotoxyphos (1010)+P, cufraneb (1013)+P, cyanthoate (1020)+P, cyflumetofen (CAS Reg. No.: 400882-07-7)+P, cyhalothrin (196)+P, cyhexatin (199)+P, cypermethrin (201)+P, DCPM (1032)+P, DDT (219)+P, demephion (1037)+P, demephion-O (1037)+P, demephion-S (1037)+P, demeton (1038)+P, demeton-methyl (224)+P, demeton-O (1038)+P, demeton-O-methyl (224)+P, demeton-S (1038)+P, demeton-S-methyl (224)+P, demeton-S-methylsulphon (1039)+P, diafenthiuron (226)+P, dialifos (1042)+P, diazinon (227)+P, dichlofluanid (230)+P, dichlorvos (236)+P, dicliphos (alternative name)+P, dicofol (242)+P, dicrotophos (243)+P, dienochlor (1071)+P, dimefox (1081)+P, dimethoate (262)+P, dinactin (alternative name) (653)+P, dinex (1089)+P, dinex-diclexine (1089)+P, dinobuton (269)+P, dinocap (270)+P, dinocap-4 [CCN]+P, dinocap-6 [CCN]+P, dinocton (1090)+P, dinopenton (1092)+P, dinosulfon (1097)+P, dinoterbon (1098)+P, dioxathion (1102)+P, diphenyl sulfone (IUPAC name) (1103)+P, disulfiram (alternative name) [CCN]+P, disulfoton (278)+P, DNOC (282)+P, dofenapyn (1113)+P, doramectin (alternative name) [CCN]+P, endosulfan (294)+P, endothion (1121)+P, EPN (297)+P, eprinomectin (alternative name) [CCN]+P, ethion (309)+P, ethoate-methyl (1134)+P, etoxazole (320)+P, etrimfos (1142)+P, fenazaflor (1147)+P, fenazaquin (328)+P, fenbutatin oxide (330)+P, fenothiocarb (337)+P, fenpropathrin (342)+P, fenpyrad (alternative name)+P, fenpyroximate (345)+P, fenson (1157)+P, fentrifanil (1161)+P, fenvalerate (349)+P, fipronil (354)+P, fluacrypyrim (360)+P, fluazuron (1166)+P, flubenzimine (1167)+P, flucycloxuron (366)+P, flucythrinate (367)+P, fluenetil (1169)+P, flufenoxuron (370)+P, flumethrin (372)+P, fluorbenside (1174)+P, fluvalinate (1184)+P, FMC 1137 (development code) (1185)+P, formetanate (405)+P, formetanate hydrochloride (405)+P, formothion (1192)+P, formparanate (1193)+P, gamma-HCH (430)+P, glyodin (1205)+P, halfenprox (424)+P, heptenophos (432)+P, hexadecyl cyclopropanecarboxylate (IUPAC/Chemical Abstracts name) (1216)+P, hexythiazox (441)+P, iodomethane (IUPAC name) (542)+P, isocarbophos (alternative name) (473)+P, isopropyl O-(methoxyaminothiophosphoryl)salicylate (IUPAC name) (473)+P, ivermectin (alternative name) [CCN]+P, jasmolin I (696)+P, jasmolin II (696)+P, jodfenphos (1248)+P, lindane (430)+P, lufenuron (490)+P, malathion (492)+P, malonoben (1254)+P, mecarbam (502)+P, mephosfolan (1261)+P, mesulfen (alternative name) [CCN]+P, methacrifos (1266)+P, methamidophos (527)+P, methidathion (529)+P, methiocarb (530)+P, methomyl (531)+P, methyl bromide (537)+P, metolcarb (550)+P, mevinphos (556)+P, mexacarbate (1290)+P, milbemectin (557)+P, milbemycin oxime (alternative name) [CCN]+P, mipafox (1293)+P, monocrotophos (561)+P, morphothion (1300)+P, moxidectin (alternative name) [CCN]+P, naled (567)+P, NC-184 (compound code)+P, NC-512 (compound code)+P, nifluridide (1309)+P, nikkomycins (alternative name) [CCN]+P, nitrilacarb (1313)+P, nitrilacarb 1:1 zinc chloride complex (1313)+P, NNI-0101 (compound code)+P, NNI-0250 (compound code)+P, omethoate (594)+P, oxamyl (602)+P, oxydeprofos (1324)+P, oxydisulfoton (1325)+P, pp'-DDT (219)+P, parathion (615)+P, permethrin (626)+P, petroleum oils (alternative name) (628)+P, phenkapton (1330)+P, phenthoate (631)+P, phorate (636)+P, phosalone (637)+P, phosfolan (1338)+P, phosmet (638)+P, phosphamidon (639)+P, phoxim (642)+P, pirimiphos-methyl (652)+P, polychloroterpenes (traditional name) (1347)+P, polynactins (alternative name) (653)+P, proclonol (1350)+P, profenofos (662)+P, promacyl (1354)+P, propargite (671)+P, propetamphos (673)+P, propoxur (678)+P, prothidathion (1360)+P, prothoate (1362)+P, pyrethrin I (696)+P, pyrethrin II (696)+P, pyrethrins (696)+P, pyridaben (699)+P, pyridaphenthion (701)+P, pyrimidifen (706)+P, pyrimitate (1370)+P, quinalphos (711)+P, quintiofos (1381)+P, R-1492 (development code) (1382)+P, RA-17 (development code) (1383)+P, rotenone (722)+P, schradan (1389)+P, sebufos (alternative name)+P, selamectin (alternative name) [CCN]+P, SI-0009 (compound code)+P, sophamide (1402)+P, spirodiclofen (738)+P, spiromesifen (739)+P, SSI-121 (development code) (1404)+P, sulfiram (alternative name) [CCN]+P, sulfluramid (750)+P, sulfotep (753)+P, sulphur (754)+P, SZI-121 (development code) (757)+P, tau-fluvalinate (398)+P, tebufenpyrad (763)+P, TEPP (1417)+P, terbam (alternative name)+P, tetrachlorvinphos (777)+P, tetradifon (786)+P, tetranactin (alternative name) (653)+P, tetrasul (1425)+P, thiafenox (alternative name)+P, thiocarboxime (1431)+P, thiofanox (800)+P, thiometon (801)+P, thioquinox (1436)+P, thuringiensin (alternative name) [CCN]+P, triamiphos (1441)+P, triarathene (1443)+P, triazophos (820)+P, triazuron (alternative name)+P, trichlorfon (824)+P, trifenofos (1455)+P, trinactin (alternative name) (653)+P, vamidothion (847)+P, vaniliprole [CCN] and YI-5302 (compound code)+P, an algicide selected from the group of substances consisting of bethoxazin [CCN]+P, copper dioctanoate (IUPAC name) (170)+P, copper sulfate (172)+P, cybutryne [CCN]+P, dichlone (1052)+P, dichlorophen (232)+P, endothal (295)+P, fentin (347)+P, hydrated lime [CCN]+P, nabam (566)+P, quinoclamine (714)+P, quinonamid (1379)+P, simazine (730)+P, triphenyltin acetate (IUPAC name) (347) and triphenyltin hydroxide (IUPAC name) (347)+P, an anthelmintic selected from the group of substances consisting of abamectin (1)+P, crufomate (1011)+P, doramectin (alternative name) [CCN]+P, emamectin (291)+P, emamectin benzoate (291)+P, eprinomectin (alternative name)

[CCN]+P, ivermectin (alternative name) [CCN]+P, milbemycin oxime (alternative name) [CCN]+P, moxidectin (alternative name) [CCN]+P, piperazine [CCN]+P, selamectin (alternative name) [CCN]+P, spinosad (737) and thiophanate (1435)+P, an avicide selected from the group of substances consisting of chloralose (127)+P, endrin (1122)+P, fenthion (346)+P, pyridin-4-amine (IUPAC name) (23) and strychnine (745)+P, a bactericide selected from the group of substances consisting of 1-hydroxy-1H-pyridine-2-thione (IUPAC name) (1222)+P, 4-(quinoxalin-2-ylamino)benzenesulfonamide (IUPAC name) (748)+P, 8-hydroxyquinoline sulfate (446)+P, bronopol (97)+P, copper dioctanoate (IUPAC name) (170)+P, copper hydroxide (IUPAC name) (169)+P, cresol [CCN]+P, dichlorophen (232)+P, dipyrithione (1105)+P, dodicin (1112)+P, fenaminosulf (1144)+P, formaldehyde (404)+P, hydrargaphen (alternative name) [CCN]+P, kasugamycin (483)+P, kasugamycin hydrochloride hydrate (483)+P, nickel bis(dimethyldithiocarbamate) (IUPAC name) (1308)+P, nitrapyrin (580)+P, octhilinone (590)+P, oxolinic acid (606)+P, oxytetracycline (611)+P, potassium hydroxyquinoline sulfate (446)+P, probenazole (658)+P, streptomycin (744)+P, streptomycin sesquisulfate (744)+P, tecloftalam (766)+P, and thiomersal (alternative name) [CCN]+P, a biological agent selected from the group of substances consisting of *Adoxophyes orana* GV (alternative name) (12)+P, *Agrobacterium radiobacter* (alternative name) (13)+P, *Amblyseius* spp. (alternative name) (19)+P, *Anagrapha falcifera* NPV (alternative name) (28)+P, *Anagrus atomus* (alternative name) (29)+P, *Aphelinus abdominalis* (alternative name) (33)+P, *Aphidius colemani* (alternative name) (34)+P, *Aphidoletes aphidimyza* (alternative name) (35)+P, *Autographa californica* NPV (alternative name) (38)+P, *Bacillus firmus* (alternative name) (48)+P, *Bacillus sphaericus* Neide (scientific name) (49)+P, *Bacillus thuringiensis* Berliner (scientific name) (51)+P, *Bacillus thuringiensis* subsp. *aizawai* (scientific name) (51)+P, *Bacillus thuringiensis* subsp. *israelensis* (scientific name) (51)+P, *Bacillus thuringiensis* subsp. *japonensis* (scientific name) (51)+P, *Bacillus thuringiensis* subsp. *kurstaki* (scientific name) (51)+P, *Bacillus thuringiensis* subsp. *tenebrionis* (scientific name) (51)+P, *Beauveria bassiana* (alternative name) (53)+P, *Beauveria brongniartii* (alternative name) (54)+P, *Chrysoperla carnea* (alternative name) (151)+P, *Cryptolaemus montrouzieri* (alternative name) (178)+P, *Cydia pomonella* GV (alternative name) (191)+P, *Dacnusa sibirica* (alternative name) (212)+P, *Diglyphus isaea* (alternative name) (254)+P, *Encarsia formosa* (scientific name) (293)+P, *Eretmocerus eremicus* (alternative name) (300)+P, *Helicoverpa zea* NPV (alternative name) (431)+P, *Heterorhabditis bacteriophora* and *H. megidis* (alternative name) (433)+P, *Hippodamia convergens* (alternative name) (442)+P, *Leptomastix dactylopii* (alternative name) (488)+P, *Macrolophus caliginosus* (alternative name) (491)+P, *Mamestra brassicae* NPV (alternative name) (494)+P, *Metaphycus helvolus* (alternative name) (522)+P, *Metarhizium anisopliae* var. *acridum* (scientific name) (523)+P, *Metarhizium anisopliae* var. *anisopliae* (scientific name) (523)+P, *Neodiprion sertifer* NPV and *N. lecontei* NPV (alternative name) (575)+P, *Orius* spp. (alternative name) (596)+P, *Paecilomyces fumosoroseus* (alternative name) (613)+P, *Phytoseiulus persimilis* (alternative name) (644)+P, *Spodoptera exigua* multicapsid nuclear polyhedrosis virus (scientific name) (741)+P, *Steinernema bibionis* (alternative name) (742)+P, *Steinernema carpocapsae* (alternative name) (742)+P, *Steinernema feltiae* (alternative name) (742)+P, *Steinernema glaseri* (alternative name) (742)+P, *Steinernema riobrave* (alternative name) (742)+P, *Steinernema riobravis* (alternative name) (742)+P, *Steinernema scapterisci* (alternative name) (742)+P, *Steinernema* spp. (alternative name) (742)+P, *Trichogramma* spp. (alternative name) (826)+P, *Typhlodromus occidentalis* (alternative name) (844) and *Verticillium lecanii* (alternative name) (848)+P, a soil sterilant selected from the group of substances consisting of iodomethane (IUPAC name) (542) and methyl bromide (537)+P, a chemosterilant selected from the group of substances consisting of apholate [CCN]+P, bisazir (alternative name) [CCN]+P, busulfan (alternative name) [CCN]+P, diflubenzuron (250)+P, dimatif (alternative name) [CCN]+P, hemel [CCN]+P, hempa [CCN]+P, metepa [CCN]+P, methiotepa [CCN]+P, methyl apholate [CCN]+P, morzid [CCN]+P, penfluron (alternative name) [CCN]+P, tepa [CCN]+P, thiohempa (alternative name) [CCN]+P, thiotepa (alternative name) [CCN]+P, tretamine (alternative name) [CCN] and uredepa (alternative name) [CCN]+P, an insect pheromone selected from the group of substances consisting of (E)-dec-5-en-1-yl acetate with (E)-dec-5-en-1-ol (IUPAC name) (222)+P, (E)-tridec-4-en-1-yl acetate (IUPAC name) (829)+P, (E)-6-methylhept-2-en-4-ol (IUPAC name) (541)+P, (E,Z)-tetradeca-4,10-dien-1-yl acetate (IUPAC name) (779)+P, (Z)-dodec-7-en-1-yl acetate (IUPAC name) (285)+P, (Z)-hexadec-11-enal (IUPAC name) (436)+P, (Z)-hexadec-11-en-1-yl acetate (IUPAC name) (437)+P, (Z)-hexadec-13-en-11-yn-1-yl acetate (IUPAC name) (438)+P, (Z)-icos-13-en-10-one (IUPAC name) (448)+P, (Z)-tetradec-7-en-1-al (IUPAC name) (782)+P, (Z)-tetradec-9-en-1-ol (IUPAC name) (783)+P, (Z)-tetradec-9-en-1-yl acetate (IUPAC name) (784)+P, (7E,9Z)-dodeca-7,9-dien-1-yl acetate (IUPAC name) (283)+P, (9Z,11E)-tetradeca-9,11-dien-1-yl acetate (IUPAC name) (780)+P, (9Z,12E)-tetradeca-9,12-dien-1-yl acetate (IUPAC name) (781)+P, 14-methyloctadec-1-ene (IUPAC name) (545)+P, 4-methylnonan-5-ol with 4-methylnonan-5-one (IUPAC name) (544)+P, alpha-multistriatin (alternative name) [CCN]+P, brevicomin (alternative name) [CCN]+P, codlelure (alternative name) [CCN]+P, codlemone (alternative name) (167)+P, cuelure (alternative name) (179)+P, disparlure (277)+P, dodec-8-en-1-yl acetate (IUPAC name) (286)+P, dodec-9-en-1-yl acetate (IUPAC name) (287)+P, dodeca-8+P, 10-dien-1-yl acetate (IUPAC name) (284)+P, dominicalure (alternative name) [CCN]+P, ethyl 4-methyloctanoate (IUPAC name) (317)+P, eugenol (alternative name) [CCN]+P, frontalin (alternative name) [CCN]+P, gossyplure (alternative name) (420)+P, grandlure (421)+P, grandlure I (alternative name) (421)+P, grandlure II (alternative name) (421)+P, grandlure III (alternative name) (421)+P, grandlure IV (alternative name) (421)+P, hexalure [CCN]+P, ipsdienol (alternative name) [CCN]+P, ipsenol (alternative name) [CCN]+P, japonilure (alternative name) (481)+P, lineatin (alternative name) [CCN]+P, litlure (alternative name) [CCN]+P, looplure (alternative name) [CCN]+P, medlure [CCN]+P, megatomoic acid (alternative name) [CCN]+P, methyl eugenol (alternative name) (540)+P, muscalure (563)+P, octadeca-2,13-dien-1-yl acetate (IUPAC name) (588)+P, octadeca-3,13-dien-1-yl acetate (IUPAC name) (589)+P, orfralure (alternative name) [CCN]+P, oryctalure (alternative name) (317)+P, ostramone (alternative name) [CCN]+P, siglure [CCN]+P, sordidin (alternative name) (736)+P, sulcatol (alternative name) [CCN]+P, tetradec-11-en-1-yl acetate (IUPAC name) (785)+P, trimedlure (839)+P, trimedlure A (alternative name) (839)+P, trimedlure B₁ (alternative name) (839)+P, trimedlure B₂ (alternative name) (839)+P, trimedlure C (alternative name) (839) and trunccall (alternative name) [CCN]+P, an insect repellent selected from the group of substances consisting of 2-(octylthio)ethanol (IUPAC name) (591)+P, butopyronoxyl (933)+P, butoxy(polypropylene glycol) (936)+P, dibutyl adipate (IUPAC name) (1046)+P, dibutyl phthalate (1047)+P, dibutyl succinate (IUPAC name) (1048)+P, diethyltoluamide [CCN]+P, dimethyl carbate [CCN]+P, dimethyl phthalate [CCN]+P, ethyl hexanediol (1137)+P, hexamide [CCN]+P, methoquin-butyl (1276)+P, methylneodecanamide [CCN]+P, oxamate [CCN] and picaridin [CCN]+P, an insecticide selected from the group of substances consisting of 1-dichloro-1-nitroethane (IUPAC/Chemical Abstracts name) (1058)+P, 1,1-dichloro-2,2-bis(4-ethylphenyl)ethane (IUPAC name) (1056), +P, 1,2-dichloropropane (IUPAC/Chemical Abstracts name) (1062)+P, 1,2-dichloropropane with 1,3-dichloropropene (IUPAC name) (1063)+P, 1-bromo-2-chloroethane (IUPAC/Chemical Abstracts name) (916)+P, 2,2,2-trichloro-1-(3,4-dichlorophenyl)ethyl acetate (IUPAC name) (1451)+P, 2,2-dichlorovinyl 2-ethylsulphinylethyl methyl phosphate (IUPAC name) (1066)+P, 2-(1,3-dithiolan-2-yl)phenyl dimethylcarbamate (IUPAC/Chemical Abstracts name) (1109)+P, 2-(2-butoxyethoxy)ethyl thiocyanate (IUPAC/Chemical Abstracts name) (935)+P, 2-(4,5-dimethyl-1,3-dioxolan-2-yl)phenyl methylcarbamate (IUPAC/Chemical Abstracts name) (1084)+P, 2-(4-chloro-3,5-xylyloxy)ethanol (IUPAC name) (986)+P, 2-chlorovinyl diethyl phosphate (IUPAC name) (984)+P, 2-imidazolidone (IUPAC name) (1225)+P, 2-isovalerylindan-1,3-dione (IUPAC name) (1246)+P, 2-methyl(prop-2-ynyl)aminophenyl methylcarbamate (IUPAC name) (1284)+P, 2-thiocyanatoethyl laurate (IUPAC name) (1433)+P, 3-bromo-1-chloroprop-1-ene (IUPAC name) (917)+P, 3-methyl-1-phenylpyrazol-5-yl dimethylcarbamate (IUPAC name) (1283)+P, 4-methyl(prop-2-ynyl)amino-3,5-xylyl methylcarbamate (IUPAC name) (1285)+P, 5,5-dimethyl-3-oxocyclohex-1-enyl dimethylcarbamate (IUPAC name) (1085)+P, abamectin (1)+P, acephate (2)+P, acetamiprid (4)+P, acethion (alternative name) [CCN]+P, acetoprole [CCN]+P, acrinathrin (9)+P, acrylonitrile (IUPAC name) (861)+P, alanycarb (15)+P, aldicarb (16)+P, aldoxycarb (863)+P, aldrin (864)+P, allethrin (17)+P, allosamidin (alternative name) [CCN]+P, allyxycarb (866)+P, alpha-cypermethrin (202)+P, alpha-ecdysone (alternative name) [CCN]+P, aluminium phosphide (640)+P, amidithion (870)+P, amidothioate (872)+P, aminocarb (873)+P, amiton (875)+P, amiton hydrogen oxalate (875)+P, amitraz (24)+P, anabasine (877)+P, athidathion (883)+P, AVI 382 (compound code)+P, AZ 60541 (compound code)+P, azadirachtin (alternative name) (41)+P, azamethiphos (42)+P, azinphos-ethyl (44)+P, azinphos-methyl (45)+P, azothoate (889)+P, *Bacillus thuringiensis* delta endotoxins (alternative name) (52)+P, barium hexafluorosilicate (alternative name) [CCN]+P, barium polysulfide (IUPAC/Chemical Abstracts name) (892)+P, barthrin [CCN]+P, Bayer 22/190 (development code) (893)+P, Bayer 22408 (development code) (894)+P, bendiocarb (58)+P, benfuracarb (60)+P, bensultap (66)+P, beta-cyfluthrin (194)+P, beta-cypermethrin (203)+P, bifenthrin (76)+P, bioallethrin (78)+P, bioallethrin S-cyclopentenyl isomer (alternative name) (79)+P, bioethanomethrin [CCN]+P, biopermethrin (908)+P, bioresmethrin (80)+P, bis(2-chloroethyl) ether (IUPAC name) (909)+P, bistrifluron (83)+P, borax (86)+P, brofenvalerate (alternative name)+P, bromfenvinfos (914)+P, bromocyclen (918)+P, bromo-DDT (alternative name) [CCN]+P, bromophos (920)+P, bromophos-ethyl (921)+P, bufencarb (924)+P, buprofezin (99)+P, butacarb (926)+P, butathiofos (927)+P, butocarboxim (103)+P, butonate (932)+P, butoxycarboxim (104)+P, butylpyridaben (alternative name)+P, cadusafos (109)+P, calcium arsenate [CCN]+P, calcium cyanide (444)+P, calcium polysulfide (IUPAC name) (111)+P, camphechlor (941)+P, carbanolate (943)+P, carbaryl (115)+P, carbofuran (118)+P, carbon disulfide (IUPAC/Chemical Abstracts name) (945)+P, carbon tetrachloride (IUPAC name) (946)+P, carbophenothion (947)+P, carbosulfan (119)+P, cartap (123)+P, cartap hydrochloride (123)+P, cevadine (alternative name) (725)+P, chlorbicyclen (960)+P, chlordane (128)+P, chlordecone (963)+P, chlordimeform (964)+P, chlordimeform hydrochloride (964)+P, chlorethoxyfos (129)+P, chlorfenapyr (130)+P, chlorfenvinphos (131)+P, chlorfluazuron (132)+P, chlormephos (136)+P, chloroform [CCN]+P, chloropicrin (141)+P, chlorphoxim (989)+P, chlorprazophos (990)+P, chlorpyrifos (145)+P, chlorpyrifos-methyl (146)+P, chlorthiophos (994)+P, chromafenozide (150)+P, cinerin I (696)+P, cinerin II (696)+P, cinerins (696)+P, cis-resmethrin (alternative name)+P, cismethrin (80)+P, clocythrin (alternative name)+P, cloethocarb (999)+P, closantel (alternative name) [CCN]+P, clothianidin (165)+P, copper acetoarsenite [CCN]+P, copper arsenate [CCN]+P, copper oleate [CCN]+P, coumaphos (174)+P, coumithoate (1006)+P, crotamiton (alternative name) [CCN]+P, crotoxyphos (1010)+P, crufomate (1011)+P, cryolite (alternative name) (177)+P, CS 708 (development code) (1012)+P, cyanofenphos (1019)+P, cyanophos (184)+P, cyanthoate (1020)+P, cyclethrin [CCN]+P, cycloprothrin (188)+P, cyfluthrin (193)+P, cyhalothrin (196)+P, cypermethrin (201)+P, cyphenothrin (206)+P, cyromazine (209)+P, cythioate (alternative name) [CCN]+P, d-limonene (alternative name) [CCN]+P, d-tetramethrin (alternative name) (788)+P, DAEP (1031)+P, dazomet (216)+P, DDT (219)+P, decarbofuran (1034)+P, deltamethrin (223)+P, demephion (1037)+P, demephion-O (1037)+P, demephion-S (1037)+P, demeton (1038)+P, demeton-methyl (224)+P, demeton-O (1038)+P, demeton-O-methyl (224)+P, demeton-S (1038)+P, demeton-S-methyl (224)+P, demeton-S-methylsulphon (1039)+P, diafenthiuron (226)+P, dialifos (1042)+P, diamidafos (1044)+P, diazinon (227)+P, dicapthon (1050)+P, dichlofenthion (1051)+P, dichlorvos (236)+P, dicliphos (alternative name)+P, dicresyl (alternative name) [CCN]+P, dicrotophos (243)+P, dicyclanil (244)+P, dieldrin (1070)+P, diethyl 5-methylpyrazol-3-yl phosphate (IUPAC name) (1076)+P, diflubenzuron (250)+P, dilor (alternative name) [CCN]+P, dimefluthrin [CCN]+P, dimefox (1081)+P, dimetan (1085)+P, dimethoate (262)+P, dimethrin (1083)+P, dimethylvinphos (265)+P, dimetilan (1086)+P, dinex (1089)+P, dinex-diclexine (1089)+P, dinoprop (1093)+P, dinosam (1094)+P, dinoseb (1095)+P, dinotefuran (271)+P, diofenolan (1099)+P, dioxabenzofos (1100)+P, dioxacarb (1101)+P, dioxathion (1102)+P, disulfoton (278)+P, dithicrofos (1108)+P, DNOC (282)+P, doramectin (alternative name) [CCN]+P, DSP (1115)+P, ecdysterone (alternative name) [CCN]+P, EI 1642 (development code) (1118)+P, emamectin (291)+P, emamectin benzoate (291)+P, EMPC (1120)+P, empenthrin (292)+P, endosulfan (294)+P, endothion (1121)+P, endrin (1122)+P, EPBP (1123)+P, EPN (297)+P, epofenonane (1124)+P, eprinomectin (alternative name) [CCN]+P, esfenvalerate (302)+P, etaphos (alternative name) [CCN]+P, ethiofencarb (308)+P, ethion (309)+P, ethiprole (310)+P, ethoate-methyl (1134)+P, ethoprophos (312)+P, ethyl formate (IUPAC name) [CCN]+P, ethyl-DDD (alternative name) (1056)+P, ethylene dibromide (316)+P, ethylene dichloride (chemical name) (1136)+P, ethylene oxide

[CCN]+P, etofenprox (319)+P, etrimfos (1142)+P, EXD (1143)+P, famphur (323)+P, fenamiphos (326)+P, fenazaflor (1147)+P, fenchlorphos (1148)+P, fenethacarb (1149)+P, fenfluthrin (1150)+P, fenitrothion (335)+P, fenobucarb (336)+P, fenoxacrim (1153)+P, fenoxycarb (340)+P, fenpirithrin (1155)+P, fenpropathrin (342)+P, fenpyrad (alternative name)+P, fensulfothion (1158)+P, fenthion (346)+P, fenthion-ethyl [CCN]+P, fenvalerate (349)+P, fipronil (354)+P, flonicamid (358)+P, flubendiamide (CAS. Reg. No.: 272451-65-7)+P, flucofuron (1168)+P, flucycloxuron (366)+P, flucythrinate (367)+P, fluenetil (1169)+P, flufenerim [CCN]+P, flufenoxuron (370)+P, flufenprox (1171)+P, flumethrin (372)+P, fluvalinate (1184)+P, FMC 1137 (development code) (1185)+P, fonofos (1191)+P, formetanate (405)+P, formetanate hydrochloride (405)+P, formothion (1192)+P, formparanate (1193)+P, fosmethilan (1194)+P, fospirate (1195)+P, fosthiazate (408)+P, fosthietan (1196)+P, furathiocarb (412)+P, furethrin (1200)+P, gamma-cyhalothrin (197)+P, gamma-HCH (430)+P, guazatine (422)+P, guazatine acetates (422)+P, GY-81 (development code) (423)+P, halfenprox (424)+P, halofenozide (425)+P, HCH (430)+P, HEOD (1070)+P, heptachlor (1211)+P, heptenophos (432)+P, heterophos [CCN]+P, hexaflumuron (439)+P, HHDN (864)+P, hydramethylnon (443)+P, hydrogen cyanide (444)+P, hydroprene (445)+P, hyquincarb (1223)+P, imidacloprid (458)+P, imiprothrin (460)+P, indoxacarb (465)+P, iodomethane (IUPAC name) (542)+P, IPSP (1229)+P, isazofos (1231)+P, isobenzan (1232)+P, isocarbophos (alternative name) (473)+P, isodrin (1235)+P, isofenphos (1236)+P, isolane (1237)+P, isoprocarb (472)+P, isopropyl O-(methoxyaminothiophosphoryl)salicylate (IUPAC name) (473)+P, isoprothiolane (474)+P, isothioate (1244)+P, isoxathion (480)+P, ivermectin (alternative name) [CCN]+P, jasmolin I (696)+P, jasmolin II (696)+P, jodfenphos (1248)+P, juvenile hormone I (alternative name) [CCN]+P, juvenile hormone II (alternative name) [CCN]+P, juvenile hormone III (alternative name) [CCN]+P, kelevan (1249)+P, kinoprene (484)+P, lambda-cyhalothrin (198)+P, lead arsenate [CCN]+P, lepimectin (CCN)+P, leptophos (1250)+P, lindane (430)+P, lirimfos (1251)+P, lufenuron (490)+P, lythidathion (1253)+P, m-cumenyl methylcarbamate (IUPAC name) (1014)+P, magnesium phosphide (IUPAC name) (640)+P, malathion (492)+P, malonoben (1254)+P, mazidox (1255)+P, mecarbam (502)+P, mecarphon (1258)+P, menazon (1260)+P, mephosfolan (1261)+P, mercurous chloride (513)+P, mesulfenfos (1263)+P, metaflumizone (CCN)+P, metam (519)+P, metam-potassium (alternative name) (519)+P, metam-sodium (519)+P, methacrifos (1266)+P, methamidophos (527)+P, methanesulphonyl fluoride (IUPAC/Chemical Abstracts name) (1268)+P, methidathion (529)+P, methiocarb (530)+P, methocrotophos (1273)+P, methomyl (531)+P, methoprene (532)+P, methoquin-butyl (1276)+P, methothrin (alternative name) (533)+P, methoxychlor (534)+P, methoxyfenozide (535)+P, methyl bromide (537)+P, methyl isothiocyanate (543)+P, methylchloroform (alternative name) [CCN]+P, methylene chloride [CCN]+P, metofluthrin [CCN]+P, metolcarb (550)+P, metoxadiazone (1288)+P, mevinphos (556)+P, mexacarbate (1290)+P, milbemectin (557)+P, milbemycin oxime (alternative name) [CCN]+P, mipafox (1293)+P, mirex (1294)+P, monocrotophos (561)+P, morphothion (1300)+P, moxidectin (alternative name) [CCN]+P, naftalofos (alternative name) [CCN]+P, naled (567)+P, naphthalene (IUPAC/Chemical Abstracts name) (1303)+P, NC-170 (development code) (1306)+P, NC-184 (compound code)+P, nicotine (578)+P, nicotine sulfate (578)+P, nifluridide (1309)+P, nitenpyram (579)+P, nithiazine (1311)+P, nitrilacarb (1313)+P, nitrilacarb 1:1 zinc chloride complex (1313)+P, NNI-0101 (compound code)+P, NNI-0250 (compound code)+P, nornicotine (traditional name) (1319)+P, novaluron (585)+P, noviflumuron (586)+P, O-5-dichloro-4-iodophenyl O-ethyl ethylphosphonothioate (IUPAC name) (1057)+P, O,O-diethyl O-4-methyl-2-oxo-2H-chromen-7-yl phosphorothioate (IUPAC name) (1074)+P, O,O-diethyl O-6-methyl-2-propylpyrimidin-4-yl phosphorothioate (IUPAC name) (1075)+P, O,O,O',O'-tetrapropyl dithiopyrophosphate (IUPAC name) (1424)+P, oleic acid (IUPAC name) (593)+P, omethoate (594)+P, oxamyl (602)+P, oxydemeton-methyl (609)+P, oxydeprofos (1324)+P, oxydisulfoton (1325)+P, pp'-DDT (219)+P, para-dichlorobenzene [CCN]+P, parathion (615)+P, parathion-methyl (616)+P, penfluron (alternative name) [CCN]+P, pentachlorophenol (623)+P, pentachlorophenyl laurate (IUPAC name) (623)+P, permethrin (626)+P, petroleum oils (alternative name) (628)+P, PH 60-38 (development code) (1328)+P, phenkapton (1330)+P, phenothrin (630)+P, phenthoate (631)+P, phorate (636)+P, phosalone (637)+P, phosfolan (1338)+P, phosmet (638)+P, phosnichlor (1339)+P, phosphamidon (639)+P, phosphine (IUPAC name) (640)+P, phoxim (642)+P, phoxim-methyl (1340)+P, pirimetaphos (1344)+P, pirimicarb (651)+P, pirimiphosethyl (1345)+P, pirimiphos-methyl (652)+P, polychlorodicyclopentadiene isomers (IUPAC name) (1346)+P, polychloroterpenes (traditional name) (1347)+P, potassium arsenite [CCN]+P, potassium thiocyanate [CCN]+P, prallethrin (655)+P, precocene I (alternative name) [CCN]+P, precocene II (alternative name) [CCN]+P, precocene III (alternative name) [CCN]+P, primidophos (1349)+P, profenofos (662)+P, profluthrin [CCN]+P, promacyl (1354)+P, promecarb (1355)+P, propaphos (1356)+P, propetamphos (673)+P, propoxur (678)+P, prothidathion (1360)+P, prothiofos (686)+P, prothoate (1362)+P, protrifenbute [CCN]+P, pymetrozine (688)+P, pyraclofos (689)+P, pyrazophos (693)+P, pyresmethrin (1367)+P, pyrethrin I (696)+P, pyrethrin II (696)+P, pyrethrins (696)+P, pyridaben (699)+P, pyridalyl (700)+P, pyridaphenthion (701)+P, pyrimidifen (706)+P, pyrimitate (1370)+P, pyriproxyfen (708)+P, quassia (alternative name) [CCN]+P, quinalphos (711)+P, quinalphosmethyl (1376)+P, quinothion (1380)+P, quintiofos (1381)+P, R-1492 (development code) (1382)+P, rafoxanide (alternative name) [CCN]+P, resmethrin (719)+P, rotenone (722)+P, RU 15525 (development code) (723)+P, RU 25475 (development code) (1386)+P, ryania (alternative name) (1387)+P, ryanodine (traditional name) (1387)+P, sabadilla (alternative name) (725)+P, schradan (1389)+P, sebufos (alternative name)+P, selamectin (alternative name) [CCN]+P, SI-0009 (compound code)+P, SI-0205 (compound code)+P, SI-0404 (compound code)+P, SI-0405 (compound code)+P, silafluofen (728)+P, SN 72129 (development code) (1397)+P, sodium arsenite [CCN]+P, sodium cyanide (444)+P, sodium fluoride (IUPAC/Chemical Abstracts name) (1399)+P, sodium hexafluorosilicate (1400)+P, sodium pentachlorophenoxide (623)+P, sodium selenate (IUPAC name) (1401)+P, sodium thiocyanate [CCN]+P, sophamide (1402)+P, spinosad (737)+P, spiromesifen (739)+P, spirotetrmat (CCN)+P, sulcofuron (746)+P, sulcofuron-sodium (746)+P, sulfluramid (750)+P, sulfotep (753)+P, sulphuryl fluoride (756)+P, sulprofos (1408)+P, tar oils (alternative name) (758)+P, tau-fluvalinate (398)+P, tazimcarb (1412)+P, TDE (1414)+P, tebufenozide (762)+P, tebufenpyrad (763)+P, tebupirimfos (764)+P, teflubenzuron (768)+P, tefluthrin (769)+P, temephos (770)+P, TEPP (1417)+P, terallethrin (1418)+P, terbam (alternative name)+P, terbufos (773)+P, tetrachloroethane [CCN]+P, tetrachlorvinphos (777)+P, tetramethrin (787)+P, thetacypermethrin (204)+P, thiacloprid (791)+P, thiafenox (alternative name)+P, thiamethoxam (792)+P, thicrofos (1428)+P, thiocarboxime (1431)+P, thiocyclam (798)+P, thiocyclam hydrogen oxalate (798)+P, thiodicarb (799)+P, thiofanox (800)+P, thiometon (801)+P, thionazin (1434)+P, thiosultap (803)+P, thiosultap-sodium (803)+P, thuringiensin (alternative name) [CCN]+P, tolfenpyrad (809)+P, tralomethrin (812)+P, transfluthrin (813)+P, transpermethrin (1440)+P, triamiphos (1441)+P, triazamate (818)+P, triazophos (820)+P, triazuron (alternative name)+P, trichlorfon (824)+P, trichlormetaphos-3 (alternative name) [CCN]+P, trichloronat (1452)+P, trifenofos (1455)+P, triflumuron (835)+P, trimethacarb (840)+P, triprene (1459)+P, vamidothion (847)+P, vaniliprole [CCN]+P, veratridine (alternative name) (725)+P, veratrine (alternative name) (725)+P, XMC (853)+P, xylylcarb (854)+P, YI-5302 (compound code)+P, zeta-cypermethrin (205)+P, zetamethrin (alternative name)+P, zinc phosphide (640)+P, zolaprofos (1469) and ZXI 8901 (development code) (858)+P, cyantraniliprole [736994-63-19+P, chlorantraniliprole [500008-45-7]+P, cyenopyrafen [560121-52-0]+P, cyflumetofen[400882-07-7]+P, pyrifluquinazon [337458-27-2]+P, spinetoram [187166-40-1+187166-15-0]+P, spirotetramat [203313-25-1]+P, sulfoxaflor [946578-00-3]+P, flufiprole [704886-18-0]+P, meperfluthrin [915288-13-0]+P, tetramethylfluthrin [84937-88-2]+P, a molluscicide selected from the group of substances consisting of bis(tributyltin) oxide (IUPAC name) (913)+P, bromoacetamide [CCN]+P, calcium arsenate [CCN]+P, cloethocarb (999)+P, copper acetoarsenite [CCN]+P, copper sulfate (172)+P, fentin (347)+P, ferric phosphate (IUPAC name) (352)+P, metaldehyde (518)+P, methiocarb (530)+P, niclosamide (576)+P, niclosamide-olamine (576)+P, pentachlorophenol (623)+P, sodium pentachlorophenoxide (623)+P, tazimcarb (1412)+P, thiodicarb (799)+P, tributyltin oxide (913)+P, trifenmorph (1454)+P, trimethacarb (840)+P, triphenyltin acetate (IUPAC name) (347) and triphenyltin hydroxide (IUPAC name) (347)+P, pyriprole [394730-71-3]+P, a nematicide selected from the group of substances consisting of AKD-3088 (compound code)+P, 1,2-dibromo-3-chloropropane (IUPAC/Chemical Abstracts name) (1045)+P, 1,2-dichloropropane (IUPAC/Chemical Abstracts name) (1062)+P, 1,2-dichloropropane with 1,3-dichloropropene (IUPAC name) (1063)+P, 1,3-dichloropropene (233)+P, 3,4-dichlorotetrahydrothiophene 1,1-dioxide (IUPAC/Chemical Abstracts name) (1065)+P, 3-(4-chlorophenyl)-5-methylrhodanine (IUPAC name) (980)+P, 5-methyl-6-thioxo-1,3,5-thiadiazinan-3-ylacetic acid (IUPAC name) (1286)+P, 6-isopentenylaminopurine (alternative name) (210)+P, abamectin (1)+P, acetoprole [CCN]+P, alanycarb (15)+P, aldicarb (16)+P, aldoxycarb (863)+P, AZ 60541 (compound code)+P, benclothiaz [CCN]+P, benomyl (62)+P, butylpyridaben (alternative name)+P, cadusafos (109)+P, carbofuran (118)+P, carbon disulfide (945)+P, carbosulfan (119)+P, chloropicrin (141)+P, chlorpyrifos (145)+P, cloethocarb (999)+P, cytokinins (alternative name) (210)+P, dazomet (216)+P, DBCP (1045)+P, DCIP (218)+P, diamidafos (1044)+P, dichlofenthion (1051)+P, dicliphos (alternative name)+P, dimethoate (262)+P, doramectin (alternative name) [CCN]+P, emamectin (291)+P, emamectin benzoate (291)+P, eprinomectin (alternative name) [CCN]+P, ethoprophos (312)+P, ethylene dibromide (316)+P, fenamiphos (326)+P, fenpyrad (alternative name)+P, fensulfothion (1158)+P, fosthiazate (408)+P, fosthietan (1196)+P, furfural (alternative name) [CCN]+P, GY-81 (development code) (423)+P, heterophos [CCN]+P, iodomethane (IUPAC name) (542)+P, isamidofos (1230)+P, isazofos (1231)+P, ivermectin (alternative name) [CCN]+P, kinetin (alternative name) (210)+P, mecarphon (1258)+P, metam (519)+P, metam-potassium (alternative name) (519)+P, metam-sodium (519)+P, methyl bromide (537)+P, methyl isothiocyanate (543)+P, milbemycin oxime (alternative name) [CCN]+P, moxidectin (alternative name) [CCN]+P, *Myrothecium verrucaria* composition (alternative name) (565)+P, NC-184 (compound code)+P, oxamyl (602)+P, phorate (636)+P, phosphamidon (639)+P, phosphocarb [CCN]+P, sebufos (alternative name)+P, selamectin (alternative name) [CCN]+P, spinosad (737)+P, terbam (alternative name)+P, terbufos (773)+P, tetrachlorothiophene (IUPAC/Chemical Abstracts name) (1422)+P, thiafenox (alternative name)+P, thionazin (1434)+P, triazophos (820)+P, triazuron (alternative name)+P, xylenols [CCN]+P, YI-5302 (compound code) and zeatin (alternative name) (210)+P, fluensulfone[318290-98-1]+P, a nitrification inhibitor selected from the group of substances consisting of potassium ethylxanthate [CCN] and nitrapyrin (580)+P, a plant activator selected from the group of substances consisting of acibenzolar (6)+P, acibenzolar-S-methyl (6)+P, probenazole (658) and *Reynoutria sachalinensis* extract (alternative name) (720)+P, a rodenticide selected from the group of substances consisting of 2-isovalerylindan-1,3-dione (IUPAC name) (1246)+P, 4-(quinoxalin-2-ylamino)benzenesulfonamide (IUPAC name) (748)+P, alpha-chlorohydrin [CCN]+P, aluminium phosphide (640)+P, antu (880)+P, arsenous oxide (882)+P, barium carbonate (891)+P, bisthiosemi (912)+P, brodifacoum (89)+P, bromadiolone (91)+P, bromethalin (92)+P, calcium cyanide (444)+P, chloralose (127)+P, chlorophacinone (140)+P, cholecalciferol (alternative name) (850)+P, coumachlor (1004)+P, coumafuryl (1005)+P, coumatetralyl (175)+P, crimidine (1009)+P, difenacoum (246)+P, difethialone (249)+P, diphacinone (273)+P, ergocalciferol (301)+P, flocoumafen (357)+P, fluoroacetamide (379)+P, fluropadine (1183)+P, fluropadine hydrochloride (1183)+P, gamma-HCH (430)+P, HCH (430)+P, hydrogen cyanide (444)+P, iodomethane (IUPAC name) (542)+P, lindane (430)+P, magnesium phosphide (IUPAC name) (640)+P, methyl bromide (537)+P, norbormide (1318)+P, phosacetim (1336)+P, phosphine (IUPAC name) (640)+P, phosphorus [CCN]+P, pindone (1341)+P, potassium arsenite [CCN]+P, pyrinuron (1371)+P, scilliroside (1390)+P, sodium arsenite [CCN]+P, sodium cyanide (444)+P, sodium fluoroacetate (735)+P, strychnine (745)+P, thallium sulfate [CCN]+P, warfarin (851) and zinc phosphide (640)+P, a synergist selected from the group of substances consisting of 2-(2-butoxyethoxy)ethyl piperonylate (IUPAC name) (934)+P, 5-(1,3-benzodioxol-5-yl)-3-hexylcyclohex-2-enone (IUPAC name) (903)+P, farnesol with nerolidol (alternative name) (324)+P, MB-599 (development code) (498)+P, MGK 264 (development code) (296)+P, piperonyl butoxide (649)+P, piprotal (1343)+P, propyl isomer (1358)+P, S421 (development code) (724)+P, sesamex (1393)+P, sesasmolin (1394) and sulfoxide (1406)+P, an animal repellent selected from the group of substances consisting of anthraquinone (32)+P, chloralose (127)+P, copper naphthenate [CCN]+P, copper oxychloride (171)+P, diazinon (227)+P, dicyclopentadiene (chemical name) (1069)+P, guazatine (422)+P, guazatine acetates (422)+P, methiocarb (530)+P, pyridin-4-amine (IUPAC name) (23)+P, thiram (804)+P, trimethacarb (840)+P, zinc naphthenate [CCN] and ziram (856)+P, a virucide selected from the group of substances consisting of imanin (alternative name) [CCN] and ribavirin (alternative name) [CCN]+P, a wound protectant selected from the group of substances consisting of mercuric oxide (512)+P, octhilinone (590) and thiophanate-methyl (802)+P, and biologically active compounds selected from the group consisting of azaconazole (60207-31-0]+P, bitertanol [70585-36-3]+P, bromuconazole [116255-48-2]+P, cyproconazole [94361-06-5]+P, difenoconazole [119446-68-3]+P, diniconazole [83657-24-3]+P, epoxiconazole [106325-08-0]+P, fenbuconazole [114369-43-6]+P, fluquinconazole [136426-54-5]+P, flusilazole [85509-19-9]+P, flutriafol [76674-21-0]+P, hexaconazole [79983-71-4]+P, imazalil [35554-44-0]+P, imibenconazole [86598-92-7]+P, ipconazole [125225-28-7]+P, metconazole [125116-23-6]+P, myclobutanil [88671-89-0]+P, pefurazoate [101903-30-4]+P, penconazole [66246-88-6]+P, prothioconazole [178928-70-6]+P, pyrifenox [88283-41-4]+P, prochloraz [67747-09-5]+P, propiconazole [60207-90-1]+P, simeconazole [149508-90-7]+P, tebuconazole [107534-96-3]+P, tetraconazole [112281-77-3]+P, triadimefon [43121-43-3]+P, triadimenol [55219-65-3]+P, triflumizole [99387-89-0]+P, triticonazole [131983-72-7]+P, ancymidol [12771-68-5]+P, fenarimol [60168-88-9]+P, nuarimol [63284-71-9]+P, bupirimate [41483-43-6]+P, dimethirimol [5221-53-4]+P, ethirimol [23947-60-6]+P, dodemorph [1593-77-7]+P, fenpropidine [67306-00-7]+P, fenpropimorph [67564-91-4]+P, spiroxamine [118134-30-8]+P, tridemorph [81412-43-3]+P, cyprodinil [121552-61-2]+P, mepanipyrim [110235-47-7]+P, pyrimethanil [53112-28-0]+P, fenpiclonil [74738-17-3]+P, fludioxonil [131341-86-1]+P, benalaxyl [71626-11-4]+P, furalaxyl [57646-30-7]+P, metalaxyl [57837-19-1]+P, R-metalaxyl [70630-17-0]+P, ofurace [58810-48-3]+P, oxadixyl [77732-09-3]+P, benomyl [17804-35-2]+P, carbendazim [10605-21-7]+P, debacarb [62732-91-6]+P, fuberidazole [3878-19-1]+P, thiabendazole [148-79-8]+P, chlozolinate [84332-86-5]+P, dichlozoline [24201-58-9]+P, iprodione [36734-19-7]+P, myclozoline [54864-61-8]+P, procymidone [32809-16-8]+P, vinclozoline [50471-44-8]+P, boscalid [188425-85-6]+P, carboxin [5234-68-4]+P, fenfuram [24691-80-3]+P, flutolanil [66332-96-5]+P, mepronil [55814-41-0]+P, oxycarboxin [5259-88-1]+P, penthiopyrad [183675-82-3]+P, thifluzamide [130000-40-7]+P, guazatine [108173-90-6]+P, dodine [2439-10-3] [112-65-2] (free base)+P, iminoctadine [13516-27-3]+P, azoxystrobin [131860-33-8]+P, dimoxystrobin [149961-52-4]+P, enestroburin {Proc. BCPC, Int. Congr., Glasgow, 2003, 1, 93}+P, fluoxastrobin [361377-29-9]+P, kresoxim-methyl [143390-89-0]+P, metominostrobin [133408-50-1]+P, trifloxystrobin [141517-21-7]+P, orysastrobin [248593-16-0]+P, picoxystrobin [117428-22-5]+P, pyraclostrobin [175013-18-0]+P, ferbam [14484-64-1]+P, mancozeb [8018-01-7]+P, maneb [12427-38-2]+P, metiram [9006-42-2]+P, propineb [12071-83-9]+P, thiram [137-26-8]+P, zineb [12122-67-7]+P, ziram [137-30-4]+P, captafol [2425-06-1]+P, captan [133-06-2]+P, dichlofluanid [1085-98-9]+P, fluoroimide [41205-21-4]+P, folpet [133-07-3]+P, tolylfluanid [731-27-1]+P, bordeaux mixture [8011-63-0]+P, copperhydroxid [20427-59-2]+P, copperoxychlorid [1332-40-7]+P, coppersulfat [7758-98-7]+P, copperoxid [1317-39-1]+P, mancopper [53988-93-5]+P, oxine-copper [10380-28-6]+P, dinocap [131-72-6]+P, nitrothal-isopropyl [10552-74-6]+P, edifenphos [17109-49-8]+P, iprobenphos [26087-47-8]+P, isoprothiolane [50512-35-1]+P, phosdiphen [36519-00-3]+P, pyrazophos [13457-18-6]+P, tolclofos-methyl [57018-04-9]+P, acibenzolar-S-methyl [135158-54-2]+P, anilazine [101-05-3]+P, benthiavalicarb [413615-35-7]+P, blasticidin-S [2079-00-7]+P, chinomethionat [2439-01-2]+P, chloroneb [2675-77-6]+P, chlorothalonil [1897-45-6]+P, cyflufenamid [180409-60-3]+P, cymoxanil [57966-95-7]+P, dichlone [117-80-6]+P, diclocymet [139920-32-4]+P, diclomezine [62865-36-5]+P, dicloran [99-30-9]+P, diethofencarb [87130-20-9]+P, dimethomorph [110488-70-5]+P, SYP-LI90 (Flumorph) [211867-47-9]+P, dithianon [3347-22-6]+P, ethaboxam [162650-77-3]+P, etridiazole [2593-15-9]+P, famoxadone [131807-57-3]+P, fenamidone [161326-34-7]+P, fenoxanil [115852-48-7]+P, fentin [668-34-8]+P, ferimzone [89269-64-7]+P, fluazinam [79622-59-6]+P, fluopicolide [239110-15-7]+P, flusulfamide [106917-52-6]+P, fenhexamid [126833-17-8]+P, fosetyl-aluminium [39148-24-8]+P, hymexazol [10004-44-1]+P, iprovalicarb [140923-17-7]+P, IKF-916 (Cyazofamid) [120116-88-3]+P, kasugamycin [6980-18-3]+P, methasulfocarb [66952-49-6]+P, metrafenone [220899-03-6]+P, pencycuron [66063-05-6]+P, phthalide [27355-22-2]+P, polyoxins [11113-80-7]+P, probenazole [27605-76-1]+P, propamocarb [25606-41-1]+P, proquinazid [189278-12-4]+P, pyroquilon [57369-32-1]+P, quinoxyfen [124495-18-7]+P, quintozene [82-68-8]+P, sulphur [7704-34-9]+P, tiadinil [223580-51-6]+P, triazoxide [72459-58-6]+P, tricyclazole [41814-78-2]+P, triforine [26644-46-2]+P, validamycin [37248-47-8]+P, zoxamide (RH7281) [156052-68-5]+P, mandipropamid [374726-62-2]+P, isopyrazam [881685-58-1]+P, sedaxane [874967-67-6]+P, 3-difluoromethyl-1-methyl-1H-pyrazole-4-carboxylic acid (9-dichloromethylene-1,2,3,4-tetrahydro-1,4-methano-naphthalen-5-yl)-amide (disclosed in WO 2007/048556)+P and 3-difluoromethyl-1-methyl-1H-pyrazole-4-carboxylic acid (3',4',5'-trifluoro-biphenyl-2-yl)-amide (disclosed in WO 2006/087343)+P.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright © 1995-2004); for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula I selected from table P with active ingredients described above comprises a compound selected from table P and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from table P and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from table P and the active ingredients as described above is not essential for working the present invention.

The compositions can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compositions according to the invention are also suitable for the protection of plant propagation material, for example seeds, such as fruit, tubers or kernels, or nursery plants, against pests of the abovementioned type. The propagation material can be treated with the compositions prior to planting, for example seed can be treated prior to sowing. Alternatively, the compositions can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention.

BIOLOGICAL EXAMPLES (%=PERCENT BY WEIGHT, UNLESS OTHERWISE SPECIFIED)

Example B1: Activity Against *Spodoptera littoralis* (Egyptian Cotton Leafworm)

(larvicide, feeding/residual contact activity, preventive)

Cotton leaf discs were placed on agar in a 24-well microtiter plate and sprayed with test solutions. After drying, the leaf discs were infested with 5 $L_1$ larvae. The samples were checked for mortality, repellent effect, feeding behaviour, and growth regulation 3 days after treatment.

In this test, compound 1.156 showed an activity of over 80% at a concentration of 200 ppm.

Example B2: Activity Against *Heliothis virescens* (Tobacco Budworm)

(ovo-larvicide, feeding/contact activity, curative)

Eggs (0-24 h old) were placed in 24-well microtiter plate on artificial diet and treated with test solutions by pipetting. After an incubation period of 4 days, samples were checked for egg mortality, larval mortality, and growth regulation.

In this test, compounds 1.001, 1.127, 1.139 and 1.140 showed an activity of over 80% at a concentration of 200 ppm.

Example B3: *Plutella xylostella* (Diamond Back Moth)

(larvicide, feeding/residual contact activity, preventive)

24-well microtiter plate (MTP) with artificial diet was treated with test solutions by pipetting. After drying, the MTP's were infested with larvae (L2) (10-15 per well). After an incubation period of 5 days, samples were checked for larval mortality, antifeedant and growth regulation.

In this test, compound 1.001 showed an activity of over 80% at a concentration of 200 ppm.

Example B4: Activity Against *Myzus Persicae* (Green Peach Aphid)

(mixed population, feeding/residual contact activity, preventive)

Sunflower leaf discs were placed on agar in a 24-well microtiter plate and sprayed with test solutions. After drying, the leaf discs were infested with an aphid population of mixed ages. After an incubation period of 6 days, samples were checked for mortality and special effects (e.g. phytotoxicity). In this test, compounds 1.005, 1.007, 1.011, 1.021, 1.026, 1.038, 1.039, 1.053, 1.069, 1.072, 1.079, 1.085, 1.086, 1.088, 1.089, 1.090, 1.094, 1.095, 1.100, 1.119, 1.120, 1.130, 1.142, 1.144, 1.145, 1.146, 1.147, 1.148, 1.149, 1.150, 1.152 and 1.153 showed an activity of over 80% at a concentration of 200 ppm.

Example B5: Activity Against *Myzus persicae* (Green Peach Aphid)

(mixed population, systemic/feeding activity, curative)

Roots of pea seedlings, infested with an aphid population of mixed ages, were placed directly in the test solutions. 6 days after introduction, samples were checked for mortality and special effects on the plant. In this test, compounds 1.007, 1.086, 1.088, 1.090, 1.093, 1.095, 1.120, 1.143, 1.145, 1.146, 1.147 and 1.148 showed an activity of over 80% at a concentration of 24 ppm.

Example B6: Activity Against *Bemisia tabaci* (Cotton White Fly)

(Adults, feeding/residual contact activity, preventive)

Cotton leaf discs are placed on agar in a 24-well microtiter plate and sprayed with test solutions. After drying, the leaf discs are infested with 12 to 18 adults. After an incubation period of 6 days after infestation, samples are checked for mortality and special effects (e.g. phytotoxicity).

In this test, compounds 1.005, 1.011, 1.020 showed an activity of over 80% at a concentration of 200 ppm.

Example B7: Activity Against *Tetranychus urticae* (Two-Spotted Spider Mite)

(mixed population, feeding/residual contact activity, preventive)

Bean leaf discs on agar in 24-well microtiter plates are sprayed with test solutions. After drying, the leaf discs are infested with mite populations of mixed ages. 8 days later, discs are checked for egg mortality, larval mortality, and adult mortality.

In this test, compounds 1.001, 1.096, 1.124, 1.131, 1.132, 1.138, 1.156, 1.160 showed an activity of over 80% at a concentration of 200 ppm.

Comparison of the Insecticidal Activity of Compounds According to the Invention with the Structurally Closest Compound from the State of the Art (Compound No. 39 Described on Page 66 of WO2009/149858):

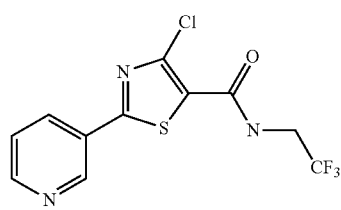

(Compound 1.005 according to the invention)

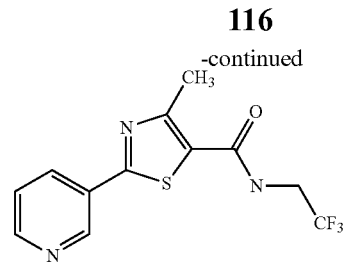

(Compound No. 39 according to state of the art)

Example B8: Activity Against *Aphis craccivora*

(mixed population, contact/feeding)

Pea seedlings, infested with an aphid population of mixed ages, were treated with diluted test solutions in a spray chamber. Six days after treatment, samples were checked for mortality.

Results are shown in Table B1:

TABLE B1

| Activity against *Aphis craccivora* | | |
|---|---|---|
| Compound: | Concentration (ppm) | Death rate (%) after 5 days |
| Comp. 39 (state of the art) | 50 | 99 |
| Comp. 39 (state of the art) | 25 | 99 |
| Comp. 39 (state of the art) | 12.5 | 85 |
| Comp. 39 (state of the art) | 3 | 35 |
| Comp. 1.005 (invention) | 50 | 90 |
| Comp. 1.005 (invention) | 25 | 30 |
| Comp. 1.005 (invention) | 12.5 | 0 |
| Comp. 1.005 (invention) | 3 | 0 |

Table B1 shows that compound no. 1.005 according to the invention exerts a substantially better insecticidal action on *Aphis craccivora* than the compound from the state of the art. Especially at low application rates (25, 12.5 and 3 ppm) the compound according to the invention is far superior to the compound of the state of the art. This enhanced effect was not to be expected on the basis of the structural similarity of these compounds.

What is claimed is:

1. A compound of formula I

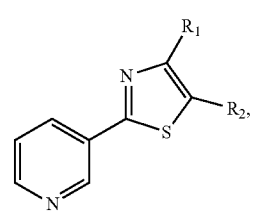

wherein
$R_1$ is chloro; and
$R_2$ is a group —C(O)N($R_3$)$R_4$; wherein
$R_3$ is hydrogen, and $C_1$-$C_6$alkyl, which can be mono- to polysubstituted by substituents selected from the group consisting of $C_1$-$C_6$alkylthio, $C_1$-$C_6$haloalkyl, $C_1$-$C_6$alkylsulfinyl, halogen, cyano, hydroxy, $C_1$-$C_6$alkoxy, $C_2$-$C_6$alkenyl, $C_2$-$C_6$alkynyl, $C_1$-$C_6$alkoxy-$C_3$-$C_6$alkynyl, di-$C_1$-$C_4$alkyl-phosphinoylmethyl, —C≡N—O—$C_1$-$C_6$alkyl;

or is $C_1$-$C_6$alkoxycarbonylamino; and $R_4$ is hydrogen, $C_1$-$C_6$alkyl, or $C_1$-$C_6$haloalkyl; or an agrochemically acceptable salt, an isomer, an enantiomer, a tautomer, or an N-oxide of the compound.

2. A pesticidal composition, which comprises at least one compound of formula I according to claim 1 or a tautomer thereof, in each case in free form or in agrochemic ally utilizable salt form, as active ingredient and at least one auxiliary.

* * * * *